United States Patent
Kofoed et al.

(10) Patent No.: US 10,946,074 B2
(45) Date of Patent: Mar. 16, 2021

(54) GLP-1 DERIVATIVES AND USES THEREOF

(71) Applicant: Novo Nordisk A/S, Bagsvaerd (DK)

(72) Inventors: Jacob Kofoed, Vaerloese (DK); Janos Tibor Kodra, Koebenhavn OE (DK); Lars Linderoth, Hilleroed (DK); Patrick William Garibay, Holte (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 16/077,759

(22) PCT Filed: Mar. 2, 2017

(86) PCT No.: PCT/EP2017/054895
§ 371 (c)(1),
(2) Date: Aug. 14, 2018

(87) PCT Pub. No.: WO2017/149070
PCT Pub. Date: Sep. 8, 2017

(65) Prior Publication Data
US 2019/0038721 A1 Feb. 7, 2019

(30) Foreign Application Priority Data

Mar. 3, 2016 (EP) ..................... 16158388

(51) Int. Cl.
*A61K 38/26* (2006.01)
*A61K 47/54* (2017.01)
*A61K 47/60* (2017.01)
*C07K 14/605* (2006.01)
*A61K 38/00* (2006.01)

(52) U.S. Cl.
CPC ............ *A61K 38/26* (2013.01); *A61K 47/542* (2017.08); *A61K 47/543* (2017.08); *A61K 47/545* (2017.08); *A61K 47/60* (2017.08); *C07K 14/605* (2013.01); *A61K 38/00* (2013.01)

(58) Field of Classification Search
CPC ........ A61K 38/22; A61K 38/26; A61K 47/54; A61K 47/542; A61K 47/543; A61K 47/545; A61K 47/60; C07K 14/575; C07K 14/605
See application file for complete search history.

(56) References Cited

FOREIGN PATENT DOCUMENTS

| CN | 101255191 A | 9/2008 |
|---|---|---|
| CN | 102180963 A | 9/2011 |
| CN | 103087178 A | 5/2013 |
| WO | 2012140117 A1 | 10/2012 |
| WO | 2014202727 A1 | 12/2014 |
| WO | 2015/127273 A1 | 8/2015 |

OTHER PUBLICATIONS

Google Translation of CN 101255191 A (Sep. 3, 2008) (Year: 2008).*
Manandhar et al. Glucagon-like Peptide-1 (GLP-1) Analogs: Recent Advances, New Possibilities, and Therapeutic Implications. Journal of Medicinal Chemistry. Oct. 24, 2014, vol. 58, pp. 1020-1037. (Year: 2010).*
Xiao et al. Biological Activities of Glucagon-Like Peptide-1 Analogues in Vitro and in Vivo. Biochemistry. 2001, vol. 40, No. 9, pp. 2860-2869. (Year: 2001).*
Deacon et al "Dipeptidyl Peptidase IV Resistant Analogues of Glucagon-like Peptide-1 which have extended metabolic stability and improved biological activity." Diabetologia 1998vol. 41 Issue 3 pp. 271-278. Spec.
Mentlein, Rolf "Dipeptidyl-peptidase IV (CD26)—role in the inactivation of regulatory peptides" Regulatory Peptides Nov. 1999 vol. 85 Issue 1 pp. 9-24 ID, Spec.

* cited by examiner

*Primary Examiner* — Jeffrey E. Russel
(74) *Attorney, Agent, or Firm* — Rosemarie R. Wilk-Orescan

(57) ABSTRACT

The invention relates to GLP-1 analogues and derivatives having a Trp at a position corresponding to position 8 of GLP-1(7-37), and their pharmaceutical use e.g. in the treatment of type 2 diabetes. These Trp8 compounds are very stable against degradation by DPP-IV, while maintaining the capability to bind to and activate the GLP-1 receptor. The derivatives have one or two substituents (P-L) attached to a Lys residue of the GLP-1 analogue via an optional Branching group (B), wherein P is a Protracting moiety such as a fatty diacid, and L is a linker consisting of one or more linker elements such as, for example, 8-amino-3,6-dioxaoctanoic acid. Examples of compounds of the invention include the 8W variants of liraglutide and dulaglutide. The invention also relates to a method for the fully recombinant preparation of 8W GLP-1 analogues and derivatives which is more simple and thereby cheaper as compared to the preparation of known GLP-1 analogues that have been DPP-IV stabilised by inclusion of one or more non-coded amino acids.

15 Claims, 1 Drawing Sheet
Specification includes a Sequence Listing.

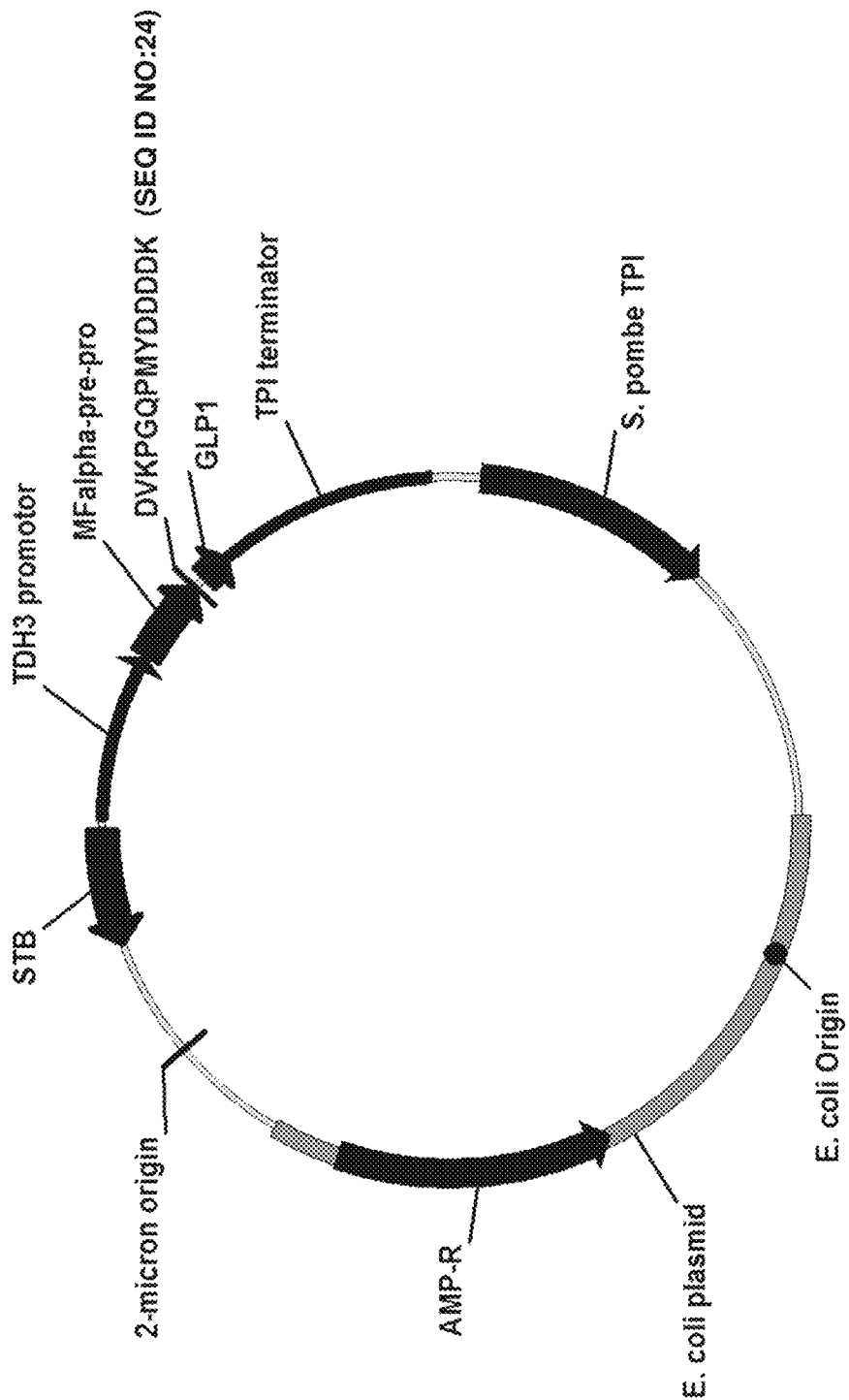

GLP-1 DERIVATIVES AND USES THEREOF

CROSS-REFERENCE TO RELATED APPLICATIONS

This application is a 35 U.S.C. § 371 National Stage application of International Application PCT/EP2017/054895 (WO 2017/149070), filed Mar. 2, 2017, the contents of which are incorporated herein by reference, which claims priority to European Patent Application 16158388.5, filed Mar. 3, 2016.

INCORPORATION-BY-REFERENCE OF THE SEQUENCE LISTING

The Sequence Listing is 21084 bytes, was created on Feb. 28, 2017, updated on Oct. 3, 2019, which is 31 kilobytes, and is incorporated herein by reference.

TECHNICAL FIELD

The present invention relates to derivatives and analogues of glucagon-like peptide 1 (GLP-1), their preparation, and their pharmaceutical use. The GLP-1 analogues and derivatives of the invention have a Trp at a position corresponding to position 8 of GLP-1(7-37) (SEQ ID NO: 1). The derivatives of the invention have one or two substituents (P-L) attached to a Lys residue of the GLP-1 analogue via an optional Branching group (B), wherein P is a Protracting moiety and L is a linker.

BACKGROUND

CN 101255191 A discloses a number of GLP-1 analogues and a microwave-promoted solid phase synthesis method thereof, including in Example 3 Trp8-GLP-1(7-36) amide which is SEQ ID NO: 4 in the sequence listing of this Chinese application.

GLP-1 derivatives having two substituents attached to one or two Lys residues of various GLP-1 analogues are disclosed in, e.g., WO2012/140117 A1 and WO 2014/202727 A1 (without and with a branching group, respectively).

Regulatory Peptides vol. 85 (1999), p. 9-24 by Rolf Mentlein is a review of the role of dipeptidyl-peptidase IV (CD26)-role in the inactivation of regulatory peptides.

Diabetologia vol. 41 (1998), p. 271-278 by Deacon et al discuss dipeptidyl peptidase IV resistant analogues of GLP-1 which have extended metabolic stability and improved biological activity.

SUMMARY

The invention relates to GLP-1 analogues and derivatives that have a Trp at a position corresponding to position 8 of GLP-1(7-37) (SEQ ID NO: 1). The derivatives of the invention have one or two substituents (P-L) attached to a Lys residue of the GLP-1 analogue via an optional Branching group (B), wherein P is a Protracting moiety and L is a linker.

More in particular the invention relates to a derivative of formula I: $(P-L)_U$-B-GLP1, wherein GLP1 is a GLP-1 analogue having a Trp at a position corresponding to position 8 of GLP-1(7-37) (SEQ ID NO: 1), (P-L) is a substituent attached to a Lys residue of the GLP-1 analogue via an optional Branching group (B) and comprising a Protracting moiety (P) and a Linker (L), U represents the number of substituents (P-L) in the derivative and is 1 or 2, wherein each substituent (P-L) comprises (i) a Protracting moiety (P) selected from:

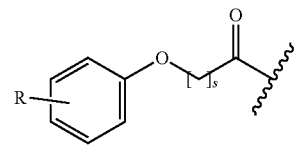

Chem. 10

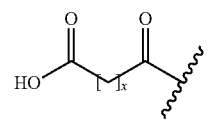

Chem. 11

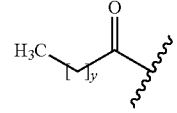

Chem. 12

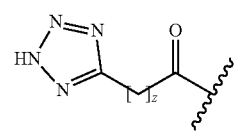

Chem. 13

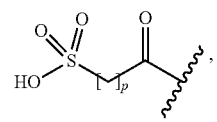

Chem. 14 and (ii) a Linker (L) comprising at least one linker element selected from:

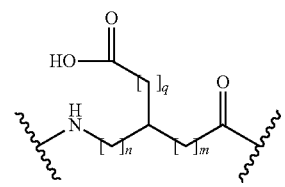

Chem. 15

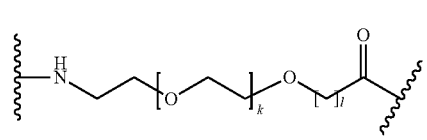

Chem. 16

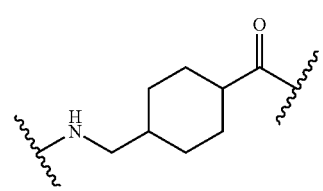

Chem. 17

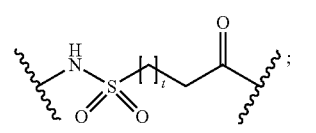

Chem. 18 wherein R is —COOH; each of s, x, y, z, and p independently represents an integer in the range of 8-20; each of n, m, and q independently represents an integer in the range of 0-4; and each of k, l, and t independently represents an integer in the range of 1-5; and (iii) wherein the Branching group (B) if present comprises a Branched linker (BL) selected from:

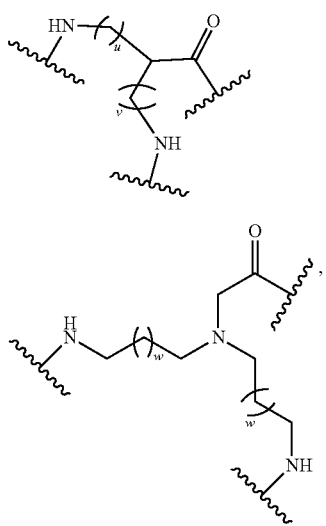

Chem. 19

Chem. 20 wherein u and v independently represents an integer in the range of 0-5 and each w represents an integer in the range of 0-2, with the provisos that when u is 0 v is an integer in the range of 1-5, and when v is 0 u is an integer in the range of 1-5; or a pharmaceutically acceptable salt, amide, or ester thereof.

The invention also relates to a number of specific GLP-1 derivatives, the structural formulae of which are included herein as Chem. numbers 21-32, as well as their pharmaceutically acceptable salts, amides, and esters.

In addition, the invention relates to a number of specific GLP-1 analogues comprising SEQ ID NO: 4, SEQ ID NO: 5, SEQ ID NO: 7, SEQ ID NO: 9, SEQ ID NO: 11, SEQ ID NO: 15, amino acids 1-275 of SEQ ID NO: 15, SEQ ID NO: 16, SEQ ID NO: 18, or SEQ ID NO: 20; as well as their pharmaceutically acceptable salts, amides, or esters.

The invention also relates to pharmaceutical compositions and uses of these analogues and derivatives, as well as methods for their preparation, which comprise the step of recombinantly producing a GLP-1 analogue having Trp at a position corresponding to position 8 of GLP-1(7-37) (SEQ ID NO: 1).

The amino acid sequence of native human GLP-1(7-37) is included in the sequence listing as SEQ ID NO: 1. SEQ ID NO's 4, 5, 7, 9, 11, 15, 16, 18, and 20 are specific GLP-1 analogues of the invention. SEQ ID NO's 2-3, 6, 8, 10, 12, 13, 14, 17, 19, and 21 are specific GLP-1 analagues of comparative GLP-1 compounds.

The analogues and derivatives of the invention are surprisingly very stable against degradation by DPP-IV.

Also or alternatively, the analogues and derivatives of the invention are capable of binding to the GLP-1 receptor.

Also or alternatively, the analogues and derivatives of the invention are capable of activating the GLP-1 receptor.

Also or alternatively, the peptide parts of the derivatives of the invention may be produced fully recombinantly.

Also or alternatively, the analogues and derivatives of the invention are active in vivo.

BRIEF DESCRIPTION OF THE DRAWINGS

FIG. 1 shows a yeast expression plasmid suitable for use in the recombinant production of peptide parts of the GLP-1 derivatives of the invention (SEQ ID NO:24).

DESCRIPTION

In what follows, Greek letters may be represented by their symbol or the corresponding written name, for example: α=alpha; β=beta; ε=epsilon; γ=gamma; δ=delta; ω=omega; etc. Also, the Greek letter of μ may be represented by "u", e.g. in μl=ul, or in M=uM.

An asterisk (*) or a waved line in a chemical formula designates i) a point of attachment, ii) a radical, and/or iii) an unshared electron.

Any stereoactive linker element may be in the D-form, the L-form, the D/L-form, or be a racemic mixture.

When used herein the word "a" generally means "one or more". For example, the derivative of the invention (being defined so as to comprise a GLP-1 analogue having a Trp at a position corresponding to position 8 and wherein "a" specified substituent is attached to "a" Lys residue) may have one or more substituents attached to one or more Lys residues.

Any interval disclosed herein is generally closed, i.e. the end points are included. For example, the number of consecutive —CH$_2$-groups in the substituent attached to a Lys residue of the invention is in the range of 8-20, which means from 8 to 20, both inclusive.

Unless otherwise indicated in the specification, terms presented in singular form generally also include include the plural situation.

The invention also relates to derivatives, GLP-1 analogues, methods of preparation, and pharmaceutical compositions and uses as disclosed herein, wherein open ended terms like "comprises" and "comprising" are replaced with closed terms such as "consists of", "consisting of", and the like.

In a first aspect, the invention relates to a derivative of formula I: (P-L)$_U$-B-GLP1, wherein GLP1 is a GLP-1 analogue having a Trp at a position corresponding to position 8 of GLP-1(7-37) (SEQ ID NO: 1), (P-L) is a substituent attached to a Lys residue of the GLP-1 analogue via an optional Branching group (B) and comprising a Protracting moiety (P) and a Linker (L), U represents the number of substituents (P-L) in the derivative and is 1 or 2, wherein each substituent (P-L) comprises (i) a Protracting moiety (P) selected from:

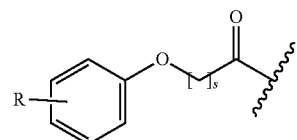

Chem. 10

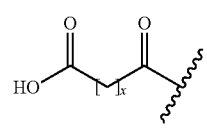

Chem. 11

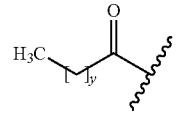

Chem. 12

-continued

Chem. 13
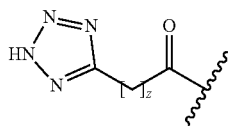

Chem. 14
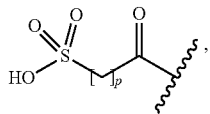

and (ii) a Linker (L) comprising at least one linker element selected from:

Chem. 15
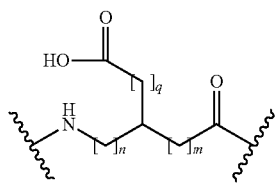

Chem. 16
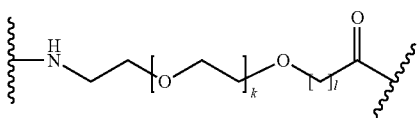

Chem. 17
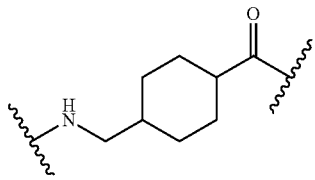

Chem. 18
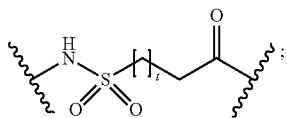

wherein R is —COOH; each of s, x, y, z, and p independently represents an integer in the range of 8-20; each of n, m, and q independently represents an integer in the range of 0-4; and each of k, l, and t independently represents an integer in the range of 1-5; and (iii) wherein the Branching group (B) if present comprises a Branched linker (BL) selected from:

Chem. 19
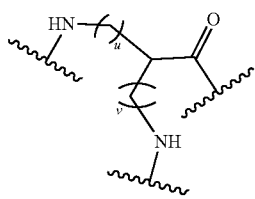

Chem. 20
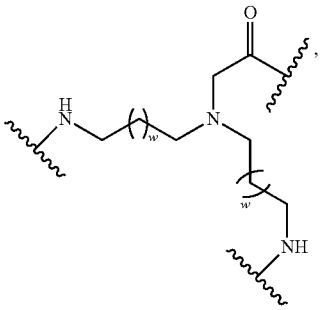

wherein u and v independently represents an integer in the range of 0-5 and each w represents an integer in the range of 0-2, with the provisos that when u is 0 v is an integer in the range of 1-5, and when v is 0 u is an integer in the range of 1-5; or a pharmaceutically acceptable salt, amide, or ester thereof.

The invention also relates to a number of specific GLP-1 derivatives, the structural formulae of which are included herein as Chem. numbers 21-32, as well as their pharmaceutically acceptable salts, amides, and esters.

In its second aspect, the invention relates to a number of specific GLP-1 analogues selected from SEQ ID NO: 4, SEQ ID NO: 5, SEQ ID NO: 7, SEQ ID NO: 9, SEQ ID NO: 11, SEQ ID NO: 15, amino acids 1-275 of SEQ ID NO: 15, SEQ ID NO: 16, SEQ ID NO: 18, or SEQ ID NO: 20; as well as their pharmaceutically acceptable salts, amides, or esters.

In its third aspect the invention relates to pharmaceutical compositions comprising such derivative or analogue and a pharmaceutically acceptable excipient.

In its fourth aspect the invention relates to such derivative or analogue for use as a medicament. In some embodiments the derivative or analogue is for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C; (ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes; (iii) improving β-cell function, such as decreasing β-cell apoptosis, increasing β-cell function and/or β-cell mass, and/or for restoring glucose sensitivity to β-cells; (iv) prevention and/or treatment of cognitive disorders and/or neurodegenerative disorders, such as Alzheimer's disease, Parkinson's disease, and/or multiple sclerosis; (v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence; (vi) prevention and/or treatment of diabetic complications, such as angiopathy; neuropathy, including peripheral neuropathy; nephropathy; and/or retinopathy; (vii) improving lipid parameters, such as prevention and/or treatment of dyslipidemia, lowering total serum lipids; increasing HDL; lowering small, dense LDL;

lowering VLDL; lowering triglycerides; lowering cholesterol; lowering plasma levels of lipoprotein a (Lp(a)) in a human; inhibiting generation of apolipoprotein a (apo(a)) in vitro and/or in vivo; (viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure; (ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus; (x) prevention and/or treatment of critical illness, such as treatment of a critically ill patient, a critical illness poly-nephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness; (xi) prevention and/or treatment of polycystic ovary syndrome (PCOS); (xii) prevention and/or treatment of cerebral disease, such as cerebral ischemia, cerebral haemorrhage, and/or traumatic brain injury; (xiii) prevention and/or treatment of sleep apnoea; and/or (xiv) prevention and/or treatment of abuse, such as alcohol abuse and/or drug abuse.

In its fifth aspect the invention relates to methods for the preparation of such analogues and derivatives, which comprise the step of recombinantly producing a GLP-1 analogue having Trp at a position corresponding to position 8 of GLP-1(7-37) (SEQ ID NO: 1).

GLP-1 Receptor Agonist

A receptor agonist may be defined as an analogue that binds to a receptor and elicits a response typical of the natural ligand. A full agonist may be defined as one that elicits a response of the same magnitude as the natural ligand (see e.g. "Principles of Biochemistry", A L Lehninger, D L Nelson, M M Cox, Second Edition, Worth Publishers, 1993, page 763).

Thus, for example, a "GLP-1 receptor agonist" may be defined as a compound which is capable of binding to the GLP-1 receptor and capable of activating it. And a "full" GLP-1 receptor agonist may be defined as a GLP-1 receptor agonist which is capable of eliciting a magnitude of GLP-1 receptor response that is similar to native GLP-1.

In some embodiments the GLP-1 analogue of the invention is a GLP-1 receptor agonist. In some embodiments the GLP-1 analogue of the invention is a full GLP-1 receptor agonist. In some embodiments the GLP-1 derivative of the invention is a GLP-1 receptor agonist. In some embodiments the GLP-1 derivative of the invention is a full GLP-1 receptor agonist.

Structural Features

GLP-1 Analogues

The term "GLP-1 analogue" as used herein refers to an analogue (or variant) of the human glucagon-like peptide-1 (GLP-1(7-37)), the sequence of which is included in the sequence listing as SEQ ID NO: 1. The peptide having the sequence of SEQ ID NO: 1 may also be designated "native" GLP-1.

The GLP-1 analogue of the invention has a Trp at a position corresponding to position 8 of GLP-1(7-37) (SEQ ID NO: 1).

In some embodiments the GLP-1 analogue of the invention is an analogue of GLP-1(7-37) having from 30 to 36 amino acid residues. In some embodiments the GLP-1 analogue of the invention is fused to another protein, optionally via amino acid linkers. In some embodiments the other protein is an IgG-Fc protein.

The numbering of amino acid residues (such as "position 8") in the GLP-1 analogues of the invention follows the established practice in the art for native GLP-1, namely that the first (N-terminal) amino acid residue is numbered or accorded position no. 7, and the subsequent amino acid residues downstream towards the C-terminus are numbered 8, 9, 10, and so on, until the last (C-terminal) amino acid residue. In native GLP-1 the C-terminal amino acid residue is Gly, with number 37.

The numbering is done differently in the sequence listing, where the first amino acid residue of SEQ ID NO: 1 (His) is assigned no. 1, and the last (Gly) no. 31. However, herein we follow the established numbering practice in the art, as explained above.

In some embodiments of the $2^{nd}$ aspect of the present invention (the GLP-1 analogue of the invention) the GLP-1 analogue comprises (or is) a peptide of formula II (SEQ ID NO: 25): $Xaa_7$-Trp-Glu-Gly-Thr-$Xaa_2$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$-$Xaa_{42}$, wherein $Xaa_7$ is L-histidine, (S)-2-Hydroxy-3-(1H-imidazol-4-yl)-propionic acid, D-histidine, deamino-histidine, homohistidine, $N^\alpha$-acetyl-histidine, $N^\alpha$-formyl-histidine, $N^\alpha$-methyl-histidine, 3-pyridylalanine, 2-pyridylalanine, or 4-pyridylalanine; $Xaa_{12}$ is Phe or Leu; $Xaa_{16}$ is Val or Leu; $Xaa_{18}$ is Ser, Arg, Val, or Leu; $Xaa_{19}$ is Tyr or Gln; $Xaa_{20}$ is Leu or Met; $Xaa_{22}$ is Gly or Glu; $Xaa_{23}$ is Gln, Glu, or Arg; $Xaa_{25}$ is Ala or Val; $Xaa_{26}$ is Arg or Lys; $Xaa_{27}$ is Glu, Lys, or Leu; $Xaa_{30}$ is Ala, Glu, or Arg; $Xaa_{31}$ is Trp or His; $Xaa_{33}$ is Val; $Xaa_{34}$ is Arg, His, Asn, or Gln; $Xaa_{35}$ is Gly or Ala; $Xaa_{36}$ is Arg, Lys, or Gly; $Xaa_{37}$ is Gly, Lys, Pro, or absent; $Xaa_{38}$ is Ser, Gly, Ala, Glu, Pro, Lys, or absent; $Xaa_{39}$ is Ser, Gly, Ala, Glu, Pro, or absent; $Xaa_{40}$ is Ser, Gly, Ala, Glu, Pro, or absent; $Xaa_{41}$ is Ser, Gly, Ala, Glu, Pro, or absent; and $Xaa_{42}$ is Lys or absent; with the proviso that if one of $Xaa_{37}$, $Xaa_{38}$, $Xaa_{39}$, $Xaa_{40}$, $Xaa_{41}$, or $Xaa_{42}$ is absent then each subsequent amino acid residue is also absent, and with the proviso that at least one of $Xaa_{26}$, $Xaa_{27}$, $Xaa_{36}$, $Xaa_{37}$, $Xaa_{38}$, or $Xaa_{42}$ is Lys; or a pharmaceutically acceptable salt, amide, or ester thereof.

In some embodiments the GLP-1 analogue of the invention comprises (or is) the sequence of any one of formulas IIa, IIb, IIc, or IId, as defined in the section headed "Particular embodiments"; or a pharmaceutically acceptable salt, amide, or ester thereof. In some embodiments the GLP-1 analogue of the invention comprises, or is selected from, SEQ ID NO: 4, SEQ ID NO: 5, SEQ ID NO: 7, SEQ ID NO: 9, SEQ ID NO: 11, SEQ ID NO: 15, amino acids 1-275 of SEQ ID NO: 15, SEQ ID NO: 16, SEQ ID NO: 18, and SEQ ID NO: 20; or a pharmaceutically acceptable salt, amide, or ester thereof.

As it appears from the above formula II, the C-terminal amino acid may be $Xaa_{36}$, $Xaa_{37}$, $Xaa_{38}$, $Xaa_{39}$, $Xaa_{40}$, $Xaa_{41}$, or $Xaa_{42}$, i.e. have number 36, 37, 38, 39, 40, 41, or 42, respectively. GLP-1 analogues of the invention where the C-terminal amino acid $Xaa_{38}$ is present may be said to comprise an addition (or extension) of one amino acid, as compared to native GLP-1. Likewise, GLP-1 analogues of the invention where the C-terminal amino acid is $Xaa_{39}$ may be said to comprise an addition of two amino acids (namely $Xaa_{38}$ and $Xaa_{39}$), as compared to native GLP-1; and so forth.

Each of the GLP-1 analogues of the derivatives of the invention may be described by reference to i) the number of the amino acid residue in native GLP-1(7-37) which corresponds to the amino acid residue which is changed (i.e., the corresponding position in native GLP-1), and to ii) the actual change.

In other words, the GLP-1 analogue of the invention may be described by reference to the native GLP-1(7-37) peptide, namely as a variant thereof in which a number of amino acid residues have been changed when compared to native GLP-1(7-37) (SEQ ID NO: 1). These changes may represent, independently, one or more amino acid substitutions, additions, and/or deletions.

The following are non-limiting examples of suitable analogue nomenclature.

The GLP-1 analogue incorporated in the derivative of Example 1 herein may be referred to as (8W, 22E, 26R, 34R, 36K, 37K) GLP-1(7-37). When this Example 1 analogue is aligned with native GLP-1, the amino acid at the position in the analogue which corresponds, according to the alignment, to position 8 in native GLP-1 is W, the amino acid at the position in the analogue which corresponds to position 22 in native GLP-1 is E, the amino acid at the position in the analogue which corresponds to position 26 in native GLP-1 is R, the amino acid at the position in the analogue which corresponds to position 34 in native GLP-1 is R, the amino acid at the position in the analogue which corresponds to position 36 in native GLP-1 is K, and the amino acid at the position in the analogue which corresponds to position 37 in native GLP-1 is K. All other amino acids in this analogue are identical to the corresponding amino acid in native GLP-1.

As another example the GLP-1 analogue which is incorporated in the derivative of Example 3 herein may be referred to as (8W, 22E, 26R, 27K, 30E, 34R, 36K, 38E, 39G) GLP-1(7-37). When this Example 3 analogue is aligned with native GLP-1, the amino acid at the position in the analogue which corresponds, according to the alignment, to position 8 in native GLP-1 is W, the amino acid at the position in the analogue which corresponds to position 22 in native GLP-1 is E, the amino acid at the position in the analogue which corresponds to position 26 in native GLP-1 is R, the amino acid at the position in the analogue which corresponds to position 27 in native GLP-1 is K, the amino acid at the position in the analogue which corresponds to position 30 in native GLP-1 is E, the amino acid at the position in the analogue which corresponds to position 34 in native GLP-1 is R, the amino acid at the position in the analogue which corresponds to position 36 in native GLP-1 is K, and then the Example 3 analogue includes a C-terminal addition (or extension) of the dipeptide E-G, which for the present purposes is said to correspond to positions 38-39, respectively, in native GLP-1. Each of the other amino acids in this analogue is identical to the corresponding amino acid in native GLP-1.

The general formula II is to be understood in a similar manner.

Analogues "comprising" certain specified changes may comprise further changes, when compared to SEQ ID NO: 1. In a particular embodiment, the analogue "has" the specified changes, or "is" the specified analogue, in which cases there are no further changes, when compared to SEQ ID NO: 1.

As is apparent from above, amino acid residues may be identified by their full name, their one-letter code, and/or their three-letter code. These three ways are fully equivalent.

The expressions "a position equivalent to" or "corresponding position" is used herein to characterise the site of change in a variant GLP-1(7-37) sequence by reference to a reference sequence such as native GLP-1(7-37) (SEQ ID NO: 1). Equivalent or corresponding positions, as well as the number of changes, are easily deduced, e.g. by simple handwriting and visual inspection; and/or a standard protein or peptide alignment program may be used, such as "align" which is based on a Needleman-Wunsch algorithm. This algorithm is described in Needleman, S. B. and Wunsch, C. D., (1970), Journal of Molecular Biology, 48: 443-453, and the align program by Myers and W. Miller in "Optimal Alignments in Linear Space" CABIOS (computer applications in the biosciences) (1988) 4:11-17. For the alignment, the default scoring matrix BLOSUM62 and the default identity matrix may be used, and the penalty for the first residue in a gap may be set at −12, or preferably at −10, and the penalties for additional residues in a gap at −2, or preferably at −0.5.

An example of such alignment is inserted below of native GLP-1 of SEQ ID NO: 1, the analogue (8W, 22E, 26R, 27K, 30E, 34R, 36K, 38E, 39G) thereof of SEQ ID NO: 9:

```
Aligned_sequences:    2
1:                    SEQ_ID_NO_1
2:                    SEQ_ID_NO_9
Matrix:               EBLOSUM62
Gap_penalty:          10.0
Extend_penalty:       0.5

Length:               33

Identity:             24/33 (72.7%)

Similarity:           28/33 (84.8%)

Gaps:                 2/33  (6.1%)

Score:                128.0

SEQ_ID_NO_1   1    HAEGTFTSDVSSYLEGQAAKEFIAWLVKGRG--    31
                   |.||||||||||||.|||::||.|||:|:|
SEQ_ID_NO_9   1    HWEGTFTSDVSSYLEEQAARKFIEWLVRGKGEG    33
```

When 6 is added to the position numbers shown in this alignment (e.g. to "1" and "31" in sequence 1, and to "1" and "33" in sequence 2) one gets the position numbering as used herein. For example, in sequence 1 (which is identical to SEQ ID NO: 1), the N-terminal amino acid (H) has position number 7, and the C-terminal amino acid (G) has number 37. Regarding sequence 2, the N-terminal amino acid (H) has number 7 and the C-terminal amino acid (G) has number 39.

In case specific amino acid residues or the like with no one-letter codon (such as deamino-histidine (Imp) are included in the sequence these may, for alignment purposes, be replaced with, e.g., X. If desired, X can later be manually corrected.

The following are non-limiting examples of what can be inferred from the above alignment:

As one example it can be inferred that sequence 2 has 9 amino acid changes as compared to sequence 1 (namely at all those positions where a full stop("."), a colon (":"), or a horizontal hyphen ("-") is shown in the alignment).

As another example it can be inferred that, e.g., sequence no. 2 comprises 39G, since it has a G at the position which corresponds, according to the alignment, to position 39 in the reference sequence (sequence 1, SEQ ID NO: 1).

And similarly all other changes in sequence 2 as compared to sequence 1 can be deduced from the alignment.

In what follows, all amino acids of the GLP-1 analogue of the invention for which the optical isomer is not stated is to be understood to mean the L-isomer (unless otherwise specified).

Some additional embodiments of GLP-1 analogues of the invention, and for incorporation in the derivatives of the invention, are disclosed in the sections headed PARTICULAR EMBODIMENTS, ADDITIONAL PARTICULAR EMBODIMENTS, and STILL FURTHER PARTICULAR EMBODIMENTS.

GLP-1 Derivatives

The term "derivative" as used herein in the context of a GLP-1 analogue means a chemically modified GLP-1 analogue, in which one or more substituents have been covalently attached to the analogue.

In some embodiments the substituent may be referred to as a side chain.

The derivative of the invention comprises a GLP-1 analogue having a Trp at a position corresponding to position 8 of GLP-1(7-37) (SEQ ID NO: 1) and a substituent comprising at least eight consecutive —CH$_2$-groups and at least one functional group (FG) with a pKa<7 is attached to a Lys residue of the GLP-1 analogue.

In some embodiments the derivative comprises one or two such substituents.

In some embodiments the number of consecutive —CH$_2$-groups in the substituent is in the range of 8-20.

In some embodiments the functional group (FG) is selected from Chem. 1, Chem. 2, and Chem. 4:

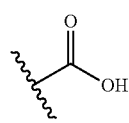

Chem. 1

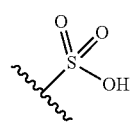

Chem. 2

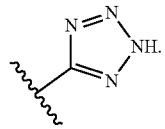

Chem. 4

In some embodiments pKa is the pH of a solution of CH$_3$-FG in water.

In some embodiments the invention, in its first aspect, relates to a derivative of formula I: (P-L)$_U$-B-GLP1, wherein GLP1 is a GLP-1 analogue having a Trp at a position corresponding to position 8 of GLP-1(7-37) (SEQ ID NO: 1), (P-L) is a substituent attached to a Lys residue of the GLP-1 analogue via an optional Branching group (B) and comprising a Protracting moiety (P) and a Linker (L), U represents the number of substituents (P-L) in the derivative and is 1 or 2; or a pharmaceutically acceptable salt, amide, or ester thereof.

In some embodiments the one or two substituents (P-L) each comprises a Protracting moiety (P) selected from Chem. 10, Chem. 11, Chem. 12, Chem. 13, and Chem. 14:

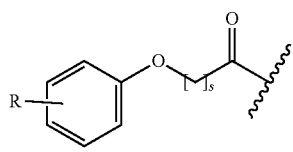

Chem. 10

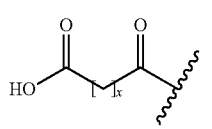

Chem. 11

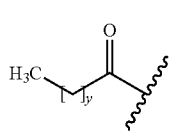

Chem. 12

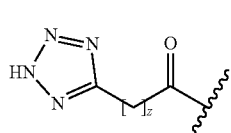

Chem. 13

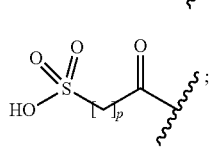

Chem. 14 and a Linker (L) comprising at least one linker element selected from Chem. 15, Chem. 16, Chem. 17, and Chem. 18:

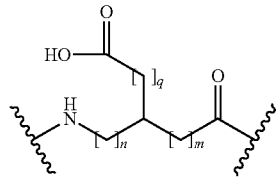

Chem. 15

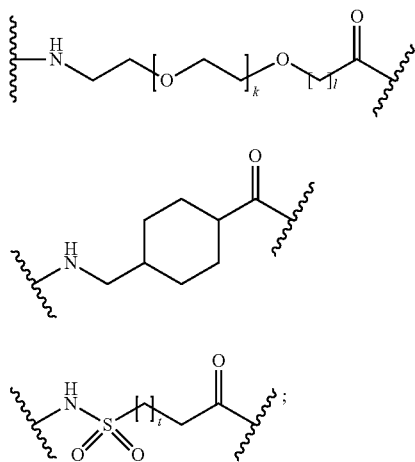

Chem. 16

Chem. 17

Chem. 18 wherein

R is —COOH;

each of s, x, y, z, and p independently represents an integer in the range of 8-20;

each of n, m, and q independently represents an integer in the range of 0-4; and each of k, l, and t independently represents an integer in the range of 1-5.

In some embodiments, the Branching group (B) comprises a Branched linker (BL) selected from Chem. 19 and Chem. 20:

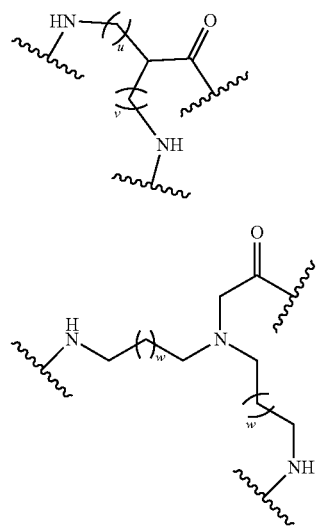

Chem. 19

Chem. 20 wherein u and v independently represents an integer in the range of 0-5, with the provisos that when u is 0 v is an integer in the range of 1-5, and when v is 0 u is an integer in the range of 1-5; and where each w represents an integer in the range of 0-2.

In some embodiments where u is 4 and v is 0 (or u is 0 and v is 4), the Branched linker of Chem. 20 may be referred to as a tri-radical of eps-Lys(Bis), of Chem. 19a:

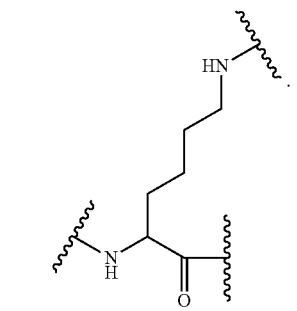

Chem. 19a

In some embodiments where w is 1, the Branched linker of Chem. 20 may be referred to as a tri-radical of Amino-C3-Gly(Bis).

In some embodiments (B absent, U=1) the derivative has formula Ia:

(P-L)-GLP1(such as the compound of Example 5).    Formula Ia:

In some embodiments (B absent, U=2) the derivative has formula Ib:

(P-L)$_2$-GLP1(such as the compound of Example 3).    Formula Ib:

In some embodiments (B present, U=2) the derivative has a "fork" structure of formula Ic or Id:

(P-L)$_2$>BL-PL-GLP1(such as the compound of Example 13)    Formula Ic:

(P-L)$_2$>BL-GLP1(such as the compound of Example 10);    Formula Id:

wherein P, L are defined above and B is represented by (BL-PL), wherein PL is an optional Pre linker (PL is present in formula Ic, PL is absent in formula Id), and BL is a Branched linker (embodiments of which are defined above), which provides the "fork" structure.

In some embodiments the GLP-1 analogue having a Trp at a position corresponding to position 8 of GLP-1(7-37) (SEQ ID NO: 1) is a GLP-1 analogue comprising formula II, as defined in the above section headed "GLP-1 analogues".

In some embodiments one or two of the following amino acid residues of the analogue of formula II is/are Lys: Xaa$_{26}$, Xaa$_{27}$, Xaa$_{36}$, Xaa$_{37}$, Xaa$_{38}$, and/or Xaa$_{42}$.

In some embodiments the derivative is a compound of any of Examples 1-5.

Some additional embodiments of derivatives of the invention are disclosed in the sections headed PARTICULAR EMBODIMENTS, ADDITIONAL PARTICULAR EMBODIMENTS, and STILL FURTHER PARTICULAR EMBODIMENTS.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivatives.

The concentration in plasma of the GLP-1 derivatives of the invention may be determined using any suitable method. For example, LC-MS (Liquid Chromatography Mass Spectroscopy) may be used, or immunoassays such as RIA (Radio Immuno Assay), ELISA (Enzyme-Linked Immuno Sorbent Assay), and LOCI (Luminescence Oxygen Channeling Immunoasssay). General protocols for suitable RIA and ELISA assays are found in, e.g., WO 2009/030738 on p. 116-118. A preferred assay is the LOCI assay, where LOCI refers to Luminescence Oxygen Channeling Immunoasssay, which is generally described for the determination of insulin by Poulsen and Jensen in Journal of Biomolecular Screening 2007, vol. 12, p. 240-247. The donor beads were coated with streptavidin, while acceptor beads were conjugated with a monoclonal antibody recognising a mid-/C-terminal epitope of the peptide. Another monoclonal antibody, specific for the N-terminus, was biotinylated. The three reactants were combined with the analyte and formed a two-sited immunocomplex. Illumination of the complex released singlet oxygen atoms from the donor beads, which were channeled into the acceptor beads and triggered chemiluminescence which was measured in an Envision plate reader. The amount of light was proportional to the concentration of the compound.

The GLP-1 derivatives and analogues of the invention have GLP-1 activity. This term refers to the ability to bind to the GLP-1 receptor and initiate a signal transduction pathway resulting in insulinotropic action or other physiological effects as is known in the art. For example, the analogues and derivatives of the invention can be tested for GLP-1 activity using the assays described in Examples 15 and 16 herein.

Pharmaceutically Acceptable Salt, Amide, or Ester

The derivatives and analogues of the invention may be in the form of a pharmaceutically acceptable salt, amide, or ester.

Salts are e.g. formed by a chemical reaction between a base and an acid, e.g.: $2NH_3 + H_2SO_4 \rightarrow (NH_4)_2SO_4$.

The salt may be a basic salt, an acid salt, or it may be neither nor (i.e. a neutral salt). Basic salts produce hydroxide ions and acid salts hydronium ions in water.

The salts of the derivative or analogue of the invention may be formed with added cations or anions between anionic or cationic groups, respectively. These groups may be situated in the peptide moiety, and/or in the side chain(s) of the derivative of the invention.

Non-limiting examples of anionic groups of the derivative or analogue of the invention include free carboxylic groups in the side chain, if any, as well as in the peptide moiety. The peptide moiety often includes a free carboxylic acid group at the C-terminus, and it may also include free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

The ester of the derivative or analogue of the invention may, e.g., be formed by the reaction of a free carboxylic acid group with an alcohol or a phenol, which leads to replacement of at least one hydroxyl group by an alkoxy or aryloxy group The ester formation may involve the free carboxylic group at the C-terminus of the peptide, and/or any free carboxylic group in the side chain.

The amide of the derivative or analogue of the invention may, e.g., be formed by the reaction of a free carboxylic acid group with an amine or a substituted amine, or by reaction of a free or substituted amino group with a carboxylic acid.

The amide formation may involve the free carboxylic group at the C-terminus of the peptide, any free carboxylic group in the side chain, the free amino group at the N-terminus of the peptide, and/or any free or substituted amino group of the peptide in the peptide and/or the side chain.

In some embodiments, the analogue or derivative of the invention is in the form of a pharmaceutically acceptable salt. In some embodiments, the analogue or derivative of the invention is in the form of a pharmaceutically acceptable amide. In some embodiments the analogue or derivative of the invention has an amide group at the C-terminus of the peptide. In some embodiments the analogue or derivative of the invention is in the form a pharmaceutically acceptable ester.

Functional Properties

In some embodiments the GLP-1 analogues and GLP-1 derivatives of the invention are stable against degradation by DPP-IV.

Also or alternatively, in some embodiments the GLP-1 analogues and GLP-1 derivatives of the invention have a good potency in vitro.

Also or alternatively, in some embodiments the GLP-1 analogues and GLP-1 derivatives of the invention have a good potency in vivo.

Also or alternatively, in some embodiments the GLP-1 analogues and GLP-1 derivatives of the invention bind well to the GLP-1 receptor.

Also or alternatively, in some embodiments they are GLP-1 receptor agonists.

DPP-IV Stability

As reported in the in vitro DPP-IV stability test of Example 14, the GLP-1 analogue of Example D (8W GLP-1(7-37)) demonstrated an impressive high stability against degradation by the DPP-IV enzyme, which was quite surprising and totally unexpected.

This observation is of course also relevant for the derivative of the invention which incorporates a GLP-1 analogue having a Trp at a position corresponding to position 8 of GLP-1(7-37) (SEQ ID NO: 1).

Biological Activity—Potency

In some embodiments the GLP-1 analogue of the invention is biologically active, or potent. In some embodiments the GLP-1 derivative of the invention is biologically active, or potent.

In some embodiments, potency and/or activity refers to in vitro potency, i.e. performance in a functional GLP-1 receptor assay, more in particular to the capability of activating the human GLP-1 receptor.

The in vitro potency may, e.g., be determined in a medium containing membranes expressing the human GLP-1 receptor, and/or in an assay with whole cells expressing the human GLP-1 receptor.

For example, the response of the human GLP-1 receptor may be measured in a reporter gene assay, e.g. in a stably transfected BHK cell line that expresses the human GLP-1 receptor and contains the DNA for the cAMP response element (CRE) coupled to a promoter and the gene for firefly luciferase (CRE luciferase). When cAMP is produced as a result of activation of the GLP-1 receptor this in turn results in the luciferase being expressed. Luciferase may be determined by adding luciferin, which by the enzyme is converted to oxyluciferin and produces bioluminescence, which is measured and is a measure of the in vitro potency. One non-limiting example of such an assay is described in Example 15.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the analogues and derivatives of the invention may be determined as described above, and the $EC_{50}$ determined. The lower the $EC_{50}$ value, the better the potency.

In some embodiments, the derivative or analogue of the invention has an in vitro potency corresponding to an $EC_{50}$ at or below 300 pM, determined using the method of Example 15.

In some embodiments the derivatives of the invention as well as the constituent GLP-1 analogues as such are potent in vivo, which may be determined as is known in the art in any suitable animal model, as well as in clinical trials. In some embodiments, potency in vivo may be determined using the PD study of Example 17 herein.

Some additional embodiments are disclosed in the sections headed PARTICULAR EMBODIMENTS, ADDITIONAL PARTICULAR EMBODIMENTS, and STILL FURTHER PARTICULAR EMBODIMENTS.

Biological Activity—In Vitro Receptor Binding

In some embodiments the GLP-1 analogue of the invention binds very well to the GLP-1 receptor. In some embodiments the GLP-1 derivative of the invention bind very well to the GLP-1 receptor. In some embodiments the GLP-1 receptor binding is determined at a low concentration of albumin, in some embodiments it is determined at a high concentration of albumin. This may be determined as described in Example 16.

In some embodiments the binding to the GLP-1 receptor at low albumin concentration is very good, corresponding to a low $IC_{50}$ value.

The $IC_{50}$ value at high albumin concentration reflects the influence of serum albumin on the binding to the GLP-1 receptor. Due to the side chain the GLP-1 derivative of the invention can bind to serum albumin and if this is the case then the $IC_{50}$ value at high serum albumin will be higher than the $IC_{50}$ value at low albumin. An increased $IC_{50}$ value at high serum albumin represents a reduced binding to the GLP-1 receptor caused by serum albumin binding competing with the binding to the GLP-1 receptor.

In some embodiments, the analogue or derivative of the invention binds very well to the GLP-1 receptor at a low albumin concentration. Also or alternatively, in some embodiments they bind very well at a high albumin concentration.

In some embodiments the GLP-1 receptor binding affinity ($IC_{50}$) of the analogue or derivative of the invention in the presence of 2.0% HSA (high albumin) is at 800 nM or below.

Some additional particular embodiments are disclosed in the sections headed PARTICULAR EMBODIMENTS, ADDITIONAL PARTICULAR EMBODIMENTS, and STILL FURTHER PARTICULAR EMBODIMENTS.

Pharmacokinetics Profile

In some embodiments the GLP-1 analogue of the invention has improved pharmacokinetic properties such as increased terminal half-life, and/or decreased clearance. In some embodiments the GLP-1 derivative of the invention has improved pharmacokinetic properties such as increased terminal half-life, and/or decreased clearance.

Increasing terminal half-life and/or decreasing of the clearance means that the compound in question is eliminated slower from the body. For the derivative or analogue of the invention this entails an extended duration of pharmacological effect.

The pharmacokinetic properties may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the compounds of the invention.

In such studies, animals are typically administered with a single dose of the drug, either intravenously (i.v.), subcutaneously (s.c.), or orally (p.o.) in a relevant formulation. Blood samples are drawn at predefined time points after dosing, and samples are analysed for concentration of drug with a relevant quantitative assay. Based on these measurements, time-plasma concentration profiles for the compound of study are plotted and a so-called non-compartmental pharmacokinetic analysis of the data is performed.

For most compounds, the terminal part of the plasma-concentration profiles will be linear when drawn in a semi-logarithmic plot, reflecting that after the initial absorption and distribution, drug is removed from the body at a constant fractional rate. The rate (lambda Z or $\lambda_z$) is equal to minus the slope of the terminal part of the plot. From this rate, also a terminal half-life may be calculated, as $t\frac{1}{2}=\ln(2)/\lambda_z$ (see, e.g., Johan Gabrielsson and Daniel Weiner: Pharmacokinetics and Pharmacodynamic Data Analysis. Concepts & Applications, 3rd Ed., Swedish Pharmaceutical Press, Stockholm (2000)).

Clearance can be determined after i.v. administration and is defined as the dose (D) divided by area under the curve (AUC) on the plasma concentration versus time profile (Rowland, M and Tozer T N: Clinical Pharmacokinetics: Concepts and Applications, $3^{rd}$ edition, 1995 Williams Wilkins).

The estimate of terminal half-life and/or clearance is relevant for evaluation of dosing regimens and an important parameter in drug development, in the evaluation of new drug compounds.

Production Processes

The production of peptides like GLP-1(7-37) and GLP-1 analogues is well known in the art.

The GLP-1 peptide moiety of the derivative of the invention (or fragments thereof) as well as the GLP-1 analogues of the invention may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

In some embodiments the entire GLP-1 analogue of the invention, or the entire GLP-1 analogue part of the derivative of the invention, is produced by recombinant methods, viz. by culturing a host cell containing a DNA sequence encoding the analogue and capable of expressing it in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines. In some embodiments such entirely recombinant fermentation step of the production process method is desirable, for instance due to production economy considerations.

In some embodiments where the GLP-1 analogue of the invention, or the GLP-1 analogue part of the derivative of the invention, includes non-coded amino acids, the analogue may be produced as known in the art, see e.g., Hodgson et al: "The synthesis of peptides and proteins containing non-natural amino acids", Chemical Society Reviews, vol. 33, no. 7 (2004), p. 422-430; and WO 2009/083549 A1 entitled "Semi-recombinant preparation of GLP-1 analogues".

Specific examples of methods of preparing a number of the derivatives of the invention are included in the experimental part.

Example 18 demonstrates the advantageous fully recombinant expression of a number of the analogues of the invention and compares expression yield with the expression yield in a known semi-recombinant method for known DPP-IV stabilised GLP-1 analogues which include one or more non-coded amino acids in their sequence.

Pharmaceutical Compositions

The invention also relates to pharmaceutical compositions comprising a derivative or an analogue of the invention, and a pharmaceutically acceptable excipient. Such compositions may be prepared as is known in the art.

The term "excipient" broadly refers to any component other than the active therapeutic ingredient(s). The excipient may be an inert substance, an inactive substance, and/or a not medicinally active substance.

The excipient may serve various purposes, e.g. as a carrier, vehicle, diluent, tablet aid, and/or to improve administration, and/or absorption of the active substance.

The formulation of pharmaceutically active ingredients with various excipients is known in the art, see e.g. Remington: The Science and Practice of Pharmacy (e.g. 19$^{th}$ edition (1995), and any later editions).

Non-limiting examples of excipients are: Solvents, diluents, buffers, preservatives, tonicity regulating agents, chelating agents, and stabilisers.

Examples of formulations include liquid formulations, i.e. aqueous formulations comprising water. A liquid formulation may be a solution, or a suspension. An aqueous formulation typically comprises at least 50% w/w water, or at least 60%, 70%, 80%, or even at least 90% w/w of water.

Alternatively, a pharmaceutical composition may be a solid formulation, e.g. a freeze-dried or spray-dried composition, which may be used as is, or whereto the physician or the patient adds solvents, and/or diluents prior to use.

The pH in an aqueous formulation may be anything between pH 3 and pH 10, for example from about 7.0 to about 9.5; or from about 3.0 to about 7.0, such as from 7.0 to 9.5, or from 3.0 to 7.0.

A pharmaceutical composition may comprise a buffer. The buffer may e.g. be selected from sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid, and mixtures thereof.

A pharmaceutical composition may comprise a preservative. The preservative may e.g. be selected from phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol), and mixtures thereof. The preservative may be present in a concentration from 0.1 mg/ml to 20 mg/ml. A pharmaceutical composition may comprise an isotonic agent. The isotonic agent may e.g. be selected from a salt (e.g. sodium chloride), a sugar or sugar alcohol, an amino acid (e.g. glycine, histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), and mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. Sugar alcohol is defined as a C4-C8 hydrocarbon having at least one —OH group and includes, for example, mannitol, sorbitol, inositol, galactitol, dulcitol, xylitol, and arabitol. In one embodiment, the sugar alcohol additive is mannitol.

A pharmaceutical composition may comprise a chelating agent. The chelating agent may e.g. be selected from salts of ethylenediaminetetraacetic acid (EDTA), citric acid, and aspartic acid, and mixtures thereof.

A pharmaceutical composition may comprise a stabiliser. The stabiliser may e.g. be one or more oxidation inhibitors, aggregation inhibitors, surfactants, and/or one or more protease inhibitors. Non-limiting examples of these various kinds of stabilisers are disclosed in the following.

The term "aggregate formation" refers to a physical interaction between the polypeptide molecules resulting in formation of oligomers, which may remain soluble, or large visible aggregates that precipitate from the solution. Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

A pharmaceutical composition may comprise an amount of an amino acid base sufficient to decrease aggregate formation of the polypeptide during storage of the composition. The term "amino acid base" refers to one or more amino acids (such as methionine, histidine, imidazole, arginine, lysine, isoleucine, aspartic acid, tryptophan, threonine), or analogues thereof. Any amino acid may be present either in its free base form or in its salt form. Any stereoisomer (i.e., L, D, or a mixture thereof) of the amino acid base may be present.

Methionine (or other sulphuric amino acids or amino acid analogous) may be added to inhibit oxidation of methionine residues to methionine sulfoxide when the polypeptide acting as the therapeutic agent is a polypeptide comprising at least one methionine residue susceptible to such oxidation. Any stereoisomer of methionine (L or D) or combinations thereof can be used.

A pharmaceutical composition may comprise a stabiliser selected from high molecular weight polymers or low molecular compounds. The stabiliser may e.g. be selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). A pharmaceutical composition may comprise additional stabilising agents such as, but not limited to, methionine and EDTA, which protect the polypeptide against methionine oxidation, and a nonionic surfactant, which protects the polypeptide against aggregation associated with freeze-thawing or mechanical shearing.

A pharmaceutical composition may comprise one or more surfactants. The term "surfactant" refers to any molecules or ions that are comprised of a water-soluble (hydrophilic) part, and a fat-soluble (lipophilic) part. The surfactant may e.g. be selected from anionic surfactants, cationic surfactants, nonionic surfactants, and/or zwitterionic surfactants.

A pharmaceutical composition may comprise one or more protease inhibitors, such as, e.g., EDTA (ethylenediamine tetraacetic acid), and/or benzamidineHCl.

Additional, optional, ingredients of a pharmaceutical composition include, e.g., wetting agents, emulsifiers, antioxidants, bulking agents, metal ions, oily vehicles, proteins (e.g., human serum albumin, gelatine), and/or a zwitterion (e.g., an amino acid such as betaine, taurine, arginine, glycine, lysine and histidine).

Still further, a pharmaceutical composition may be formulated as is known in the art of oral formulations of insulinotropic compounds, e.g. using any one or more of the formulations described in WO 2008/145728, WO 2012/080471, WO 2013/139694, and WO 2000/050012. In some embodiments a salt of a modified aliphatic amino acid such as sodium N-(8-(2-hydroxybenzoyl)amino)caprylate (SNAC) is used as a carrier to enhance absorption of the GLP-1 compound of the invention.

An administered dose may contain from 0.1 mg-100 mg of the derivative, from 1-100 mg of the derivative, or from 1-50 mg of the derivative.

The derivative or analogue may be administered in the form of a pharmaceutical composition. It may be administered to a patient in need thereof at several sites, for example, at topical sites such as skin or mucosal sites; at sites which bypass absorption such as in an artery, in a vein, or in the heart; and at sites which involve absorption, such as in the skin, under the skin, in a muscle, or in the abdomen.

The route of administration may be, for example, lingual; sublingual; buccal; in the mouth; oral; in the stomach; in the intestine; nasal; pulmonary, such as through the bronchioles, the alveoli, or a combination thereof; parenteral, epidermal; dermal; transdermal; conjunctival; uretal; vaginal; rectal; and/or ocular. A composition may be an oral composition, and the route of administration is per oral.

A composition may be administered in several dosage forms, for example as a solution; a suspension; an emulsion; a microemulsion; multiple emulsions; a foam; a salve; a paste; a plaster; an ointment; a tablet; a coated tablet; a chewing gum; a rinse; a capsule such as hard or soft gelatine capsules; a suppositorium; a rectal capsule; drops; a gel; a spray; a powder; an aerosol; an inhalant; eye drops; an ophthalmic ointment; an ophthalmic rinse; a vaginal pessary; a vaginal ring; a vaginal ointment; an injection solution; an in situ transforming solution such as in situ gelling, setting, precipitating, and in situ crystallisation; an infusion solution; or as an implant.

A composition may be a tablet, optionally coated, a capsule, or a chewing gum.

A composition may further be compounded in a drug carrier or drug delivery system, e.g. in order to improve stability, bioavailability, and/or solubility. In a particular embodiment a composition may be attached to such system through covalent, hydrophobic, and/or electrostatic interactions. The purpose of such compounding may be, e.g., to decrease adverse effects, achieve chronotherapy, and/or increase patient compliance.

A composition may also be used in the formulation of controlled, sustained, protracting, retarded, and/or slow release drug delivery systems.

Parenteral administration may be performed by subcutaneous, intramuscular, intraperitoneal, or intravenous injection by means of a syringe, optionally a pen-like syringe, or by means of an infusion pump.

A composition may be administered nasally in the form of a solution, a suspension, or a powder; or it may be administered pulmonally in the form of a liquid or powder spray.

Transdermal administration is a still further option, e.g. by needle-free injection, from a patch such as an iontophoretic patch, or via a transmucosal route, e.g. buccally.

A composition may be a stabilised formulation. The term "stabilised formulation" refers to a formulation with increased physical and/or chemical stability, preferably both.

In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

The treatment with a derivative or analogue according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon agonists, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogs), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonists, Y2 receptor agonists, Y4 receptor agonits, mixed Y2/Y4 receptor agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, oxyntomodulin and analogues, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, fibroblast growth factor 21 (FGF-21), galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogs), gastrin and gastrin analogs.

The treatment with a derivative or analogue according to this invention may also be combined with a surgery that influences the glucose levels, and/or lipid homeostasis such as gastric banding or gastric bypass.

Pharmaceutical Indications

The present invention also relates to a derivative or analogue of the invention, for use as a medicament.

In some embodiments, the derivative or analogue of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

In some embodiments the indication is selected from the group consisting of (i)-(xiv), such as indications (i)-(viii), (x)-(xiii), and/or (xiv), and relates in one way or the other to diabetes.

In some embodiments, the indication is selected from the group consisting of (i)-(iii) and (v)-(viii), such as indications (i), (ii), and/or (iii); or indication (v), indication (vi), indication (vii), and/or indication (viii).

In some embodiments, the indication is (i). In a further particular embodiment the indication is (v). In a still further particular embodiment the indication is (viii).

In some embodiments the derivative or analogue of the invention may be used in the treatment and/or prevention of all forms of diabetes including eating disorders, cardiovascular diseases, gastrointestinal diseases, diabetic complications, and/or polycystic ovary syndrome; and/or for improving lipid parameters, improving β-cell function, and/or for delaying or preventing diabetic disease progression.

The following indications are particularly preferred: Type 2 diabetes, and/or obesity.

In some embodiments the invention relates to a method for weight management.

In some embodiments the invention relates to a method for reduction of appetite.

In some embodiments the invention relates to a method for reduction of food intake.

Generally, all subjects suffering from obesity are also considered to be suffering from overweight. In some embodiments the invention relates to a method for treatment or prevention of obesity. In some embodiments the invention relates to use of the derivative or analogue of the invention for treatment or prevention of obesity. In some embodiments the subject suffering from obesity is human, such as an adult human or a paediatric human (including infants, children, and adolescents). Body mass index (BMI) is a measure of body fat based on height and weight. The formula for calculation is BMI=weight in kilograms/(height in meters)$^2$. A human subject suffering from obesity may have a BMI of ≥30; this subject may also be referred to as obese. In some embodiments the human subject suffering from obesity may have a BMI of ≥35 or a BMI in the range of ≥30 to <40. In some embodiments the obesity is severe obesity or morbid obesity, wherein the human subject may have a BMI of ≥40.

In some embodiments the invention relates to a method for treatment or prevention of overweight, optionally in the presence of at least one weight-related comorbidity. In some embodiments the invention relates to use of the derivative or analogue of the invention for treatment or prevention of overweight, optionally in the presence of at least one weight-related comorbidity. In some embodiments the subject suffering from overweight is human, such as an adult human or a paediatric human (including infants, children, and adolescents). In some embodiments a human subject suffering from overweight may have a BMI of ≥25, such as a BMI of ≥27. In some embodiments a human subject suffering from overweight has a BMI in the range of 25 to <30 or in the range of 27 to <30. In some embodiments the weight-related comorbidity is selected from the group consisting of hypertension, diabetes (such as type 2 diabetes), dyslipidaemia, high cholesterol, and obstructive sleep apnoea.

In some embodiments the invention relates to a method for reduction of body weight. In some embodiments the invention relates to use of the derivative or analogue of the invention for reduction of body weight. A human to be subjected to reduction of body weight according to the present invention may have a BMI of ≥25, such as a BMI of ≥27 or a BMI of ≥30. In some embodiments the human to be subjected to reduction of body weight according to the present invention may have a BMI of ≥35 or a BMI of ≥40. The term "reduction of body weight" may include treatment or prevention of obesity and/or overweight.

Particular Embodiments

The following are particular embodiments of the invention:
1. A derivative comprising a GLP-1 analogue having a Trp at a position corresponding to position 8 of GLP-1(7-37) (SEQ ID NO: 1) and wherein a substituent comprising at least eight consecutive —CH$_2$-groups and at least one functional group (FG) with a pKa<7 is attached to a Lys residue of the GLP-1 analogue.
2. The derivative of any of embodiments 1-2, which comprises one or two substituents attached to one or two Lys residues of the GLP-1 analogue.
3. The derivative of embodiment 1, wherein the substituent(s) is (are) attached to the epsilon amino group of the Lys residue(s).
4. The derivative of any of embodiments 1-3, wherein the number of consecutive —CH$_2$-groups in the substituent(s) is in the range of 8-20.

5. The derivative of embodiment 4, wherein the number is in the range of 9-18.
6. The derivative of any of embodiments 4-5, wherein the number is 9, 10, 12, 14, 15, 16, or 18.
7. The derivative of any of embodiments 1-6, wherein the at least one FG is independently selected from Chem. 1, Chem. 2, and Chem. 4:

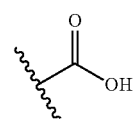

Chem. 1

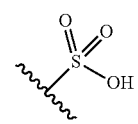

Chem. 2

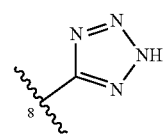

Chem. 4 or a pharmaceutically acceptable salt, amide, or ester thereof.
8. The derivative of any of embodiments 1-7, wherein the number, in each of the one or two substituents, of FG's with a pKa<7 is in the range of 1-10.
9. The derivative of embodiment 8, wherein the number is in the range of 1-8.
10. The derivative of any of embodiments 8-9, wherein the number is in the range of 1-6.
11. The derivative of any of embodiments 8-10, wherein the number is in the range of 1-4.
12. The derivative of any of embodiments 8-11, wherein the number is 1 or 2.
13. The derivative of any of embodiments 1-12, wherein pKa is the pH of a solution of CH$_3$-FG in water.
14. The derivative of any of embodiments 1-13, wherein pKa is minus log Ka for the equilibrium of Equation 1:

$$CH_3\text{-}FG+H_2O \Leftrightarrow OFG^- + H_3O^+. \quad \text{Equation 1:}$$

15. The derivative of any of embodiments 1-14, wherein the GLP-1 analogue comprises a peptide of formula II (SEQ ID NO: 25):

Xaa$_7$-Trp-Glu-Gly-Thr-Xaa$_{12}$-Thr-Ser-Asp-Xaa$_{16}$-Ser-Xaa$_{18}$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$, wherein Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;

Xaa$_{12}$ is Phe or Leu;
Xaa$_{16}$ is Val or Leu;
Xaa$_{18}$ is Ser, Arg, Val, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;

Xaa$_{26}$ is Arg or Lys;
Xaa$_{27}$ is Glu, Lys, or Leu;
Xaa$_{30}$ is Ala, Glu, or Arg;
Xaa$_{31}$ is Trp or His;
Xaa$_{33}$ is Val;
Xaa$_{34}$ is Arg, His, Asn, or Gln;
Xaa$_{35}$ is Gly or Ala;
Xaa$_{36}$ is Arg, Lys, or Gly;
Xaa$_{37}$ is Gly, Lys, Pro, or absent;
Xaa$_{38}$ is Ser, Gly, Ala, Glu, Pro, Lys, or absent;
Xaa$_{39}$ is Ser, Gly, Ala, Glu, Pro, or absent;
Xaa$_{40}$ is Ser, Gly, Ala, Glu, Pro, or absent;
Xaa$_{41}$ is Ser, Gly, Ala, Glu, Pro, or absent; and
Xaa$_{42}$ is Lys or absent;
with the proviso that at least one of Xaa$_{26}$, Xaa$_{27}$, Xaa$_{36}$, Xaa$_{37}$, Xaa$_{38}$, or Xaa$_{42}$ is Lys;
or a pharmaceutically acceptable salt, amide, or ester thereof.

15a. The derivative of embodiment 15, wherein Xaa$_7$ is L-histidine.

16. The derivative of any of embodiments 15-15a, wherein Xaa$_7$ is L-histidine; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Gly or Glu; Xaa$_{23}$ is Gln; Xaa$_{25}$ is Ala; Xaa$_{26}$ is Arg or Lys; Xaa$_{27}$ is Glu or Lys; Xaa$_{30}$ is Ala or Glu; Xaa$_{31}$ is Trp; Xaa$_{33}$ is Val; Xaa$_{34}$ is Arg; Xaa$_{35}$ is Gly; Xaa$_{36}$ is Arg or Lys; Xaa$_{37}$ is Gly, Lys, or Pro; Xaa$_{38}$ is Glu, Lys, or absent; Xaa$_{39}$ is Gly or absent; Xaa$_{40}$ is Gly or absent; Xaa$_{41}$ is Ser or absent; and Xaa$_{42}$ is Lys or absent.

17. The derivative of any of embodiments 15-16, wherein the GLP-1 analogue is a peptide of formula II.

18. The derivative of any of embodiments 15-17, wherein if Xaa$_{37}$ is absent then each of Xaa$_{38}$, Xaa$_{39}$, Xaa$_{40}$, Xaa$_{41}$, and Xaa$_{42}$ is also absent.

18a. The derivative of any of embodiments 15-18, wherein if Xaa$_{38}$ is absent then each of Xaa$_{39}$, Xaa$_{40}$, Xaa$_{41}$, and Xaa$_{42}$ is also absent.

19. The derivative of any of embodiments 15-18a, wherein if Xaa$_{39}$ is absent then each of Xaa$_{40}$, Xaa$_{41}$, and Xaa$_{42}$ is also absent.

20. The derivative of any of embodiments 15-19, wherein if Xaa$_{40}$ is absent then each of Xaa$_{41}$ and Xaa$_{42}$ is also absent.

21. The derivative of any of embodiments 15-20, wherein if Xaa$_{41}$ is absent then Xaa$_{42}$ is also absent.

22. The derivative of any of embodiments 15-21, wherein if one of Xaa$_{38}$, Xaa$_{39}$, Xaa$_{40}$, Xaa$_{41}$, or Xaa$_{42}$ is absent then each subsequent amino acid residue is also absent.

23. The derivative of any of embodiments 15-22 wherein one or two of Xaa$_{26}$, Xaa$_{27}$, Xaa$_{36}$, Xaa$_{37}$, Xaa$_{38}$, or Xaa$_{42}$ is/are Lys.

23a. The derivative of embodiment 23 wherein the one or two substituents is/are attached to the epsilon amino group of one or two Lys residues of the analogue.

23b. The derivative of any of embodiments 1-23a, wherein the GLP-1 analogue is selected from SEQ ID NO: 5, SEQ ID NO: 7, SEQ ID NO: 9, SEQ ID NO: 11, amino acids 1-275 of SEQ ID NO: 15, SEQ ID NO:16, SEQ ID NO: 18, and SEQ ID NO: 20; or a pharmaceutically acceptable salt, amide, or ester thereof.

23c. The derivative of any of embodiments 1-23b, wherein the GLP-1 analogue is selected from SEQ ID NO: 5, SEQ ID NO: 7, SEQ ID NO: 9, SEQ ID NO: 11, SEQ ID NO:16, SEQ ID NO: 18, and SEQ ID NO: 20; or a pharmaceutically acceptable salt, amide or ester thereof.

24. A derivative of formula I:

(P-L)$_U$-B-GLP1, wherein GLP1 is a GLP-1 analogue having a Trp at a position corresponding to position 8 of GLP-1(7-37) (SEQ ID NO: 1), (P-L) is a substituent attached to a Lys residue of the GLP-1 analogue via an optional Branching group (B) and comprising a Protracting moiety (P) and a Linker (L), U represents the number of substituents (P-L) in the derivative and is 1 or 2;
or a pharmaceutically acceptable salt, amide, or ester thereof.

24a. The derivative of embodiment 24 which comprises at least one functional group (FG) with a pKa<7.

24b. The derivative of embodiment 24a, wherein the at least one functional group is independently selected from Chem. 1, Chem. 2, and Chem. 4.

25. The derivative of any of embodiments 24-24b which is a derivative according to any of embodiments 1-23c.

26. The derivative of any of embodiments 24-25, which comprises one or two substituents (P-L) attached to one or two Lys residues of the GLP-1 analogue. 26. The derivative of any of embodiments 24-25, wherein the GLP-1 analogue is defined as in any of embodiments 15-23c.

27. The derivative of any of embodiments 24-26, wherein the (each) substituent (P-L) comprises a Protracting moiety (P) selected from Chem. 10, Chem. 11, Chem. 12, Chem. 13, and Chem. 14:

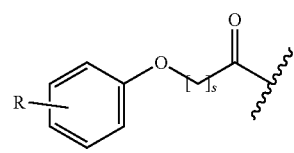

Chem. 10

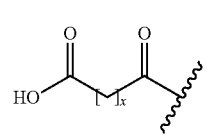

Chem. 11

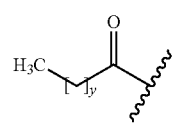

Chem. 12

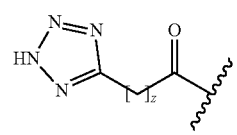

Chem. 13

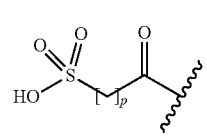

Chem. 14 and a Linker (L) comprising at least one linker element selected from Chem. 15, Chem. 16, Chem. 17, and Chem. 18:

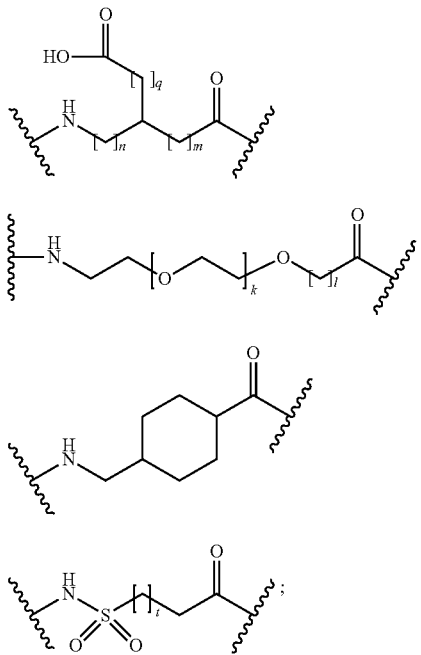

Chem. 15

Chem. 16

Chem. 17

Chem. 18 wherein
R is —COOH;
each of s, x, y, z, and p independently represents an integer in the range of 8-20;
each of n, m, and q independently represents an integer in the range of 0-4; and
each of k, l, and t independently represents an integer in the range of 1-5.

28. The derivative of embodiment 27, wherein at least one linker element means a number of linker elements in the (each) substituent (P-L) in the range of 1-10.

29. The derivative of any of embodiments 27-28 which contains from 1 to 8 linker elements in the (each) substituent (P-L).

30. The derivative of any of embodiments 24-29, wherein the (each) substituent (P-L) consists of a Protracting moiety (P) and a linker (L).

31. The derivative of any of embodiments 24-30, wherein P is Chem. 10.

32. The derivative of any of embodiments 24-31, wherein R is at position 3 of the benzene ring (m).

33. The derivative of any of embodiments 24-31, wherein R is at position 4 of the benzene ring (p).

34. The derivative of any of embodiments 24-33, wherein s is 8-20.

35. The derivative of any of embodiments 24-34, wherein s is 8-10.

36. The derivative of any of embodiments 24-35 wherein s is 9 or 10.

36a. The derivative of any of embodiments 24-36, wherein s is 9.

36b. The derivative of any of embodiments 24-36, wherein s is 10.

37. The derivative of any of embodiments 24-30, wherein P is Chem. 11.

38. The derivative of any of embodiments 24-30 and 37, wherein x is 8-20.

39. The derivative of any of embodiments 24-30 and 37-38, wherein x is 12-20.

40. The derivative of any of embodiments 24-30 and 37-39, wherein x is 12.

41. The derivative of any of embodiments 24-30 and 37-39, wherein x is 16.

42. The derivative of any of embodiments 24-30 and 37-39, wherein x is 18.

43. The derivative of any of embodiments 24-30, wherein P is Chem. 12.

44. The derivative of any of embodiments 24-30 and 43, wherein y is 8-20.

45. The derivative of any of embodiments 24-30 and 43-44, wherein y is 12-20.

46. The derivative of any of embodiments 24-30 and 43-45, wherein y is 14.

47. The derivative of any of embodiments 24-30, wherein P is Chem. 13.

48. The derivative of any of embodiments 24-30 and 47, wherein z is 8-20.

49. The derivative of any of embodiments 24-30 and 47-48, wherein z is 13-17.

50. The derivative of any of embodiments 24-30 and 47-49, wherein z is 15.

51. The derivative of any of embodiments 24-30, wherein P is Chem. 14.

52. The derivative of any of embodiments 24-30 and 51, wherein p is 8-20.

53. The derivative of any of embodiments 24-30 and 51-53, wherein p is 13-17.

54. The derivative of any of embodiments 24-30 and 51-53, wherein p is 15.

55. The derivative of any of embodiments 24-54, wherein L comprises linker element Chem. 15.

56. The derivative of any of embodiments 24-55, wherein each of n, m, and q, independently, is 0-4.

57. The derivative of any of embodiments 24-56, wherein n is 0, m is 2, and q is 1.

57a. The derivative of any of embodiments 55-56, wherein the Chem. 15 linker element is in the L-form.

58. The derivative of any of embodiments 24-57a, wherein L comprises from 0 to 6 times of linker element Chem. 16.

59. The derivative of any of embodiments 24-58, wherein each of k and l, independently, is 1-5.

60. The derivative of any of embodiments 24-59, wherein each of k and l is 1.

61. The derivative of any of embodiments 58-60, wherein L comprises 0 times Chem. 16, viz. does not comprise Chem. 16.

62. The derivative of any of embodiments 58-60, wherein L comprises 2 times Chem. 16.

63. The derivative of any of embodiments 58-60, wherein L comprises 4 times Chem. 16.

64. The derivative of any of embodiments 58-60, wherein L comprises 6 times Chem. 16.

65. The derivative of any of embodiments 24-64, wherein L comprises linker element Chem. 17.

66. The derivative of any of embodiments 24-65, wherein L comprises linker element Chem. 18.

67. The derivative of any of embodiments 24-66, wherein t is 1-5.

68. The derivative of any of embodiments 24-67, wherein t is 2.

69. The derivative of any of embodiments 24-68, wherein if there is more than one linker element the linker elements are interconnected via amide bonds.
70. The derivative of embodiment 69, wherein the more than one interconnected linker elements constitute the linker, L.
71. The derivative of embodiment 69, wherein the sole linker element constitutes the linker, L.
72. The derivative of any of embodiments 70-71, wherein the (each) linker (L) and the (each) protracting moiety (P) are interconnected by an amide bond.
73. The derivative of any of embodiments 70-72, wherein the (each) linker (L) is connected by an amide bond to the epsilon amino group of the (each) Lys residue, optionally via the Branching group (B).
74. The derivative of any of embodiments 24-73, wherein the Branching group (B) comprises a Branched linker (BL) selected from Chem. 19 and Chem. 20:

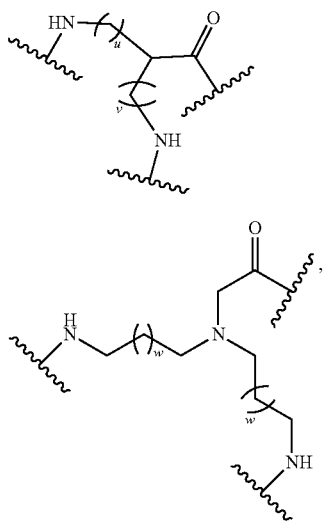

Chem. 19

Chem. 20 wherein u and v independently represents an integer in the range of 0-5, with the provisos that when u is 0 v is an integer in the range of 1-5, and when v is 0 u is an integer in the range of 1-5; and where each w represents an integer in the range of 0-2.
75. The derivative of embodiment 74, wherein BL is Chem. 19.
76. The derivative of any of embodiments 74-75, wherein u and v independently represents an integer in the range of 0-5, with the provisos that when u is 0 v is 1-5, and when v is 0 u is 1-5.
77. The derivative of any of embodiments 74-76, wherein u is 0 and v is 4.
78. The derivative of any of embodiments 74-76, wherein u is 4 and v is 0.
79. The derivative of embodiment 74, wherein BL is Chem. 20.
80. The derivative of any of embodiments 74 and 79, wherein w is 0-2.
81. The derivative of any of embodiments 74 and 79-80, wherein w is 1.
82. The derivative of any of embodiments 24-81, wherein B is absent and U is 1.
83. The derivative of any of embodiments 24-82, which has formula Ia: (P-L)-GLP1; or a pharmaceutically acceptable salt, amide, or ester thereof.

84. The derivative of any of embodiments 82-84, wherein P is selected from Chem. 11 and Chem. 12.
85. The derivative of embodiment 84, wherein P is Chem. 11.
86. The derivative of embodiment 85, wherein x is 16.
87. The derivative of embodiment 84, wherein P is Chem. 12.
88. The derivative of embodiment 87, wherein y is 14.
89. The derivative of any of embodiments 82-88, wherein L comprises linker element Chem. 15.
90. The derivative of any of embodiments 82-89, wherein L comprises linker element Chem. 15, wherein q is 1, m is 2, and n is 0.
91. The derivative of embodiment 90, wherein L consists of the linker element Chem. 15, wherein q is 1, m is 2, and n is 0.
92. The derivative of any of embodiments 82-90, wherein L comprises linker element Chem. 16.
93. The derivative of any of embodiments 82-90 and 92, wherein L comprises two linker elements Chem. 16.
94. The derivative of any of embodiments 92-93, wherein k=l=1.
95. The derivative of any of embodiments 82-90 and 92-94, wherein L consists of one linker element Chem. 15 wherein q is 1 m is 2 and n is 0; and two linker elements Chem. 16 wherein k is 1 and l is 1 (Chem. 15-2×Chem. 16) interconnected via amide bonds and in the sequence indicated.
96. The derivative of any of embodiments 82-95, wherein GLP1 comprises a peptide of formula Ha (SEQ ID NO: 26):
    Xaa$_7$-Trp-Glu-Gly-Thr-Xaa$_{12}$-Thr-Ser-Asp-Xaa$_6$-Ser-Xaa$_8$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_3$-Xaa$_{36}$-Xaa$_{37}$,
    wherein
    Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;
    Xaa$_{12}$ is Phe or Leu;
    Xaa$_{16}$ is Val or Leu;
    Xaa$_{18}$ is Ser, Arg, Val, or Leu;
    Xaa$_{19}$ is Tyr or Gln;
    Xaa$_{20}$ is Leu or Met;
    Xaa$_{22}$ is Gly or Glu;
    Xaa$_{23}$ is Gln, Glu, or Arg;
    Xaa$_{25}$ is Ala or Val;
    Xaa$_{26}$ is Arg or Lys;
    Xaa$_{27}$ is Glu, Lys, or Leu;
    Xaa$_{30}$ is Ala, Glu, or Arg;
    Xaa$_{31}$ is Trp or His;
    Xaa$_{33}$ is Val;
    Xaa$_{34}$ is Arg, His, Asn, or Gln;
    Xaa$_{35}$ is Gly or Ala;
    Xaa$_{36}$ is Arg, Lys, or Gly; and
    Xaa$_{37}$ is Gly, Lys, Pro, or absent;
    with the proviso that at least one of Xaa$_{26}$, Xaa$_{27}$, Xaa$_{36}$, or Xaa$_{37}$ is Lys; or a pharmaceutically acceptable salt, amide, or ester thereof.
96a. The derivative of embodiment 96, wherein Xaa$_7$ is L-histidine.
97. The derivative of any of embodiments 96-96a, wherein Xaa$_7$ is L-histidine; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Gly; Xaa$_{23}$ is Gln; Xaa$_{25}$ is Ala; Xaa$_{26}$ is Lys; Xaa$_{27}$ is Glu; Xaa$_{30}$ is Ala; Xaa$_{31}$ is Trp; Xaa$_{33}$ is Val; Xaa$_{34}$ is Arg; Xaa$_{35}$ is Gly; Xaa$_{36}$ is Arg; and Xaa$_{37}$ is Gly.

98. The derivative of any of embodiments 96-97, wherein GLP-1 is a peptide of formula IIa.
99. The derivative of any of embodiments 82-98, wherein (P-L) is attached to Lys26.
100. The derivative of any of embodiments 24-81, wherein B is absent and U is 2.
101. The derivative of any of embodiments 24-81 and 100, which has formula Ib: (P-L)$_2$-GLP1; or a pharmaceutically acceptable salt, amide, or ester thereof.
102. The derivative of any of embodiments 100-101, wherein each P is selected, independently, from Chem. 10 and Chem. 11.
103. The derivative of any of embodiment 102, wherein the two P are identical.
104. The derivative of embodiment 103, wherein P is Chem. 10.
105. The derivative of embodiment 104, wherein R is —COOH.
106. The derivative of any of embodiments 104-105, wherein R is at position 3 of the benzene ring (m).
107. The derivative of any of embodiments 104-105, wherein R is at position 4 of the benzene ring (p).
108. The derivative any of embodiments 104-107 wherein s is 9 or 10.
108a. The derivative any of embodiments 104-107 wherein s is 9.
108b. The derivative any of embodiments 104-107 wherein s is 10.
109. The derivative of embodiment 103, wherein P is Chem. 11.
110. The derivative of embodiment 109, wherein x is 18.
110a. The derivative of embodiment 109, wherein x is 12.
111. The derivative of any of embodiments 100-110a, wherein each L comprises linker element Chem. 15.
112. The derivative of embodiment 111, wherein each L comprises linker element Chem. 15, wherein q is 1, m is 2, and n is 0.
113. The derivative of any of embodiments 100-112, wherein each L comprises linker element Chem. 16.
114. The derivative of embodiment 113, wherein each L comprises two linker elements Chem. 16.
115. The derivative of any of embodiments 113-114, wherein k=l=1.
116. The derivative of any of embodiments 100-115, wherein each L comprises linker element Chem. 17.
116. The derivative of any of embodiments 100-115, wherein each L consists of one linker element Chem. 15 wherein q is 1 m is 2 and n is 0; and two linker elements Chem. 16 wherein k is 1 and l is 1 (Chem. 15-2×Chem. 16) interconnected via amide bonds and in the sequence indicated.
117. The derivative of any of embodiments 100-115, wherein each L consists of one linker element Chem. 15 wherein q is 1 m is 2 and n is 0; and four linker elements Chem. 16 wherein k is 1 and l is 1 (Chem. 15-4×Chem. 16) interconnected via amide bonds and in the sequence indicated.
116. The derivative of any of embodiments 100-115, wherein each L consists of one linker element Chem. 17, one linker element Chem. 15 wherein q is 1 m is 2 and n is 0; and two linker elements Chem. 16 wherein k is 1 and l is 1 (Chem. 17-Chem. 15-2×Chem. 16) interconnected via amide bonds and in the sequence indicated.
117. The derivative of any of embodiments 100-116, wherein GLP-1 comprises a peptide of formula IIb (SEQ ID NO: 27):

Xaa$_7$-Trp-Glu-Gly-Thr-Xaa$_{12}$-Thr-Ser-Asp-Xaa$_6$-Ser-Xaa$_8$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$,
wherein
Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;
Xaa$_{12}$ is Phe or Leu;
Xaa$_{16}$ is Val or Leu;
Xaa$_{18}$ is Ser, Arg, Val, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg or Lys;
Xaa$_{27}$ is Glu, Lys, or Leu;
Xaa$_{30}$ is Ala, Glu, or Arg;
Xaa$_{31}$ is Trp or His;
Xaa$_{33}$ is Val;
Xaa$_{34}$ is Arg, His, Asn, or Gln;
Xaa$_{35}$ is Gly or Ala;
Xaa$_{36}$ is Arg, Lys, or Gly;
Xaa$_{37}$ is Gly, Lys, Pro, or absent;
Xaa$_{38}$ is Ser, Gly, Ala, Glu, Pro, Lys, or absent; and
Xaa$_{39}$ is Ser, Gly, Ala, Glu, Pro, or absent;
with the proviso that at least two of Xaa$_{26}$, Xaa$_{27}$, Xaa$_{36}$, Xaa$_{37}$, or Xaa$_{38}$ is Lys; or a pharmaceutically acceptable salt, amide, or ester thereof.
117a. The derivative of embodiment 117, wherein Xaa$_7$ is L-histidine.
118. The derivative of any of embodiments 117-117a, wherein Xaa$_7$ is L-histidine; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Glu; Xaa$_{23}$ is Gln; Xaa$_{25}$ is Ala; Xaa$_{26}$ is Lys or Arg; Xaa$_{27}$ is Glu or Lys; Xaa$_{30}$ is Ala or Glu; Xaa$_{31}$ is Trp; Xaa$_{33}$ is Val; Xaa$_{34}$ is Arg; Xaa$_{35}$ is Gly; Xaa$_{36}$ is Lys; Xaa$_{37}$ is Gly or Lys; Xaa$_{38}$ is Glu or absent; and Xaa$_{39}$ is Gly or absent; with the proviso that at least two of Xaa$_{26}$, Xaa$_{27}$, Xaa$_{36}$, and Xaa$_{37}$ is Lys.
119. The derivative of any of embodiments 117-118, wherein GLP-1 is a peptide of formula IIb.
120. The derivative of any of embodiments 100-119, wherein the two (P-L) is attached to i) Lys26 and Lys37; ii) Lys27 and Lys36; or iii) Lys36 and Lys37.
121. The derivative of any of embodiments 100-116, wherein GLP-1 comprises a peptide of formula IIc (SEQ ID NO: 28):

Xaa$_7$-Trp-Glu-Gly-Thr-Xaa$_{12}$-Thr-Ser-Asp-Xaa$_6$-Ser-Xaa$_8$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$,
wherein
Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;
Xaa$_{12}$ is Phe or Leu;
Xaa$_{16}$ is Val or Leu;
Xaa$_{18}$ is Ser, Arg, Val, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;

Xaa$_{25}$ is Ala or Val;
Xaa$_{26}$ is Arg or Lys;
Xaa$_{27}$ is Glu, Lys, or Leu;
Xaa$_{30}$ is Ala, Glu, or Arg;
Xaa$_{31}$ is Trp or His;
Xaa$_{33}$ is Val;
Xaa$_{34}$ is Arg, His, Asn, or Gln;
Xaa$_{35}$ is Gly or Ala;
Xaa$_{36}$ is Arg, Lys, or Gly;
Xaa$_{37}$ is Gly, Lys, Pro, or absent;
Xaa$_{38}$ is Ser, Gly, Ala, Glu, Pro, or Lys;
Xaa$_{39}$ is Ser, Gly, Ala, Glu, or Pro;
Xaa$_{40}$ is Ser, Gly, Ala, Glu, or Pro;
Xaa$_{41}$ is Ser, Gly, Ala, Glu, or Pro; and
Xaa$_{42}$ is Lys;
with the proviso that at least two of Xaa$_{26}$, Xaa$_{27}$, Xaa$_{36}$, Xaa$_{37}$, Xaa$_{38}$, or Xaa$_{42}$ are Lys;
or a pharmaceutically acceptable salt, amide, or ester thereof.

121a. The derivative of embodiment 121, wherein Xaa$_7$ is L-histidine.

122. The derivative of any of embodiments 121-121a, wherein Xaa$_7$ is L-histidine; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Glu; Xaa$_{23}$ is Gln; Xaa$_{25}$ is Ala; Xaa$_{26}$ is Arg; Xaa$_{27}$ is Glu; Xaa$_{30}$ is Ala; Xaa$_{31}$ is Trp; Xaa$_{33}$ is Val; Xaa$_{34}$ is Arg; Xaa$_{35}$ is Gly; Xaa$_{36}$ is Arg; Xaa$_{37}$ is Gly; Xaa$_{38}$ is Lys; Xaa$_{39}$ is Gly; Xaa$_{40}$ is Gly; Xaa$_{41}$ is Ser; and Xaa$_{42}$ is Lys.

123. The derivative of any of embodiments 121-122, wherein GLP-1 is a peptide of formula IIc.

124. The derivative of any of embodiments 121-123, wherein the two (P-L) are attached to Lys38 and Lys42.

125. The derivative of any of embodiments 24-81, wherein B is present and U is 2.

126. The derivative of embodiment 125, wherein B is represented by >BL-PL, where >BL is a Branched linker and PL is an optional Pre linker.

127. The derivative of embodiment 126, wherein >BL is a tri-radical.

128. The derivative of any of embodiments 126-127, wherein >BL is represented by the Branched Linker (BL) as defined in any of embodiments 74-81.

129. The derivative of any of embodiments 126-128, wherein PL is a di-radical.

130. The derivative of any of embodiments 125-129, which has formula Ic:

(P-L)$_2$>BL-PL-GLP1;

or a pharmaceutically acceptable salt, amide, or ester thereof.

131. The derivative of any of embodiments 125-130, wherein each P is Chem. 11.

132. The derivative of embodiment 131, wherein x is 18.

133. The derivative of any of embodiments 125-132, wherein each L comprises linker element Chem. 15.

134. The derivative of any of embodiments 125-133, wherein each L comprises linker element Chem. 15, wherein q is 1, m is 2, and n is 0.

135. The derivative of any of embodiments 125-134, wherein each L comprises linker element Chem. 16.

136. The derivative of embodiment 135, wherein k=l=1.

137. The derivative of any of embodiments 125-136, wherein each L comprises linker element Chem. 17.

138. The derivative of any of embodiments 125-137, wherein each L consists of one linker element Chem. 17; one linker element Chem. 15 wherein q is 1 m is 2 and n is 0; and four linker elements Chem. 16 wherein k is 1 and l is 1 (Chem. 17-Chem. 15-4×Chem. 16) interconnected via amide bonds and in the sequence indicated.

139. The derivative of any of embodiments 125-137, wherein each L consists of one linker element Chem. 17; one linker element Chem. 15 wherein q is 1 m is 2 and n is 0; and six linker elements Chem. 16 wherein k is 1 and l is 1 (Chem. 17-Chem. 15-6×Chem. 16) interconnected via amide bonds and in the sequence indicated.

140. The derivative of any of embodiments 125-139, wherein GLP1 comprises a peptide of formula IId (SEQ ID NO: 29):

Xaa$_7$-Trp-Glu-Gly-Thr-Xaa$_{12}$-Thr-Ser-Asp-Xaa$_6$-Ser-Xaa$_8$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$, wherein Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;
Xaa$_{12}$ is Phe or Leu;
Xaa$_{16}$ is Val or Leu;
Xaa$_{18}$ is Ser, Arg, Val, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg or Lys;
Xaa$_{27}$ is Glu, Lys, or Leu;
Xaa$_{30}$ is Ala, Glu, or Arg;
Xaa$_{31}$ is Trp or His;
Xaa$_{33}$ is Val;
Xaa$_{34}$ is Arg, His, Asn, or Gln;
Xaa$_{35}$ is Gly or Ala;
Xaa$_{36}$ is Arg, Lys, or Gly;
Xaa$_{37}$ is Gly, Lys, Pro, or absent; and
Xaa$_{38}$ is Ser, Gly, Ala, Glu, Pro, Lys, or absent;
with the proviso that at least one of Xaa$_{26}$, Xaa$_{27}$, Xaa$_{36}$, Xaa$_{37}$, or Xaa$_{38}$ is Lys; or a pharmaceutically acceptable salt, amide, or ester thereof.

140a. The derivative of embodiment 140, wherein Xaa$_7$ is L-histidine.

141. The derivative of any of embodiments 140-140a, wherein Xaa$_7$ is L-histidine; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Glu; Xaa$_{23}$ is Gln; Xaa$_{25}$ is Ala; Xaa$_{26}$ is Arg; Xaa$_{27}$ is Glu; Xaa$_{30}$ is Ala; Xaa$_{31}$ is Trp; Xaa$_{33}$ is Val; Xaa$_{34}$ is Arg; Xaa$_{35}$ is Gly; Xaa$_{36}$ is Arg; Xaa$_{37}$ is Lys or Pro; and Xaa$_{38}$ is Lys or absent; with the proviso that at least one of Xaa$_{37}$ and Xaa$_{38}$ is Lys.

142. The derivative of any of embodiments 140-141, wherein GLP-1 is a peptide of formula IId.

143. The derivative of any of embodiments 125-142, wherein (P-L) is attached to Lys37 or Lys38.

144. The derivative of any of embodiments 125-143, wherein BL is Chem. 19, wherein u and v independently represents an integer in the range of 0-5, with the provisos that when u is 0 v is an integer in the range of 1-5, and when v is 0 u is an integer in the range of 1-5.

145. The derivative of embodiment 144, wherein u is 0 and v is 4.

146. The derivative of embodiment 144, wherein u is 4 and v is 0.

147. The derivative of any of embodiments 125-146, wherein PL when present comprises Chem. 16.

148. The derivative of embodiment 147, wherein PL comprises from 0 to 2 times of linker element Chem. 16.
149. The derivative of any of embodiments 147-148, wherein each of k and l, independently, is 1-5.
150. The derivative of any of embodiments 147-149, wherein each of k and l is 1.
151. The derivative of any of embodiments 147-150, wherein PL comprises 0 times Chem. 16, viz. does not comprise Chem. 16.
152. The derivative of any of embodiments 147-151, wherein PL is absent.
153. The derivative of any of embodiments 125-152, which has formula Id:

(P-L)$_2$>BL-GLP1;

or a pharmaceutically acceptable salt, amide, or ester thereof.
154. The derivative of any of embodiments 147-150, wherein PL is present and non-optional (i.e., mandatory).
155. The derivative of any of embodiments 147-150 and 154, wherein PL comprises two times Chem. 16.
156. The derivative of any of embodiments 147-150 and 154-155, wherein PL consists of two times Chem. 16.
157. The derivative of any of embodiments 125-143, wherein BL is Chem. 20, wherein each w represents an integer in the range of 0-2.
158. The derivative of embodiment 157, wherein w is 1.
159. The derivative of any of embodiments 157-158, wherein PL is present.
160. The derivative of any of embodiments 157-160, wherein PL comprises Chem. 16.
161. The derivative of any of embodiments 159-160, wherein PL comprises two times linker element Chem. 16.
162. The derivative of any of embodiments 159-160, wherein PL consists of two times linker element Chem. 16.
163. The derivative of any of embodiments 160-162, wherein each of k and l, independently, is 1-5.
163. The derivative of any of embodiments 160-163, wherein each of k and l is 1.
164. The derivative of any of embodiments 24-163, wherein GLP1 is selected from SEQ ID NO: 5, SEQ ID NO: 7, SEQ ID NO: 9, SEQ ID NO: 11, amino acids 1-275 of SEQ ID NO: 15, SEQ ID NO:16, SEQ ID NO: 18, and SEQ ID NO: 20; or a pharmaceutically acceptable salt, amide, or ester thereof.
164a. The derivative of any of embodiments 24-164, wherein the GLP-1 analogue is selected from SEQ ID NO: 5, SEQ ID NO: 7, SEQ ID NO: 9, SEQ ID NO: 11, SEQ ID NO:16, SEQ ID NO: 18, and SEQ ID NO: 20; or a pharmaceutically acceptable salt, amide or ester thereof.
165. A derivative selected from Chem. 21, Chem. 22, Chem. 23, Chem. 24, Chem. 25, Chem. 26, Chem. 27, Chem. 28, Chem. 29, Chem. 30, Chem. 31, and Chem. 32; or a pharmaceutically acceptable salt, amide, or ester thereof.
166. The derivative of any of embodiments 164 and 164a, which is a derivative of any of embodiments 1-165.
167. The derivative of any of embodiments 165-166, which is the compound of Example 1, 2, 3, 4, 5, 7, 8, 9, 10, 11, 12, or 13.
168. The derivative of any of embodiments 1-167 which is a GLP-1 derivative.
169. A GLP-1 analogue selected from SEQ ID NO: 4, SEQ ID NO: 5, SEQ ID NO: 7, SEQ ID NO: 9, SEQ ID NO: 11, amino acids 1-275 of SEQ ID NO: 15, SEQ ID NO: 16, SEQ ID NO: 18, and SEQ ID NO: 20; or a pharmaceutically acceptable salt, amide, or ester thereof.
169a. A GLP-1 analogue selected from SEQ ID NO: 5, SEQ ID NO: 7, SEQ ID NO: 9, SEQ ID NO: 11, amino acids 1-275 of SEQ ID NO: 15, SEQ ID NO: 16, SEQ ID NO: 18, and SEQ ID NO: 20; or a pharmaceutically acceptable salt, amide, or ester thereof.
169b. A GLP-1 analogue selected from SEQ ID NO: 4, SEQ ID NO: 5, SEQ ID NO: 7, SEQ ID NO:9, SEQ ID NO:11, SEQ ID NO:16, SEQ ID NO:18, and SEQ ID NO:20; or a pharmaceutically acceptable salt, amide, or ester thereof.
169c. A GLP-1 analogue selected from SEQ ID NO: 5, SEQ ID NO: 7, SEQ ID NO: 9, SEQ ID NO:11, SEQ ID NO:16, SEQ ID NO:18, and SEQ ID NO:20; or a pharmaceutically acceptable salt, amide, or ester thereof.
170. A compound comprising, or having, amino acids 1-275 of SEQ ID NO: 15, or a pharmaceutically acceptable salt, amide, or ester thereof.
170a. A compound comprising, or having, amino acids 276-550 of SEQ ID NO: 15, or a pharmaceutically acceptable salt, amide, or ester thereof.
170b. A compound comprising, or having, SEQ ID NO: 15.
170c. A compound which is a dimer of i) two compounds of embodiment 170, ii) two compounds of embodiment 170a, iii) one compound of embodiment 170 and one compound of embodiment 170a.
170d. The compound of any of embodiments 170b-170c, which has Cys-Cys bonds between the two Cys residues at position 55, and the two Cys residues at position 58, i.e. between Cys55 and Cys330 as well as between Cys58 and Cys333 of SEQ ID NO: 15.
171. The derivative or analogue of any of embodiments 1-170d, which is a GLP-1 receptor agonist.
172. The derivative or analogue of any of embodiments 1-171, which is a full GLP-1 receptor agonist.
173. The derivative or analogue of any of embodiments 1-172, which is biologically active in vitro.
174. The derivative or analogue of any of embodiments 1-173, which is potent in vitro.
175. The derivative or analogue of any of embodiments 1-174, which is capable of activating the human GLP-1 receptor.
176. The derivative or analogue of any of embodiments 1-175, which is capable of activating the human GLP-1 receptor in an assay with whole cells expressing the human GLP-1 receptor, wherein the assay is performed in the absence of HSA (0% HSA).
177. The derivative or analogue of any of embodiments 1-176, where the response of the human GLP-1 receptor is measured in a reporter gene assay, such as the assay of Example 15.
178. The derivative or analogue of any of embodiments 171-177, wherein the GLP-1 receptor agonism, the in vitro biological activity, the in vitro potency, or the capability of activating the human GLP-1 receptor, respectively, is determined essentially as described in Example 15.
179. The derivative or analogue of any of embodiments 1-178, which has an in vitro potency corresponding to an EC$_{50}$ of 300 pM or below.
180. The derivative or analogue of any of embodiments 1-179, which has an in vitro potency corresponding to an EC$_{50}$ of 200 pM or below.
181. The derivative or analogue of any of embodiments 1-180, which has an in vitro potency corresponding to an EC$_{50}$ of 150 pM or below.
182. The derivative or analogue of any of embodiments 1-181, which has an in vitro potency corresponding to an EC$_{50}$ of 125 pM or below.

183. The derivative or analogue of any of embodiments 1-182, which has an in vitro potency corresponding to an $EC_{50}$ of 100 pM or below.

184. The derivative or analogue of any of embodiments 1-183, which has an in vitro potency corresponding to an $EC_{50}$ of 75 pM or below.

185. The derivative or analogue of any of embodiments 1-184, which has an in vitro potency corresponding to an $EC_{50}$ of 50 pM or below.

186. The derivative or analogue of any of embodiments 1-185, which has an in vitro potency corresponding to an $EC_{50}$ of 30 pM or below.

187. The derivative or analogue of any of embodiments 179-186, wherein the $EC_{50}$ is determined essentially as described in Example 15.

188. The derivative or analogue of any of embodiments 1-187, which has an in vitro potency corresponding to an $EC_{50}$ of less than 60 times the $EC_{50}$ of semaglutide, wherein the $EC_{50}$ of semaglutide is determined in the same way as the $EC_{50}$ of the derivative.

189. The derivative or analogue of any of embodiments 1-188, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.

190. The derivative or analogue of any of embodiments 1-189, which has an in vitro potency corresponding to an $EC_{50}$ of less than 8 times the $EC_{50}$ of semaglutide, wherein the $EC_{50}$ of semaglutide is determined in the same way as the $EC_{50}$ of the derivative.

191. The derivative or analogue of any of embodiments 1-190, which has an in vitro potency corresponding to an $EC_{50}$ of less than 6 times the $EC_{50}$ of semaglutide, wherein the $EC_{50}$ of semaglutide is determined in the same way as the $EC_{50}$ of the derivative.

192. The derivative or analogue of any of embodiments 1-191, which has an in vitro potency corresponding to an $EC_{50}$ of less than 3 times the $EC_{50}$ of semaglutide, wherein the $EC_{50}$ of semaglutide is determined in the same way as the $EC_{50}$ of the derivative.

193. The derivative or analogue of any of embodiments 1-192, which has an in vitro potency corresponding to an $EC_{50}$ of less than 2 times the $EC_{50}$ of semaglutide, wherein the $EC_{50}$ of semaglutide is determined in the same way as the $EC_{50}$ of the derivative.

194. The derivative or analogue of any of embodiments 1-193, which has an in vitro potency corresponding to an $EC_{50}$ of less than or equal to the $EC_{50}$ of semaglutide, wherein the $EC_{50}$ of semaglutide is determined in the same way as the $EC_{50}$ of the derivative.

195. The derivative or analogue of any of embodiments 188-194, wherein the $EC_{50}$ is determined essentially as described in Example 15.

196. The derivative or analogue of any of embodiments 1-195, which is capable of binding to the GLP-1 receptor.

197. The derivative or analogue of any of embodiments 1-196, which is capable of binding to the GLP-1 receptor at a low concentration of HSA (max. 0.001% (w/v) final assay concentration).

198. The derivative or analogue of any of embodiments 1-195, which is capable of binding to the GLP-1 receptor at a high concentration of HSA (2.0% (w/v) final assay concentration).

199. The derivative or analogue of any of embodiments 196-198, wherein the binding to the human GLP-1 receptor is measured in a competitive binding assay, such as the assay of Example 16.

200. The derivative or analogue of any of embodiments 196-199, wherein the binding to the human GLP-1 receptor in vitro is determined essentially as described in Example 16.

201. The derivative or analogue of any of embodiments 1-200, which at a low concentration of HSA is capable of binding to the human GLP-1 receptor with an $IC_{50}$ of 20 nM or below.

202. The derivative or analogue of any of embodiments 1-201, which at a low concentration of HSA is capable of binding to the human GLP-1 receptor with an $IC_{50}$ of 10 nM or below.

203. The derivative or analogue of any of embodiments 1-202, which at a low concentration of HSA is capable of binding to the human GLP-1 receptor with an $IC_{50}$ of 4.0 nM or below.

204. The derivative or analogue of any of embodiments 1-203, which at a low concentration of HSA is capable of binding to the human GLP-1 receptor with an $IC_{50}$ of 2.0 nM or below.

205. The derivative or analogue of any of embodiments 1-204, which at a low concentration of HSA is capable of binding to the human GLP-1 receptor with an $IC_{50}$ of 1.0 nM or below.

206. The derivative or analogue of any of embodiments 1-205, which at a low concentration of HSA is capable of binding to the human GLP-1 receptor with an $IC_{50}$ of 0.50 nM or below.

207. The derivative or analogue of any of embodiments 201-206, wherein the $IC_{50}$ is determined essentially as described in Example 16, in a reaction with max. 0.001% (w/v) HSA (final assay concentration).

208. The derivative or analogue of any of embodiments 1-207, which at a low concentration of HSA is capable of binding to the human GLP-1 receptor with an $IC_{50}$ of less than 35 times the $IC_{50}$ of semaglutide, wherein the $IC_{50}$ of semaglutide is determined in the same way as the $IC_{50}$ of the derivative.

209. The derivative or analogue of any of embodiments 1-208, which at a low concentration of HSA is capable of binding to the human GLP-1 receptor with an $IC_{50}$ of less than 20 times the $IC_{50}$ of semaglutide, wherein the $IC_{50}$ of semaglutide is determined in the same way as the $IC_{50}$ of the derivative.

210. The derivative or analogue of any of embodiments 1-209, which at a low concentration of HSA is capable of binding to the human GLP-1 receptor with an $IC_{50}$ of less than 8 times the $IC_{50}$ of semaglutide, wherein the $IC_{50}$ of semaglutide is determined in the same way as the $IC_{50}$ of the derivative.

211. The derivative or analogue of any of embodiments 1-210, which at a low concentration of HSA is capable of binding to the human GLP-1 receptor with an $IC_{50}$ of less than 4 times the $IC_{50}$ of semaglutide, wherein the $IC_{50}$ of semaglutide is determined in the same way as the $IC_{50}$ of the derivative.

212. The derivative or analogue of any of embodiments 1-211, which at a low concentration of HSA is capable of binding to the human GLP-1 receptor with an $IC_{50}$ of less than 3 times the $IC_{50}$ of semaglutide, wherein the $IC_{50}$ of semaglutide is determined in the same way as the $IC_{50}$ of the derivative.

213. The derivative or analogue of any of embodiments 1-212, which at a low concentration of HSA is capable of binding to the human GLP-1 receptor with an $IC_{50}$ of less than 2 times the $IC_{50}$ of semaglutide, wherein the $IC_{50}$ of semaglutide is determined in the same way as the $IC_{50}$ of the derivative.

214. The derivative or analogue of any of embodiments 1-213, which at a low concentration of HSA is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

215. The derivative or analogue of any of embodiments 1-214, which at a low concentration of HSA is capable of binding to the human GLP-1 receptor with an $IC_{50}$ of less than 0.50 times the $IC_{50}$ of semaglutide, wherein the $IC_{50}$ of semaglutide is determined in the same way as the $IC_{50}$ of the derivative.

216. The derivative or analogue of any of embodiments 208-215, wherein the $IC_{50}$ is determined essentially as described in Example 16, in a reaction with max. 0.001% (w/v) HSA (final assay concentration).

217. The derivative or analogue of any of embodiments 1-216, which at 2.0% (w/v) HSA (final assay concentration) is capable of binding to the human GLP-1 receptor with an $IC_{50}$ of 800 nM or below.

218. The derivative or analogue of any of embodiments 1-217, which at 2.0% (w/v) HSA (final assay concentration) is capable of binding to the human GLP-1 receptor with an $IC_{50}$ of 450 nM or below.

219. The derivative or analogue of any of embodiments 1-218, which at 2.0% (w/v) HSA (final assay concentration) is capable of binding to the human GLP-1 receptor with an $IC_{50}$ of 800 nM or below.

220. The derivative or analogue of any of embodiments 1-219, which at 2.0% (w/v) HSA (final assay concentration) is capable of binding to the human GLP-1 receptor with an $IC_{50}$ of 600 nM or below.

221. The derivative or analogue of any of embodiments 1-220, which at 2.0% (w/v) HSA (final assay concentration) is capable of binding to the human GLP-1 receptor with an $IC_{50}$ of 400 nM or below.

222. The derivative or analogue of any of embodiments 1-221, which at 2.0% (w/v) HSA (final assay concentration) is capable of binding to the human GLP-1 receptor with an $IC_{50}$ of 200 nM or below.

223. The derivative or analogue of any of embodiments 217-222, wherein the $IC_{50}$ is determined essentially as described in Example 16, in a reaction with 2.0% (w/v) HSA (final assay concentration).

224. The derivative or analogue of any of embodiments 1-223, which at 2.0% (w/v)HSA (final assay concentration) is capable of binding to the human GLP-1 receptor with an $IC_{50}$ of less than eight times the $IC_{50}$ of semaglutide, wherein the $IC_{50}$ of semaglutide is determined in the same way as the $IC_{50}$ of the derivative.

225. The derivative or analogue of any of embodiments 1-223, which at 2.0% (w/v) HSA (final assay concentration) is capable of binding to the human GLP-1 receptor with an $IC_{50}$ of less than six times the $IC_{50}$ of semaglutide, wherein the $IC_{50}$ of semaglutide is determined in the same way as the $IC_{50}$ of the derivative.

226. The derivative or analogue of any of embodiments 1-223, which at 2.0% (w/v) HSA (final assay concentration) is capable of binding to the human GLP-1 receptor with an $IC_{50}$ of less than four times the $IC_{50}$ of semaglutide, wherein the $IC_{50}$ of semaglutide is determined in the same way as the $IC_{50}$ of the derivative.

227. The derivative or analogue of any of embodiments 1-223, which at 2.0% (w/v) HSA (final assay concentration) is capable of binding to the human GLP-1 receptor with an $IC_{50}$ of less than two times the $IC_{50}$ of semaglutide, wherein the $IC_{50}$ of semaglutide is determined in the same way as the $IC_{50}$ of the derivative.

228. The derivative or analogue of any of embodiments 1-223, which at 2.0% (w/v) HSA (final assay concentration) is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

229. The derivative or analogue of any of embodiments 224-228, wherein the $IC_{50}$ is determined essentially as described in Example 16, in a reaction with 2.0% (w/v) HSA (final assay concentration).

230. The derivative or analogue of any of embodiments 1-229, which is potent in vivo.

231. The derivative or analogue of any of embodiments 1-230, which is potent in vivo when determined in any suitable animal model, such as mouse.

232. The derivative or analogue of any of embodiments 1-231, wherein the animal model is db/db mouse.

233. The derivative or analogue of any of embodiments 1-232, wherein the blood glucose lowering effect is determined.

234. The derivative or analogue of any of embodiments 1-233, wherein the body weight lowering effect is determined.

235. The derivative or analogue of any of embodiments 1-234, wherein blood glucose lowering effect and/or body weight lowering effect is determined in vivo in db/db mouse using any suitable study protocol and methodology, e.g. as described in Example 17.

236. The derivative or analogue of any of embodiments 1-235, wherein the blood glucose lowering effect and/or the body weight lowering effect is determined in vivo in db/db mouse, essentially as described in Example 17.

237. The derivative or analogue of any of embodiments 1-236, which has the effect in vivo of decreasing blood glucose after 24 hours, or 48 hours, determined in a single-dose study in an obese, diabetic mouse model, in a suitable dose, such as 0.3, 1.0, 3.0, 10, 30, or 100 nmol/kg.

238. The derivative or analogue of any of embodiments 1-237, wherein dose response curves for delta blood glucose and delta body weight versus time are drawn up for each of the single doses, wherein the delta refers to the actual blood glucose/body weight at a given time, minus baseline, where baseline is the level of blood glucose and body weight at time 0.

239. The derivative or analogue of any of embodiments 1-238, wherein the area under the curve for delta blood glucose from 0 until 24 hours (AUC $\Delta BG_{24h}$) and delta body weight gain at 24 hours post dosing ($\Delta BW_{24h}$) are calculated, for each of the individual dose response curves, and the Effective Doses 50% (ED50, dose of GLP-1 derivative that gives a response halfway between baseline and maximal effect) are calculated for AUC $\Delta BG_{24h}$ and $\Delta BW_{24h}$.

240. The derivative or analogue of any of embodiments 1-239, which dose dependently decreases blood glucose.

241. The derivative of analogue of any of embodiments 1-240, which dose dependently decreases body weight.

242. The derivative or analogue of any of embodiments 1-241, wherein ED50 AUC $\Delta BG24$ h is at least 2.0 nmol/kg.

243. The derivative or analogue of any of embodiments 1-242, wherein ED50 $\Delta BW24$ h is at least 4.0 nmol/kg.

244. A method of preparing a derivative or analogue of any of embodiments 1-243, which comprises the step of recombinantly producing a GLP-1 analogue having Trp at a position corresponding to position 8 of GLP-1(7-37) (SEQ ID NO: 1).

245. The method of embodiment 244, wherein the GLP-1 analogue has GLP-1 activity.

246. The method of any of embodiments 244-245, wherein the GLP-1 analogue is DPP-IV stabilised.

247. The method of any of embodiments 244-246, wherein the GLP-1 analogue has an in vitro potency as defined in any of embodiments 179-195.

248. The method of any of embodiments 244-247, wherein the DPP-IV stabilised GLP-1 analogue has a half-life of at least 10 minutes when tested using the method of Example 14.

249. The method of any of embodiments 244-248, wherein the DPP-IV stabilised GLP-1 analogue has a half-life of at least 15 minutes when tested using the method of Example 14.

250. The method of any of embodiments 244-249, wherein the DPP-IV stabilised GLP-1 analogue is at least 10 times, preferably at least 15 times, more preferably at least 20 times as stable as native GLP-1 when tested in a suitable DPP-IV stability assay such as the assay of Example 14.

251. The method of any of embodiments 244-250, which further comprises the step of purifying the recombinantly produced GLP-1 analogue.

252. The method of any of embodiments 244-251, which further comprises the step of attaching a substituent to a Lys residue of the GLP-1 analogue, whereby a derivative of the GLP-1 analogue is produced.

253. The method of embodiment 252, wherein one or two substituents are attached.

254. The method of embodiment 253, wherein one substituent is attached to one Lys residue.

255. The method of embodiment 253, wherein two substituents are attached to two Lys residues, one substituent to each Lys residue.

256. The method of embodiment 253, wherein two substituents are attached to one Lys residue, via the Branching group (B).

257. The method of any of embodiments 252-257, which further comprises the step of purifying the GLP-1 derivative.

258. The method of any of embodiments 244-257 which is for the preparation of a GLP-1 analogue or derivative as defined in any of embodiments 1-243.

259. A pharmaceutical composition comprising a derivative or an analogue according to any of embodiments 1-243, and a pharmaceutically acceptable excipient.

260. A derivative or an analogue according to any of embodiments 1-243, for use as a medicament.

261. A derivative or an analogue according to any of embodiments 1-243, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

262. Use of a derivative or an analogue according to any of embodiments 1-243, in the manufacture of a medicament for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriatic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

263. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriatic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative or an analogue according to any of embodiments 1-243, is administered.

In some embodiments the derivative of the invention is not selected from Chem. 21, Chem. 22, Chem. 23, Chem. 24, Chem. 25, Chem. 26, Chem. 27, Chem. 28, Chem. 29, Chem. 30, Chem. 31, and Chem. 32; and is also not a pharmaceutically acceptable salt, amide, or ester thereof.

In some embodiments the GLP-1 analogue of the invention is not selected from SEQ ID NO:4, SEQ ID NO:5, SEQ ID NO:7, SEQ ID NO:9, SEQ ID NO:11, SEQ ID NO: 15, amino acids 1-275 of SEQ ID NO: 15, SEQ ID NO:16, SEQ ID NO: 18, and SEQ ID NO: 20; and is also not a pharmaceutically acceptable salt, amide, or ester thereof.

Additional Particular Embodiments

The following are additional particular embodiments of the invention:

1. A derivative comprising a GLP-1 analogue having a Trp at a position corresponding to position 8 of GLP-1(7-37) (SEQ ID NO: 1) and wherein a substituent comprising at least eight consecutive —$CH_2$-groups and at least one functional group (FG) with a pKa<7 is attached to a Lys residue of the GLP-1 analogue.
2. The derivative of any of embodiments 1-2, which comprises one or two substituents attached to one or two Lys residues of the GLP-1 analogue.
3. The derivative of embodiment 1, wherein the substituent(s) is (are) attached to the epsilon amino group of the Lys residue(s).
4. The derivative of any of embodiments 1-3, wherein the number of consecutive —$CH_2$-groups in the substituent(s) is in the range of 8-20.
5. The derivative of embodiment 4, wherein the number is in the range of 9-18.
6. The derivative of any of embodiments 4-5, wherein the number is 9, 10, 12, 14, 15, 16, or 18.
7. The derivative of any of embodiments 1-6, wherein the at least one FG is independently selected from Chem. 1, Chem. 2, and Chem. 4:

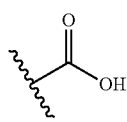

Chem. 1

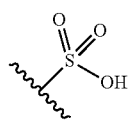

Chem. 2

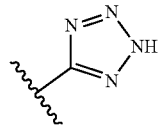

Chem. 3 or a pharmaceutically acceptable salt, amide, or ester thereof.

8. The derivative of any of embodiments 1-7, wherein the number, in each of the one or two substituents, of FG's with a pKa<7 is in the range of 1-10.
9. The derivative of embodiment 8, wherein the number is in the range of 1-8.
10. The derivative of any of embodiments 8-9, wherein the number is in the range of 1-6.
11. The derivative of any of embodiments 8-10, wherein the number is in the range of 1-4.
12. The derivative of any of embodiments 8-11, wherein the number is 1 or 2.
13. The derivative of any of embodiments 1-12, wherein pKa is the pH of a solution of $CH_3$-FG in water.
14. The derivative of any of embodiments 1-13, wherein pKa is minus log Ka for the equilibrium of Equation 1:

$$CH_3\text{-FG}+H_2O \leftrightarrow FG^- + H_3O^+. \qquad \text{Equation 1:}$$

15. The derivative of any of embodiments 1-14, wherein the GLP-1 analogue comprises a peptide of formula II (SEQ ID NO: 25):

$Xaa_7$-Trp-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$-$Xaa_{42}$, wherein $Xaa_7$ is L-histidine, (S)-2-Hydroxy-3-(1H-imidazol-4-yl)-propionic acid, D-histidine, deamino-histidine, homohistidine, $N^\alpha$-acetyl-histidine, $N^\alpha$-formyl-histidine, $N^\alpha$-methyl-histidine, 3-pyridylalanine, 2-pyridylalanine, or 4-pyridylalanine;

$Xaa_{12}$ is Phe or Leu;
$Xaa_{16}$ is Val or Leu;
$Xaa_{18}$ is Ser, Arg, Val, or Leu;
$Xaa_{19}$ is Tyr or Gln;
$Xaa_{20}$ is Leu or Met;
$Xaa_{22}$ is Gly or Glu;
$Xaa_{23}$ is Gln, Glu, or Arg;
$Xaa_{25}$ is Ala or Val;
$Xaa_{26}$ is Arg or Lys;
$Xaa_{27}$ is Glu, Lys, or Leu;
$Xaa_{30}$ is Ala, Glu, or Arg;
$Xaa_{31}$ is Trp or His;
$Xaa_{33}$ is Val;
$Xaa_{34}$ is Arg, His, Asn, or Gln;
$Xaa_{35}$ is Gly or Ala;
$Xaa_{36}$ is Arg, Lys, or Gly;
$Xaa_{37}$ is Gly, Lys, Pro, or absent;
$Xaa_{38}$ is Ser, Gly, Ala, Glu, Pro, Lys, or absent;
$Xaa_{39}$ is Ser, Gly, Ala, Glu, Pro, or absent;
$Xaa_{40}$ is Ser, Gly, Ala, Glu, Pro, or absent;
$Xaa_{41}$ is Ser, Gly, Ala, Glu, Pro, or absent; and
$Xaa_{42}$ is Lys or absent;

with the proviso that at least one of $Xaa_{26}$, $Xaa_{27}$, $Xaa_{36}$, $Xaa_{37}$, $Xaa_{38}$, or $Xaa_{42}$ is Lys;

or a pharmaceutically acceptable salt, amide, or ester thereof.

16. The derivative of embodiment 15, wherein $Xaa_7$ is L-histidine; $Xaa_{12}$ is Phe; $Xaa_{16}$ is Val; $Xaa_{18}$ is Ser; $Xaa_{19}$ is Tyr; $Xaa_{20}$ is Leu; $Xaa_{22}$ is Gly or Glu; $Xaa_{23}$ is Gln; $Xaa_{25}$ is Ala; $Xaa_{26}$ is Arg or Lys; $Xaa_{27}$ is Glu or Lys; $Xaa_{30}$ is Ala or Glu; $Xaa_{31}$ is Trp; $Xaa_{33}$ is Val; $Xaa_{34}$ is Arg; $Xaa_{35}$ is Gly; $Xaa_{36}$ is Arg or Lys; $Xaa_{37}$ is Gly, Lys, or Pro; $Xaa_{38}$ is Glu, Lys, or absent; $Xaa_{39}$ is Gly or absent; $Xaa_{40}$ is Gly or absent; $Xaa_{41}$ is Ser or absent; and $Xaa_{42}$ is Lys or absent.

17. The derivative of any of embodiments 15-16, wherein the GLP-1 analogue is a peptide of formula II.

18. The derivative of any of embodiments 15-17, wherein if $Xaa_{37}$ is absent then each of $Xaa_{38}$, $Xaa_{39}$, $Xaa_{40}$, $Xaa_{41}$, and $Xaa_{42}$ is also absent.

18a. The derivative of any of embodiments 15-18, wherein if $Xaa_{38}$ is absent then each of $Xaa_{39}$, $Xaa_{40}$, $Xaa_{41}$, and $Xaa_{42}$ is also absent.

19. The derivative of any of embodiments 15-18a, wherein if $Xaa_{39}$ is absent then each of $Xaa_{40}$, $Xaa_{41}$, and $Xaa_{42}$ is also absent.

20. The derivative of any of embodiments 15-19, wherein if $Xaa_{40}$ is absent then each of $Xaa_{41}$ and $Xaa_{42}$ is also absent.

21. The derivative of any of embodiments 15-20, wherein if $Xaa_{41}$ is absent then $Xaa_{42}$ is also absent.

22. The derivative of any of embodiments 15-21, wherein if one of $Xaa_{38}$, $Xaa_{39}$, $Xaa_{40}$, $Xaa_{41}$, or $Xaa_{42}$ is absent then each subsequent amino acid residue is also absent.

23. The derivative of any of embodiments 15-22 wherein one or two of $Xaa_{26}$, $Xaa_{27}$, $Xaa_{36}$, $Xaa_{37}$, $Xaa_{38}$, or $Xaa_{42}$ is/are Lys.

23a. The derivative of embodiment 23 wherein the one or two substituents is/are attached to the epsilon amino group of one or two Lys residues of the analogue.

23b. The derivative of any of embodiments 1-23a, wherein the GLP-1 analogue is selected from SEQ ID NO: 5, SEQ ID NO: 7, SEQ ID NO: 9, and SEQ ID NO: 11; or a pharmaceutically acceptable salt, amide or ester thereof.

24. A derivative of formula I:

(P-L)$_U$-B-GLP1, wherein GLP1 is a GLP-1 analogue having a Trp at a position corresponding to position 8 of GLP-1(7-37) (SEQ ID NO: 1), (P-L) is a substituent attached to a Lys residue of the GLP-1 analogue via an optional Branching group (B) and comprising a Protracting moiety (P) and a Linker (L), U represents the number of substituents (P-L) in the derivative and is 1 or 2;

or a pharmaceutically acceptable salt, amide, or ester thereof.

24a. The derivative of embodiment 24 which comprises at least one functional group (FG) with a pKa<7.

24b. The derivative of embodiment 24a, wherein the at least one functional group is independently selected from Chem. 1, Chem. 2, and Chem. 4.

25. The derivative of any of embodiments 24-24b which is a derivative according to any of embodiments 1-23b.

26. The derivative of any of embodiments 24-25, which comprises one or two substituents (P-L) attached to one or two Lys residues of the GLP-1 analogue.

26. The derivative of any of embodiments 24-25, wherein the GLP-1 analogue is defined as in any of embodiments 15-23b.

27. The derivative of any of embodiments 24-26, wherein the (each) substituent (P-L) comprises a Protracting moiety (P) selected from Chem. 10, Chem. 11, Chem. 12, Chem. 13, and Chem. 14:

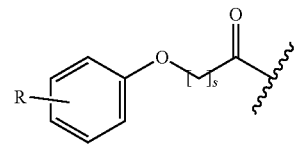
Chem. 10

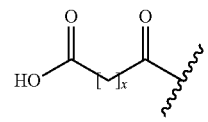
Chem. 11

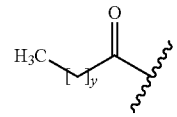
Chem. 12

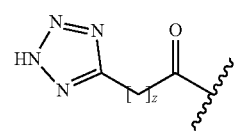
Chem. 13

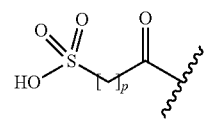
Chem. 14 and a Linker (L) comprising at least one linker element selected from Chem. 15, Chem. 16, Chem. 17, and Chem. 18:

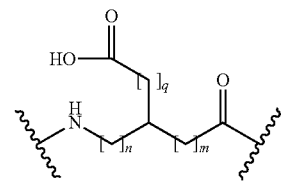
Chem. 15

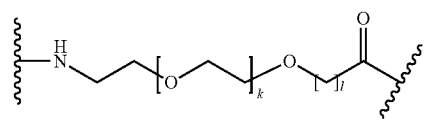
Chem. 16

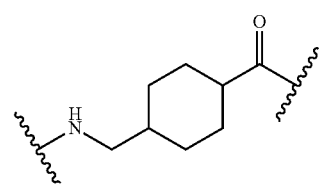
Chem. 17

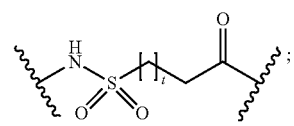
Chem. 18 wherein

R is —COOH;

each of s, x, y, z, and p independently represents an integer in the range of 8-20;

each of n, m, and q independently represents an integer in the range of 0-4; and each of k, l, and t independently represents an integer in the range of 1-5.

28. The derivative of embodiment 27, wherein at least one linker element means a number of linker elements in the (each) substituent (P-L) in the range of 1-10.

29. The derivative of any of embodiments 27-28 which contains from 1 to 8 linker elements in the (each) substituent (P-L).

30. The derivative of any of embodiments 24-29, wherein the (each) substituent (P-L) consists of a Protracting moiety (P) and a linker (L).

31. The derivative of any of embodiments 24-30, wherein P is Chem. 10.

32. The derivative of any of embodiments 24-31, wherein R is at position 3 of the benzene ring (m).

33. The derivative of any of embodiments 24-31, wherein R is at position 4 of the benzene ring (p).

34. The derivative of any of embodiments 24-33, wherein s is 8-20.

35. The derivative of any of embodiments 24-34, wherein s is 8-10.

36. The derivative of any of embodiments 24-35 wherein s is 9.

37. The derivative of any of embodiments 24-30, wherein P is Chem. 11.

38. The derivative of any of embodiments 24-30 and 37, wherein x is 8-20.

39. The derivative of any of embodiments 24-30 and 37-38, wherein x is 12-20.

40. The derivative of any of embodiments 24-30 and 37-39, wherein x is 12.

41. The derivative of any of embodiments 24-30 and 37-39, wherein x is 16.

42. The derivative of any of embodiments 24-30 and 37-39, wherein x is 18.

43. The derivative of any of embodiments 24-30, wherein P is Chem. 12.

44. The derivative of any of embodiments 24-30 and 43, wherein y is 8-20.

45. The derivative of any of embodiments 24-30 and 43-44, wherein y is 12-20.

46. The derivative of any of embodiments 24-30 and 43-45, wherein y is 14.

47. The derivative of any of embodiments 24-30, wherein P is Chem. 13.

48. The derivative of any of embodiments 24-30 and 47, wherein z is 8-20.

49. The derivative of any of embodiments 24-30 and 47-48, wherein z is 13-17.

50. The derivative of any of embodiments 24-30 and 47-49, wherein z is 15.

51. The derivative of any of embodiments 24-30, wherein P is Chem. 14.

52. The derivative of any of embodiments 24-30 and 51, wherein p is 8-20.

53. The derivative of any of embodiments 24-30 and 51-53, wherein p is 13-17.

54. The derivative of any of embodiments 24-30 and 51-53, wherein p is 15.

55. The derivative of any of embodiments 24-54, wherein L comprises linker element Chem. 15.

56. The derivative of any of embodiments 24-55, wherein each of n, m, and q, independently, is 0-4.

57. The derivative of any of embodiments 24-56, wherein n is 0, m is 2, and q is 1.

58. The derivative of any of embodiments 24-57, wherein L comprises from 0 to 6 times of linker element Chem. 16.

59. The derivative of any of embodiments 24-58, wherein each of k and l, independently, is 1-5.

60. The derivative of any of embodiments 24-59, wherein each of k and l is 1.

61. The derivative of any of embodiments 58-60, wherein L comprises 0 times Chem. 16, viz. does not comprise Chem. 16.

62. The derivative of any of embodiments 58-60, wherein L comprises 2 times Chem. 16.

63. The derivative of any of embodiments 58-60, wherein L comprises 4 times Chem. 16.

64. The derivative of any of embodiments 58-60, wherein L comprises 6 times Chem. 16.

65. The derivative of any of embodiments 24-64, wherein L comprises linker element Chem. 17.

66. The derivative of any of embodiments 24-65, wherein L comprises linker element Chem. 18.

67. The derivative of any of embodiments 24-66, wherein t is 1-5.

68. The derivative of any of embodiments 24-67, wherein t is 2.

69. The derivative of any of embodiments 24-68, wherein if there is more than one linker element the linker elements are interconnected via amide bonds.

70. The derivative of embodiment 69, wherein the more than one interconnected linker elements constitute the linker, L.

71. The derivative of embodiment 69, wherein the sole linker element constitutes the linker, L.

72. The derivative of any of embodiments 70-71, wherein the (each) linker (L) and the (each) protracting moiety (P) are interconnected by an amide bond.

73. The derivative of any of embodiments 70-72, wherein the (each) linker (L) is connected by an amide bond to the epsilon amino group of the (each) Lys residue, optionally via the Branching group (B).

74. The derivative of any of embodiments 24-73, wherein the Branching group (B) comprises a Branched linker (BL) selected from Chem. 19 and Chem. 20:

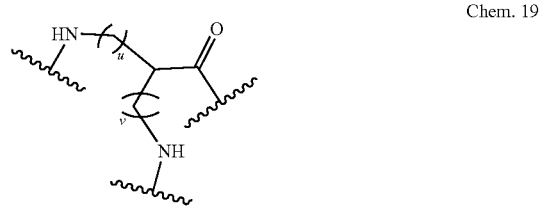

Chem. 19

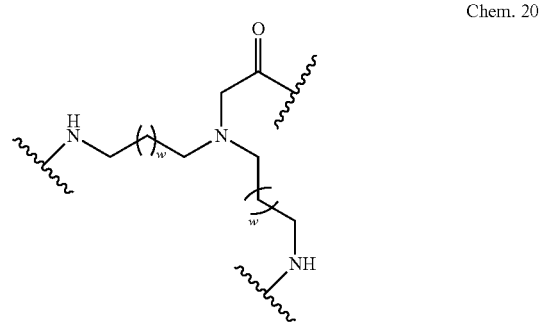

Chem. 20 wherein u and v independently represents an integer in the range of 0-5, with the provisos that when u is 0 v is an integer in the range of 1-5, and when v is 0 u is an integer in the range of 1-5; and where each w represents an integer in the range of 0-2.
75. The derivative of embodiment 74, wherein BL is Chem. 19.
76. The derivative of any of embodiments 74-75, wherein u and v independently represents an integer in the range of 0-5, with the provisos that when u is 0 v is 1-5, and when v is 0 u is 1-5.
77. The derivative of any of embodiments 74-76, wherein u is 0 and v is 4.
78. The derivative of any of embodiments 74-76, wherein u is 4 and v is 0.
79. The derivative of embodiment 74, wherein BL is Chem. 20.
80. The derivative of any of embodiments 74 and 79, wherein w is 0-2.
81. The derivative of any of embodiments 74 and 79-80, wherein w is 1.
82. The derivative of any of embodiments 24-81, wherein B is absent and U is 1.
83. The derivative of any of embodiments 24-82, which has formula Ia: (P-L)-GLP1; or a pharmaceutically acceptable salt, amide, or ester thereof.
84. The derivative of any of embodiments 82-84, wherein P is selected from Chem. 11 and Chem. 12.
85. The derivative of embodiment 84, wherein P is Chem. 11.
86. The derivative of embodiment 85, wherein x is 16.
87. The derivative of embodiment 84, wherein P is Chem. 12.
88. The derivative of embodiment 87, wherein y is 14.
89. The derivative of any of embodiments 82-88, wherein L comprises linker element Chem. 15.
90. The derivative of any of embodiments 82-89, wherein L comprises linker element Chem. 15, wherein q is 1, m is 2, and n is 0.
91. The derivative of embodiment 90, wherein L consists of the linker element Chem. 15, wherein q is 1, m is 2, and n is 0.
92. The derivative of any of embodiments 82-90, wherein L comprises linker element Chem. 16.
93. The derivative of any of embodiments 82-90 and 92, wherein L comprises two linker elements Chem. 16.
94. The derivative of any of embodiments 92-93, wherein k=l=1.
95. The derivative of any of embodiments 82-90 and 92-94, wherein L consists of one linker element Chem. 15 wherein q is 1 m is 2 and n is 0; and two linker elements Chem. 16 wherein k is 1 and l is 1 (Chem. 15-2×Chem. 16) interconnected via amide bonds and in the sequence indicated.
96. The derivative of any of embodiments 82-95, wherein GLP1 comprises a peptide of formula IIa (SEQ ID NO: 26):
    Xaa$_7$-Trp-Glu-Gly-Thr-Xaa$_{12}$-Thr-Ser-Asp-Xaa$_6$-Ser-Xaa$_8$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_3$-Xaa$_{36}$-Xaa$_{37}$,
wherein
    Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;
    Xaa$_{12}$ is Phe or Leu;
    Xaa$_{16}$ is Val or Leu;
    Xaa$_{18}$ is Ser, Arg, Val, or Leu;
    Xaa$_{19}$ is Tyr or Gln;
    Xaa$_{20}$ is Leu or Met;
    Xaa$_{22}$ is Gly or Glu;
    Xaa$_{23}$ is Gln, Glu, or Arg;
    Xaa$_{25}$ is Ala or Val;
    Xaa$_{26}$ is Arg or Lys;
    Xaa$_{27}$ is Glu, Lys, or Leu;
    Xaa$_{30}$ is Ala, Glu, or Arg;
    Xaa$_{31}$ is Trp or His;
    Xaa$_{33}$ is Val;
    Xaa$_{34}$ is Arg, His, Asn, or Gln;
    Xaa$_{35}$ is Gly or Ala;
    Xaa$_{36}$ is Arg, Lys, or Gly; and
    Xaa$_{37}$ is Gly, Lys, Pro, or absent;
    with the proviso that at least one of Xaa$_{26}$, Xaa$_{27}$, Xaa$_{36}$, or Xaa$_{37}$ is Lys;
or a pharmaceutically acceptable salt, amide, or ester thereof.
97. The derivative of embodiment 96, wherein Xaa$_7$ is L-histidine; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Gly; Xaa$_{23}$ is Gln; Xaa$_{25}$ is Ala; Xaa$_{26}$ is Lys; Xaa$_{27}$ is Glu; Xaa$_{30}$ is Ala; Xaa$_{31}$ is Trp; Xaa$_{33}$ is Val; Xaa$_{34}$ is Arg; Xaa$_{35}$ is Gly; Xaa$_{36}$ is Arg; and Xaa$_{37}$ is Gly.
98. The derivative of any of embodiments 96-97, wherein GLP-1 is a peptide of formula IIa.
99. The derivative of any of embodiments 82-98, wherein (P-L) is attached to Lys26.
100. The derivative of any of embodiments 24-81, wherein B is absent and U is 2.
101. The derivative of any of embodiments 24-81 and 100, which has formula Ib: (P-L)$_2$-GLP1; or a pharmaceutically acceptable salt, amide, or ester thereof.
102. The derivative of any of embodiments 100-101, wherein each P is selected, independently, from Chem. 10 and Chem. 11.
103. The derivative of any of embodiment 102, wherein the two P are identical.
104. The derivative of embodiment 103, wherein P is Chem. 10.
105. The derivative of embodiment 104, wherein R is —COOH.
106. The derivative of any of embodiments 104-105, wherein R is at position 3 of the benzene ring (m).
107. The derivative of any of embodiments 104-105, wherein R is at position 4 of the benzene ring (p).
108. The derivative any of embodiments 104-107 wherein s is 9.
109. The derivative of embodiment 103, wherein P is Chem. 11.
110. The derivative of embodiment 109, wherein x is 18.
110a. The derivative of embodiment 109, wherein x is 12.
111. The derivative of any of embodiments 100-110a, wherein each L comprises linker element Chem. 15.
112. The derivative of embodiment 111, wherein each L comprises linker element Chem. 15, wherein q is 1, m is 2, and n is 0.
113. The derivative of any of embodiments 100-112, wherein each L comprises linker element Chem. 16.
114. The derivative of embodiment 113, wherein each L comprises two linker elements Chem. 16.
115. The derivative of any of embodiments 113-114, wherein k=l=1.
116. The derivative of any of embodiments 100-115, wherein each L comprises linker element Chem. 17.
116. The derivative of any of embodiments 100-115, wherein each L consists of one linker element Chem. 15 wherein q is 1 m is 2 and n is 0; and two linker elements Chem. 16 wherein k is 1 and l is 1 (Chem. 15-2×Chem. 16) interconnected via amide bonds and in the sequence indicated.

117. The derivative of any of embodiments 100-115, wherein each L consists of one linker element Chem. 15 wherein q is 1 m is 2 and n is 0; and four linker elements Chem. 16 wherein k is 1 and l is 1 (Chem. 15-4×Chem. 16) interconnected via amide bonds and in the sequence indicated.

116. The derivative of any of embodiments 100-115, wherein each L consists of one linker element Chem. 17, one linker element Chem. 15 wherein q is 1 m is 2 and n is 0; and two linker elements Chem. 16 wherein k is 1 and l is 1 (Chem. 17-Chem. 15-2×Chem. 16) interconnected via amide bonds and in the sequence indicated.

117. The derivative of any of embodiments 100-116, wherein GLP-1 comprises a peptide of formula IIb (SEQ ID NO: 27):

Xaa$_7$-Trp-Glu-Gly-Thr-Xaa$_{12}$-Thr-Ser-Asp-Xaa$_{16}$-Ser-Xaa$_8$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$, wherein Xaa$_7$ is L-histidine, (S)-2-Hydroxy-3-(1H-imidazol-4-yl)-propionic acid, D-histidine, deamino-histidine, homohistidine, N$^a$-acetyl-histidine, N$^a$-formyl-histidine, N$^a$-methyl-histidine, 3-pyridylalanine, 2-pyridylalanine, or 4-pyridylalanine;

Xaa$_{12}$ is Phe or Leu;
Xaa$_{16}$ is Val or Leu;
Xaa$_{18}$ is Ser, Arg, Val, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg or Lys;
Xaa$_{27}$ is Glu, Lys, or Leu;
Xaa$_{30}$ is Ala, Glu, or Arg;
Xaa$_{31}$ is Trp or His;
Xaa$_{33}$ is Val;
Xaa$_{34}$ is Arg, His, Asn, or Gln;
Xaa$_{35}$ is Gly or Ala;
Xaa$_{36}$ is Arg, Lys, or Gly;
Xaa$_{37}$ is Gly, Lys, Pro, or absent;
Xaa$_{38}$ is Ser, Gly, Ala, Glu, Pro, Lys, or absent; and
Xaa$_{39}$ is Ser, Gly, Ala, Glu, Pro, or absent;

with the proviso that at least two of Xaa$_{26}$, Xaa$_{27}$, Xaa$_{36}$, Xaa$_{37}$, or Xaa$_{38}$ is Lys; or a pharmaceutically acceptable salt, amide, or ester thereof.

118. The derivative of embodiment 117, wherein Xaa$_7$ is L-histidine; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Glu; Xaa$_{23}$ is Gln; Xaa$_{25}$ is Ala; Xaa$_{26}$ is Lys or Arg; Xaa$_{27}$ is Glu or Lys; Xaa$_{30}$ is Ala or Glu; Xaa$_{31}$ is Trp; Xaa$_{33}$ is Val; Xaa$_{34}$ is Arg; Xaa$_{35}$ is Gly; Xaa$_{36}$ is Lys; Xaa$_{37}$ is Gly or Lys; Xaa$_{38}$ is Glu or absent; and Xaa$_{39}$ is Gly or absent; with the proviso that at least two of Xaa$_{26}$, Xaa$_{27}$, Xaa$_{36}$, and Xaa$_{37}$ is Lys.

119. The derivative of any of embodiments 117-118, wherein GLP-1 is a peptide of formula IIb.

120. The derivative of any of embodiments 100-119, wherein the two (P-L) is attached to i) Lys26 and Lys37; ii) Lys27 and Lys36; or iii) Lys36 and Lys37.

121. The derivative of any of embodiments 100-116, wherein GLP-1 comprises a peptide of formula IIc (SEQ ID NO: 28):

Xaa$_7$-Trp-Glu-Gly-Thr-Xaa$_{12}$-Thr-Ser-Asp-Xaa$_{16}$-Ser-Xaa$_8$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$, wherein Xaa$_7$ is L-histidine, (S)-2-Hydroxy-3-(1H-imidazol-4-yl)-propionic acid, D-histidine, deamino-histidine, homohistidine, N$^a$-acetyl-histidine, N$^a$-formyl-histidine, N$^a$-methyl-histidine, 3-pyridylalanine, 2-pyridylalanine, or 4-pyridylalanine;

Xaa$_{12}$ is Phe or Leu;
Xaa$_{16}$ is Val or Leu;
Xaa$_{18}$ is Ser, Arg, Val, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg or Lys;
Xaa$_{27}$ is Glu, Lys, or Leu;
Xaa$_{30}$ is Ala, Glu, or Arg;
Xaa$_{31}$ is Trp or His;
Xaa$_{33}$ is Val;
Xaa$_{34}$ is Arg, His, Asn, or Gln;
Xaa$_{35}$ is Gly or Ala;
Xaa$_{36}$ is Arg, Lys, or Gly;
Xaa$_{37}$ is Gly, Lys, Pro, or absent;
Xaa$_{38}$ is Ser, Gly, Ala, Glu, Pro, or Lys;
Xaa$_{39}$ is Ser, Gly, Ala, Glu, or Pro;
Xaa$_{40}$ is Ser, Gly, Ala, Glu, or Pro;
Xaa$_{41}$ is Ser, Gly, Ala, Glu, or Pro; and
Xaa$_{42}$ is Lys;

with the proviso that at least two of Xaa$_{26}$, Xaa$_{27}$, Xaa$_{36}$, Xaa$_{37}$, Xaa$_{38}$, or Xaa$_{42}$ are Lys;

or a pharmaceutically acceptable salt, amide, or ester thereof.

122. The derivative of embodiments 121, wherein Xaa$_7$ is L-histidine; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Glu; Xaa$_{23}$ is Gln; Xaa$_{25}$ is Ala; Xaa$_{26}$ is Arg; Xaa$_{27}$ is Glu; Xaa$_{30}$ is Ala; Xaa$_{31}$ is Trp; Xaa$_{33}$ is Val; Xaa$_{34}$ is Arg; Xaa$_{35}$ is Gly; Xaa$_{36}$ is Arg; Xaa$_{37}$ is Gly; Xaa$_{38}$ is Lys; Xaa$_{39}$ is Gly; Xaa$_{40}$ is Gly; Xaa$_{41}$ is Ser; and Xaa$_{42}$ is Lys.

123. The derivative of any of embodiments 121-122, wherein GLP-1 is a peptide of formula IIc.

124. The derivative of any of embodiments 121-123, wherein the two (P-L) are attached to Lys38 and Lys42.

125. The derivative of any of embodiments 24-81, wherein B is present and U is 2.

126. The derivative of embodiment 125, wherein B is represented by >BL-PL, where >BL is a Branched linker and PL is an optional Pre linker.

127. The derivative of embodiment 126, wherein >BL is a tri-radical.

128. The derivative of any of embodiments 126-127, wherein >BL is represented by the Branched Linker (BL) as defined in any of embodiments 74-81.

129. The derivative of any of embodiments 126-128, wherein PL is a di-radical.

130. The derivative of any of embodiments 125-129, which has formula Ic:

(P-L)$_2$>BL-PL-GLP1;

or a pharmaceutically acceptable salt, amide, or ester thereof.

131. The derivative of any of embodiments 125-130, wherein each P is Chem. 11.

132. The derivative of embodiment 131, wherein x is 18.
133. The derivative of any of embodiments 125-132, wherein each L comprises linker element Chem. 15.
134. The derivative of any of embodiments 125-133, wherein each L comprises linker element Chem. 15, wherein q is 1, m is 2, and n is 0.
135. The derivative of any of embodiments 125-134, wherein each L comprises linker element Chem. 16.
136. The derivative of embodiment 135, wherein k=l=1.
137. The derivative of any of embodiments 125-136, wherein each L comprises linker element Chem. 17.
138. The derivative of any of embodiments 125-137, wherein each L consists of one linker element Chem. 17; one linker element Chem. 15 wherein q is 1 m is 2 and n is 0; and four linker elements Chem. 16 wherein k is 1 and l is 1 (Chem. 17-Chem. 15-4×Chem. 16) interconnected via amide bonds and in the sequence indicated.
139. The derivative of any of embodiments 125-137, wherein each L consists of one linker element Chem. 17; one linker element Chem. 15 wherein q is 1 m is 2 and n is 0; and six linker elements Chem. 16 wherein k is 1 and l is 1 (Chem. 17-Chem. 15-6×Chem. 16) interconnected via amide bonds and in the sequence indicated.
140. The derivative of any of embodiments 125-139, wherein GLP1 comprises a peptide of formula IId (SEQ ID NO: 29):
Xaa$_7$-Trp-Glu-Gly-Thr-Xaa$_{12}$-Thr-Ser-Asp-Xaa$_{16}$-Ser-Xaa$_8$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$,
wherein
Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;
Xaa$_{12}$ is Phe or Leu;
Xaa$_{16}$ is Val or Leu;
Xaa$_{18}$ is Ser, Arg, Val, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg or Lys;
Xaa$_{27}$ is Glu, Lys, or Leu;
Xaa$_{30}$ is Ala, Glu, or Arg;
Xaa$_{31}$ is Trp or His;
Xaa$_{33}$ is Val;
Xaa$_{34}$ is Arg, His, Asn, or Gln;
Xaa$_{35}$ is Gly or Ala;
Xaa$_{36}$ is Arg, Lys, or Gly;
Xaa$_{37}$ is Gly, Lys, Pro, or absent; and
Xaa$_{38}$ is Ser, Gly, Ala, Glu, Pro, Lys, or absent;
with the proviso that at least one of Xaa$_{26}$, Xaa$_{27}$, Xaa$_{36}$, Xaa$_{37}$, or Xaa$_{38}$ is Lys;
or a pharmaceutically acceptable salt, amide, or ester thereof.
141. The derivative of embodiment 140, wherein Xaa$_7$ is L-histidine; Xaa$_{12}$ is Phe; Xaa$_{16}$ is Val; Xaa$_{18}$ is Ser; Xaa$_{19}$ is Tyr; Xaa$_{20}$ is Leu; Xaa$_{22}$ is Glu; Xaa$_{23}$ is Gln; Xaa$_{25}$ is Ala; Xaa$_{26}$ is Arg; Xaa$_{27}$ is Glu; Xaa$_{30}$ is Ala; Xaa$_{31}$ is Trp; Xaa$_{33}$ is Val; Xaa$_{34}$ is Arg; Xaa$_{35}$ is Gly; Xaa$_{36}$ is Arg; Xaa$_{37}$ is Lys or Pro; and Xaa$_{38}$ is Lys or absent; with the proviso that at least one of Xaa$_{37}$ and Xaa$_{38}$ is Lys.
142. The derivative of any of embodiments 140-141, wherein GLP-1 is a peptide of formula IId.
143. The derivative of any of embodiments 125-142, wherein (P-L) is attached to Lys37 or Lys38.
144. The derivative of any of embodiments 125-143, wherein BL is Chem. 19, wherein u and v independently represents an integer in the range of 0-5, with the provisos that when u is 0 v is an integer in the range of 1-5, and when v is 0 u is an integer in the range of 1-5.
145. The derivative of embodiment 144, wherein u is 0 and v is 4.
146. The derivative of embodiment 144, wherein u is 4 and v is 0.
147. The derivative of any of embodiments 125-146, wherein PL when present comprises Chem. 16.
148. The derivative of embodiment 147, wherein PL comprises from 0 to 2 times of linker element Chem. 16.
149. The derivative of any of embodiments 147-148, wherein each of k and l, independently, is 1-5.
150. The derivative of any of embodiments 147-149, wherein each of k and l is 1.
151. The derivative of any of embodiments 147-150, wherein PL comprises 0 times Chem. 16, viz. does not comprise Chem. 16.
152. The derivative of any of embodiments 147-151, wherein PL is absent.
153. The derivative of any of embodiments 125-152, which has formula Id:

$$(P-L)_2\text{>BL-GLP1};$$

or a pharmaceutically acceptable salt, amide, or ester thereof.
154. The derivative of any of embodiments 147-150, wherein PL is present and non-optional (i.e., mandatory).
155. The derivative of any of embodiments 147-150 and 154, wherein PL comprises two times Chem. 16.
156. The derivative of any of embodiments 147-150 and 154-155, wherein PL consists of two times Chem. 16.
157. The derivative of any of embodiments 125-143, wherein BL is Chem. 20, wherein each w represents an integer in the range of 0-2.
158. The derivative of embodiment 157, wherein w is 1.
159. The derivative of any of embodiments 157-158, wherein PL is present.
160. The derivative of any of embodiments 157-160, wherein PL comprises Chem. 16.
161. The derivative of any of embodiments 159-160, wherein PL comprises two times linker element Chem. 16.
162. The derivative of any of embodiments 159-160, wherein PL consists of two times linker element Chem. 16.
163. The derivative of any of embodiments 160-162, wherein each of k and l, independently, is 1-5.
163. The derivative of any of embodiments 160-163, wherein each of k and l is 1.
164. The derivative of any of embodiments 24-163, wherein GLP1 is selected from SEQ ID NO: 5, SEQ ID NO: 7, SEQ ID NO: 9, and SEQ ID NO: 11; or a pharmaceutically acceptable salt, amide, or ester thereof.
165. A derivative selected from Chem. 21, Chem. 22, Chem. 23, Chem. 24, and Chem. 25; or a pharmaceutically acceptable salt, amide, or ester thereof.
166. The derivative of embodiment 164, which is a derivative of any of embodiments 1-165.
167. The derivative of any of embodiments 165-166, which is the compound of Examples 1, 2, 3, 4, or 5.
168. The derivative of any of embodiments 1-167 which is a GLP-1 derivative.

169. A GLP-1 analogue selected from SEQ ID NO: 5, SEQ ID NO: 7, SEQ ID NO: 9, and SEQ ID NO: 11; or a pharmaceutically acceptable salt, amide, or ester thereof.

170. A compound comprising, or having, amino acids 1-275 of SEQ ID NO: 15, or a pharmaceutically acceptable salt, amide, or ester thereof.

170a. A compound comprising, or having, amino acids 276-550 of SEQ ID NO: 15, or a pharmaceutically acceptable salt, amide, or ester thereof.

170b. A compound comprising, or having, SEQ ID NO: 15.

170c. A compound which is a dimer of i) two compounds of embodiment 170, ii) two compounds of embodiment 170a, iii) one compound of embodiment 170 and one compound of embodiment 170a.

170d. The compound of any of embodiments 170b-170c, which has Cys-Cys bonds between the two Cys residues at position 55, and the two Cys residues at position 58.

171. The derivative or analogue of any of embodiments 1-169, which is a GLP-1 receptor agonist.

172. The derivative or analogue of any of embodiments 1-169 and 171, which is a full GLP-1 receptor agonist.

173. The derivative or analogue of any of embodiments 1-169 and 171-172, which is biologically active in vitro.

174. The derivative or analogue of any of embodiments 1-169 and 171-173, which is potent in vitro.

175. The derivative or analogue of any of embodiments 1-169 and 171-174, which is capable of activating the human GLP-1 receptor.

176. The derivative or analogue of any of embodiments 1-169 and 171-175, which is capable of activating the human GLP-1 receptor in an assay with whole cells expressing the human GLP-1 receptor, wherein the assay is performed in the absence of HSA (0% HSA).

177. The derivative or analogue of any of embodiments 1-169 and 171-176, where the response of the human GLP-1 receptor is measured in a reporter gene assay, such as the assay of Example 15.

178. The derivative or analogue of any of embodiments 171-177, wherein the GLP-1 receptor agonism, the in vitro biological activity, the in vitro potency, or the capability of activating the human GLP-1 receptor, respectively, is determined essentially as described in Example 15.

179. The derivative or analogue of any of embodiments 1-169 and 171-178, which has an in vitro potency corresponding to an $EC_{50}$ of 300 pM or below.

180. The derivative or analogue of any of embodiments 1-169 and 171-179, which has an in vitro potency corresponding to an $EC_{50}$ of 200 pM or below.

181. The derivative or analogue of any of embodiments 1-169 and 171-180, which has an in vitro potency corresponding to an $EC_{50}$ of 150 pM or below.

182. The derivative or analogue of any of embodiments 1-169 and 171-181, which has an in vitro potency corresponding to an $EC_{50}$ of 125 pM or below.

183. The derivative or analogue of any of embodiments 1-169 and 171-182, which has an in vitro potency corresponding to an $EC_{50}$ of 100 pM or below.

184. The derivative or analogue of any of embodiments 1-169 and 171-183, which has an in vitro potency corresponding to an $EC_{50}$ of 75 pM or below.

185. The derivative or analogue of any of embodiments 1-169 and 171-184, which has an in vitro potency corresponding to an $EC_{50}$ of 50 pM or below.

186. The derivative or analogue of any of embodiments 1-169 and 171-185, which has an in vitro potency corresponding to an $EC_{50}$ of 30 pM or below.

187. The derivative or analogue of any of embodiments 179-186, wherein the $EC_{50}$ is determined essentially as described in Example 15.

188. The derivative or analogue of any of embodiments 1-169 and 171-187, which has an in vitro potency corresponding to an $EC_{50}$ of less than 60 times the $EC_{50}$ of semaglutide, wherein the $EC_{50}$ of semaglutide is determined in the same way as the $EC_{50}$ of the derivative.

189. The derivative or analogue of any of embodiments 1-169 and 171-188, which has an in vitro potency corresponding to an $EC_{50}$ of less than 30 times the $EC_{50}$ of semaglutide, wherein the $EC_{50}$ of semaglutide is determined in the same way as the $EC_{50}$ of the derivative.

190. The derivative or analogue of any of embodiments 1-169 and 171-189, which has an in vitro potency corresponding to an $EC_{50}$ of less than 8 times the $EC_{50}$ of semaglutide, wherein the $EC_{50}$ of semaglutide is determined in the same way as the $EC_{50}$ of the derivative.

191. The derivative or analogue of any of embodiments 1-169 and 171-190, which has an in vitro potency corresponding to an $EC_{50}$ of less than 6 times the $EC_{50}$ of semaglutide, wherein the $EC_{50}$ of semaglutide is determined in the same way as the $EC_{50}$ of the derivative.

192. The derivative or analogue of any of embodiments 1-169 and 171-191, which has an in vitro potency corresponding to an $EC_{50}$ of less than 3 times the $EC_{50}$ of semaglutide, wherein the $EC_{50}$ of semaglutide is determined in the same way as the $EC_{50}$ of the derivative.

193. The derivative or analogue of any of embodiments 1-169 and 171-192, which has an in vitro potency corresponding to an $EC_{50}$ of less than 2 times the $EC_{50}$ of semaglutide, wherein the $EC_{50}$ of semaglutide is determined in the same way as the $EC_{50}$ of the derivative.

194. The derivative or analogue of any of embodiments 1-169 and 171-193, which has an in vitro potency corresponding to an $EC_{50}$ of less than or equal to the $EC_{50}$ of semaglutide, wherein the $EC_{50}$ of semaglutide is determined in the same way as the $EC_{50}$ of the derivative.

195. The derivative or analogue of any of embodiments 188-194, wherein the $EC_{50}$ is determined essentially as described in Example 15.

196. The derivative or analogue of any of embodiments 1-169 and 171-195, which is capable of binding to the GLP-1 receptor.

197. The derivative or analogue of any of embodiments 1-169 and 171-196, which is capable of binding to the GLP-1 receptor at a low concentration of HSA (max. 0.001% (w/v) final assay concentration).

198. The derivative or analogue of any of embodiments 1-169 and 171-195, which is capable of binding to the GLP-1 receptor at a high concentration of HSA (2.0% (w/v) final assay concentration).

199. The derivative or analogue of any of embodiments 196-198, wherein the binding to the human GLP-1 receptor is measured in a competitive binding assay, such as the assay of Example 16.

200. The derivative or analogue of any of embodiments 196-199, wherein the binding to the human GLP-1 receptor in vitro is determined essentially as described in Example 16.

201. The derivative or analogue of any of embodiments 1-169 and 171-200, which at a low concentration of HSA is capable of binding to the human GLP-1 receptor with an $IC_{50}$ of 20 nM or below.

202. The derivative or analogue of any of embodiments 1-169 and 171-201, which at a low concentration of HSA is capable of binding to the human GLP-1 receptor with an $IC_{50}$ of 10 nM or below.

203. The derivative or analogue of any of embodiments 1-169 and 171-202, which at a low concentration of HSA is capable of binding to the human GLP-1 receptor with an $IC_{50}$ of 4.0 nM or below.

204. The derivative or analogue of any of embodiments 1-169 and 171-203, which at a low concentration of HSA is capable of binding to the human GLP-1 receptor with an $IC_{50}$ of 2.0 nM or below.

205. The derivative or analogue of any of embodiments 1-169 and 171-204, which at a low concentration of HSA is capable of binding to the human GLP-1 receptor with an $IC_{50}$ of 1.0 nM or below.

206. The derivative or analogue of any of embodiments 1-169 and 171-205, which at a low concentration of HSA is capable of binding to the human GLP-1 receptor with an $IC_{50}$ of 0.50 nM or below.

207. The derivative or analogue of any of embodiments 201-206, wherein the $IC_{50}$ is determined essentially as described in Example 16, in a reaction with max. 0.001% (w/v) HSA (final assay concentration).

208. The derivative or analogue of any of embodiments 1-169 and 171-207, which at a low concentration of HSA is capable of binding to the human GLP-1 receptor with an $IC_{50}$ of less than 35 times the $IC_{50}$ of semaglutide, wherein the $IC_{50}$ of semaglutide is determined in the same way as the $IC_{50}$ of the derivative.

209. The derivative or analogue of any of embodiments 1-169 and 171-208, which at a low concentration of HSA is capable of binding to the human GLP-1 receptor with an $IC_{50}$ of less than 20 times the $IC_{50}$ of semaglutide, wherein the $IC_{50}$ of semaglutide is determined in the same way as the $IC_{50}$ of the derivative.

210. The derivative or analogue of any of embodiments 1-169 and 171-209, which at a low concentration of HSA is capable of binding to the human GLP-1 receptor with an $IC_{50}$ of less than 8 times the $IC_{50}$ of semaglutide, wherein the $IC_{50}$ of semaglutide is determined in the same way as the $IC_{50}$ of the derivative.

211. The derivative or analogue of any of embodiments 1-169 and 171-210, which at a low concentration of HSA is capable of binding to the human GLP-1 receptor with an $IC_{50}$ of less than 4 times the $IC_{50}$ of semaglutide, wherein the $IC_{50}$ of semaglutide is determined in the same way as the $IC_{50}$ of the derivative.

212. The derivative or analogue of any of embodiments 1-169 and 171-211, which at a low concentration of HSA is capable of binding to the human GLP-1 receptor with an $IC_{50}$ of less than 3 times the $IC_{50}$ of semaglutide, wherein the $IC_{50}$ of semaglutide is determined in the same way as the $IC_{50}$ of the derivative.

213. The derivative or analogue of any of embodiments 1-169 and 171-212, which at a low concentration of HSA is capable of binding to the human GLP-1 receptor with an $IC_{50}$ of less than 2 times the $IC_{50}$ of semaglutide, wherein the $IC_{50}$ of semaglutide is determined in the same way as the $IC_{50}$ of the derivative.

214. The derivative or analogue of any of embodiments 1-169 and 171-213, which at a low concentration of HSA is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

215. The derivative or analogue of any of embodiments 1-169 and 171-214, which at a low concentration of HSA is capable of binding to the human GLP-1 receptor with an $IC_{50}$ of less than 0.50 times the $IC_{50}$ of semaglutide, wherein the $IC_{50}$ of semaglutide is determined in the same way as the $IC_{50}$ of the derivative.

216. The derivative or analogue of any of embodiments 208-215, wherein the $IC_{50}$ is determined essentially as described in Example 16, in a reaction with max. 0.001% (w/v) HSA (final assay concentration).

217. The derivative or analogue of any of embodiments 1-169 and 171-216, which at 2.0% (w/v) HSA (final assay concentration) is capable of binding to the human GLP-1 receptor with an $IC_{50}$ of 800 nM or below.

218. The derivative or analogue of any of embodiments 1-169 and 171-217, which at 2.0% (w/v) HSA (final assay concentration) is capable of binding to the human GLP-1 receptor with an $IC_{50}$ of 450 nM or below.

219. The derivative or analogue of any of embodiments 1-169 and 171-218, which at 2.0% (w/v) HSA (final assay concentration) is capable of binding to the human GLP-1 receptor with an $IC_{50}$ of 200 nM or below.

220. The derivative or analogue of any of embodiments 1-169 and 171-219, which at 2.0% (w/v) HSA (final assay concentration) is capable of binding to the human GLP-1 receptor with an $IC_{50}$ of 100 nM or below.

221. The derivative or analogue of any of embodiments 1-169 and 171-220, which at 2.0% (w/v) HSA (final assay concentration) is capable of binding to the human GLP-1 receptor with an $IC_{50}$ of 20 nM or below.

222. The derivative or analogue of any of embodiments 1-169 and 171-221, which at 2.0% (w/v) HSA (final assay concentration) is capable of binding to the human GLP-1 receptor with an $IC_{50}$ of 10 nM or below.

223. The derivative or analogue of any of embodiments 217-222, wherein the $IC_{50}$ is determined essentially as described in Example 16, in a reaction with 2.0% (w/v) HSA (final assay concentration).

224. The derivative or analogue of any of embodiments 1-169 and 171-223, which at 2.0% (w/v)HSA (final assay concentration) is capable of binding to the human GLP-1 receptor with an $IC_{50}$ of less than two times the $IC_{50}$ of semaglutide, wherein the $IC_{50}$ of semaglutide is determined in the same way as the $IC_{50}$ of the derivative.

225. The derivative or analogue of any of embodiments 1-169 and 171-223, which at 2.0% (w/v) HSA (final assay concentration) is capable of binding to the human GLP-1 receptor with an $IC_{50}$ of less than the $IC_{50}$ of semaglutide, wherein the $IC_{50}$ of semaglutide is determined in the same way as the $IC_{50}$ of the derivative.

226. The derivative or analogue of any of embodiments 1-169 and 171-223, which at 2.0% (w/v) HSA (final assay concentration) is capable of binding to the human GLP-1 receptor with an $IC_{50}$ of less than 0.30 times the $IC_{50}$ of semaglutide, wherein the $IC_{50}$ of semaglutide is determined in the same way as the $IC_{50}$ of the derivative.

227. The derivative or analogue of any of embodiments 1-169 and 171-223, which at 2.0% (w/v) HSA (final assay concentration) is capable of binding to the human GLP-1 receptor with an $IC_{50}$ of less than 0.15 times the $IC_{50}$ of semaglutide, wherein the $IC_{50}$ of semaglutide is determined in the same way as the $IC_{50}$ of the derivative.

228. The derivative or analogue of any of embodiments 1-169 and 171-223, which at 2.0% (w/v) HSA (final assay concentration) is capable of binding to the human GLP-1 receptor with an $IC_{50}$ of less than 0.10 times the $IC_{50}$ of semaglutide, wherein the $IC_{50}$ of semaglutide is determined in the same way as the $IC_{50}$ of the derivative.

229. The derivative or analogue of any of embodiments 224-228, wherein the $IC_{50}$ is determined essentially as described in Example 16, in a reaction with 2.0% (w/v) HSA (final assay concentration).

230. A method of preparing a derivative or analogue of any of embodiments 1-169 and 171-229, which comprises the step of recombinantly producing a GLP-1 analogue having Trp at a position corresponding to position 8 of GLP-1(7-37) (SEQ ID NO: 1).

231. The method of embodiment 230, which further comprises the step of purifying the recombinantly produced GLP-1 analogue.

232. The method of any of embodiments 230-231, which further comprises the step of attaching the substituent to a Lys residue of the GLP-1 analogue, whereby a derivative of the GLP-1 analogue is produced.

233. The method of embodiment 232, wherein one or two substituents are attached.

234. The method of embodiment 233, wherein one substituent is attached to one Lys residue.

235. The method of embodiment 233, wherein two substituents are attached to two Lys residues, one substituent to each Lys residue.

236. The method of embodiment 233, wherein two substituents are attached to one Lys residue, via the Branching group (B).

237. The method of any of embodiments 232-237, which further comprises the step of purifying the GLP-1 derivative.

238. A pharmaceutical composition comprising a derivative or an analogue according to any of embodiments 1-169 and 171-229, and a pharmaceutically acceptable excipient.

239. A derivative or an analogue according to any of embodiments 1-169 and 171-229, for use as a medicament.

240. A derivative or an analogue according to any of embodiments 1-169 and 171-229, for use in (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or B-cell mass, and/or for restoring glucose sensitivity to B-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

241. Use of a derivative or an analogue according to any of embodiments 1-169 and 171-229, in the manufacture of a medicament for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse.

242. A method for (i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of cognitive disorders and/or neurodegenerative disorders, such as Alzheimer's disease, Parkinson's disease, and/or multiple sclerosis;

(v) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(vi) prevention and/or treatment of diabetic complications, such as angiopathy; neuropathy, including peripheral neuropathy; nephropathy; and/or retinopathy;

(vii) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(viii) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis obliterens), diastolic dysfunction, and/or systolic dysfunction; and/or reduction of blood pressure, such as reduction of systolic blood pressure;

(ix) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(x) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, such as cerebral ischemia, cerebral haemorrhage, and/or traumatic brain injury;

(xiii) prevention and/or treatment of sleep apnoea; and/or (xiv) prevention and/or treatment of abuse, such as alcohol abuse and/or drug abuse;

wherein a pharmaceutically active amount of a derivative or an analogue according to any of embodiments 1-169 and 171-229, is administered.

In some embodiments the derivative of the invention is not selected from Chem. 21, Chem. 22, Chem. 23, Chem. 24, and Chem. 25; and is also not a pharmaceutically acceptable salt, amide, or ester thereof.

In some embodiments the GLP-1 analogue of the invention is not selected from SEQ ID NO: 5, SEQ ID NO: 7, SEQ ID NO: 9, and SEQ ID NO: 11; and is also not a pharmaceutically acceptable salt, amide, or ester thereof.

Still Further Particular Embodiments i). A derivative comprising a GLP-1 analogue having a Trp at a position corresponding to position 8 of GLP-1(7-37) (SEQ ID NO: 1) and wherein a substituent comprising at least eight consecutive —$CH_2$-groups and at least one functional group (FG) with a pKa<7 is attached to a Lys residue of the GLP-1 analogue.

ii). The derivative of embodiment i), wherein the at least one FG is independently selected from Chem. 1, Chem. 2, and Chem. 4:

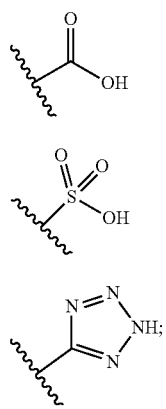

Chem. 1

Chem. 2

Chem. 4 or a pharmaceutically acceptable salt, amide, or ester thereof.

iii). The derivative of any of embodiments i)-ii), which has formula I:

(P-L)$_U$-B-GLP1, wherein GLP1 is a GLP-1 analogue having a Trp at a position corresponding to position 8 of GLP-1(7-37) (SEQ ID NO: 1), (P-L) is a substituent attached to a Lys residue of the GLP-1 analogue via an optional Branching group (B) and comprising a Protracting moiety (P) and a Linker (L), U represents the number of substituents (P-L) in the derivative and is 1 or 2;

or a pharmaceutically acceptable salt, amide, or ester thereof.

iv). The derivative of any of embodiments i)-iii), wherein the GLP-1 analogue comprises a peptide of formula II (SEQ ID NO: 25):

Xaa$_7$-Trp-Glu-Gly-Thr-Xaa$_{12}$-Thr-Ser-Asp-Xaa$_{16}$-Ser-Xaa$_8$-Xaa$_{19}$-Xaa$_{20}$-Glu-Xaa$_{22}$-Xaa$_{23}$-Ala-Xaa$_{25}$-Xaa$_{26}$-Xaa$_{27}$-Phe-Ile-Xaa$_{30}$-Xaa$_{31}$-Leu-Xaa$_{33}$-Xaa$_{34}$-Xaa$_{35}$-Xaa$_{36}$-Xaa$_{37}$-Xaa$_{38}$-Xaa$_{39}$-Xaa$_{40}$-Xaa$_{41}$-Xaa$_{42}$, wherein Xaa$_7$ is L-histidine, (S)-2-Hydroxy-3-(1H-imidazol-4-yl)-propionic acid, D-histidine, deamino-histidine, homohistidine, N$^\alpha$-acetyl-histidine, N$^\alpha$-formyl-histidine, N$^\alpha$-methyl-histidine, 3-pyridylalanine, 2-pyridylalanine, or 4-pyridylalanine;

Xaa$_{12}$ is Phe or Leu;
Xaa$_{16}$ is Val or Leu;
Xaa$_{18}$ is Ser, Arg, Val, or Leu;
Xaa$_{19}$ is Tyr or Gln;
Xaa$_{20}$ is Leu or Met;
Xaa$_{22}$ is Gly or Glu;
Xaa$_{23}$ is Gln, Glu, or Arg;
Xaa$_{25}$ is Ala or Val;
Xaa$_{26}$ is Arg or Lys;
Xaa$_{27}$ is Glu, Lys, or Leu;
Xaa$_{30}$ is Ala, Glu, or Arg;
Xaa$_{31}$ is Trp or His;
Xaa$_{33}$ is Val;
Xaa$_{34}$ is Arg, His, Asn, or Gln;
Xaa$_{35}$ is Gly or Ala;
Xaa$_{36}$ is Arg, Lys, or Gly;
Xaa$_{37}$ is Gly, Lys, Pro, or absent;
Xaa$_{38}$ is Ser, Gly, Ala, Glu, Pro, Lys, or absent;
Xaa$_{39}$ is Ser, Gly, Ala, Glu, Pro, or absent;
Xaa$_{40}$ is Ser, Gly, Ala, Glu, Pro, or absent;
Xaa$_{41}$ is Ser, Gly, Ala, Glu, Pro, or absent; and
Xaa$_{42}$ is Lys or absent;

with the proviso that if one of Xaa$_{37}$, Xaa$_{38}$, Xaa$_{39}$, Xaa$_{40}$, Xaa$_{41}$, or Xaa$_{42}$ is absent then each subsequent amino acid residue is also absent; and with the proviso that at least one of Xaa$_{26}$, Xaa$_{27}$, Xaa$_{36}$, Xaa$_{37}$, Xaa$_{38}$, or Xaa$_{42}$ is Lys;

or a pharmaceutically acceptable salt, amide, or ester thereof.

v). The derivative of any of embodiments i)-iv), wherein one or two of Xaa$_{26}$, Xaa$_{27}$, Xaa$_{36}$, Xaa$_{37}$, Xaa$_{38}$, or Xaa$_{42}$ is/are Lys; and wherein one or two substituents is/are attached to the epsilon amino group of the one or two Lys residues.

vi). The derivative of any of embodiments i)-v), wherein each substituent comprises (I) a Protracting moiety (P) selected from Chem. 10, Chem. 11, Chem. 12, Chem. 13, and Chem. 14:

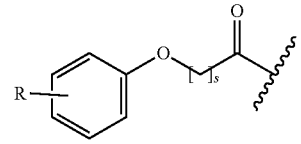

Chem. 10

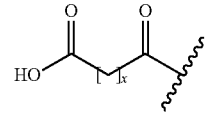

Chem. 11

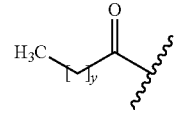

Chem. 12

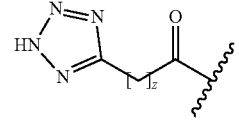

Chem. 13

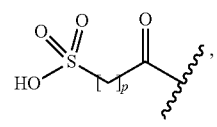

Chem. 14 and (II) a Linker (L) comprising at least one linker element selected from Chem. 15, Chem. 16, Chem. 17, and Chem. 18:

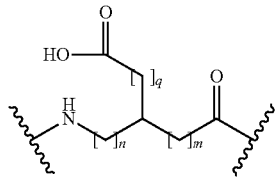

Chem. 15

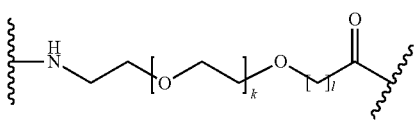

Chem. 16

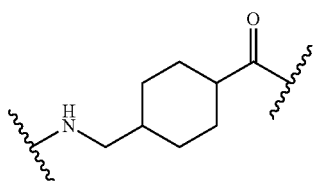

Chem. 17

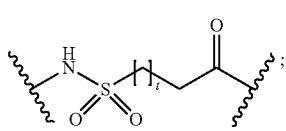

Chem. 18 wherein
R is —COOH;
each of s, x, y, z, and p independently represents an integer in the range of 8-20;
each of n, m, and q independently represents an integer in the range of 0-4; and
each of k, l, and t independently represents an integer in the range of 1-5; and (III) wherein the Branching group (B) if present comprises a Branched linker (BL) selected from Chem. 19 and Chem. 20:

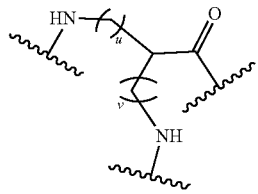

Chem. 19

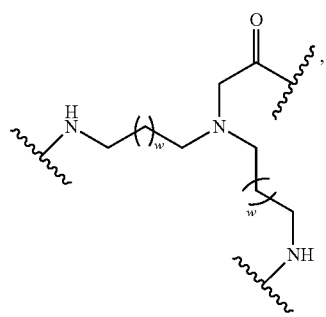

Chem. 20 wherein u and v independently represents an integer in the range of 0-5 and each w represents an integer in the range of 0-2, with the provisos that when u is 0 v is an integer in the range of 1-5, and when v is 0 u is an integer in the range of 1-5.

vii). The derivative of any of embodiments iii)-v), which has formula Ia: (P-L)-GLP1; or a pharmaceutically acceptable salt, amide, or ester thereof.

iix). The derivative of any of embodiments iii)-v), which has formula Ib: (P-L)$_2$-GLP1; or a pharmaceutically acceptable salt, amide, or ester thereof.

ix). The derivative of any of embodiments iii)-v), which has formula Ic: (P-L)$_2$>BL-PL-GLP1, wherein (I) >BL is a Branched linker as defined in claim 5, and (II) PL is a Pre linker which comprises Chem. 16:

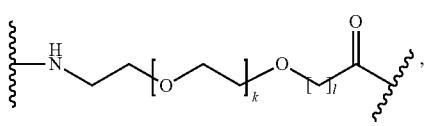

wherein each of k and l independently represents an integer in the range of 1-5; or a pharmaceutically acceptable salt, amide, or ester thereof.

x). The derivative of any of embodiments iii)-v), which has formula Id: (P-L)$_2$>BL-GLP1, wherein >BL is a Branched linker as defined in claim 5;

or a pharmaceutically acceptable salt, amide, or ester thereof.

xi). A derivative selected from the following:

N{Epsilon-36}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl], N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Trp8,Glu22,Arg26,Arg34,Lys36,Lys37]-GLP-1-(7-37)-peptide Chem. 21

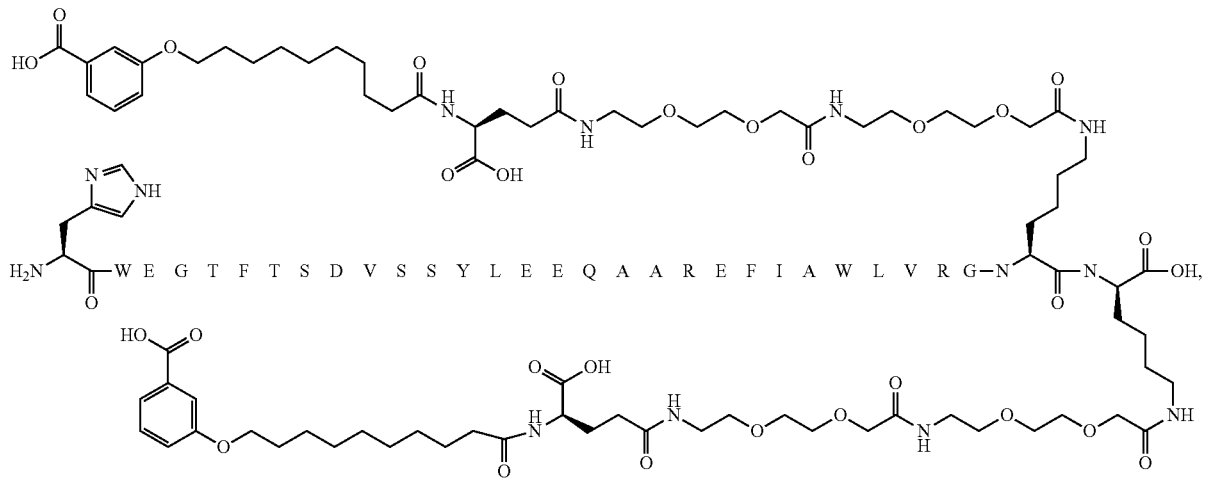

this compound is a derivative of the GLP-1 analogue of SEQ ID NO: 5.

N{Epsilon-26}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Trp8,Arg34]-GLP-1-(7-37)-peptide

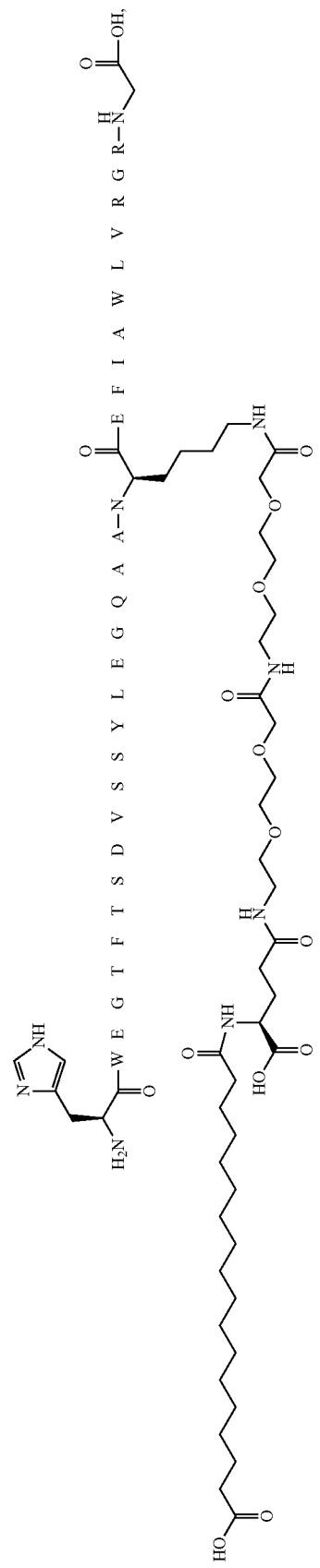
Chem. 22 this compound is a derivative of the GLP-1 analogue of SEQ ID NO: 7.

N{Epsilon-27}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]eth oxy]acetyl],N{Epsilon-36}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]eth oxy]acetyl]-[Trp8,Glu22,Arg26,Lys27,Glu30,Arg34,Lys36]-GLP-1-(7-37)-peptidyl-Glu-Gly Chem. 23
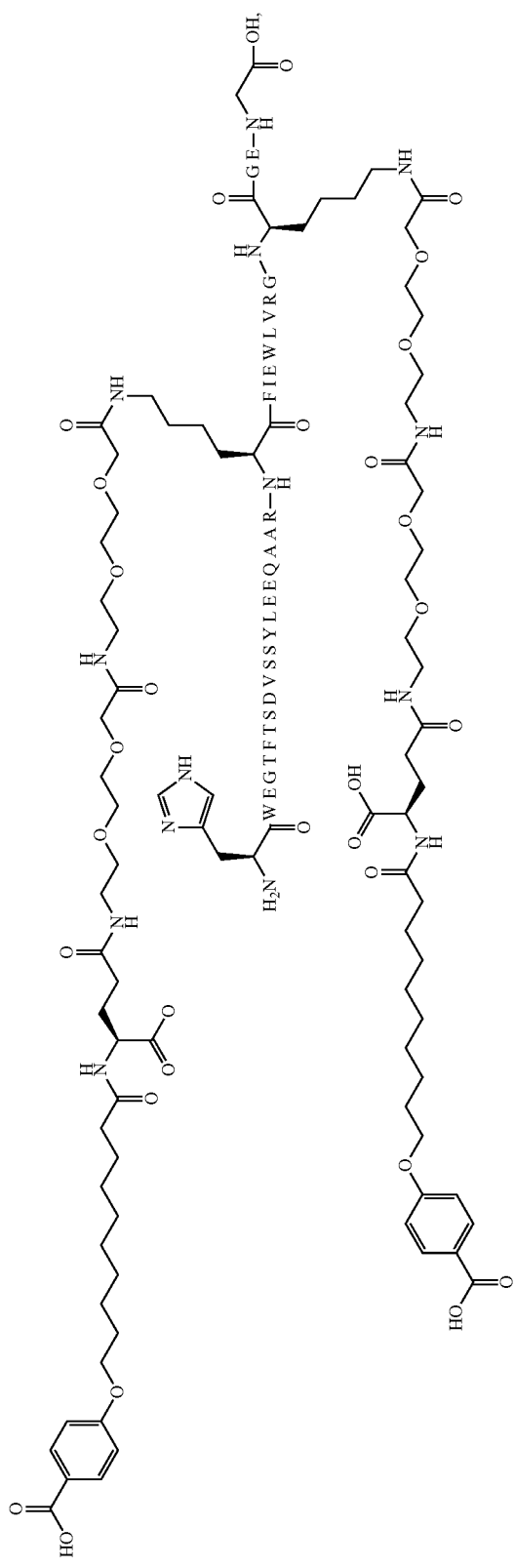

this compound is a derivative of the GLP-1 analogue of SEQ ID NO: 9.

N{Epsilon-26}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]eth oxy]acetyl],N{Epsilon-37}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]eth oxy]acetyl]-[Trp8,Arg34,Lys37]-GLP-1-(7-37)-peptide Chem. 24
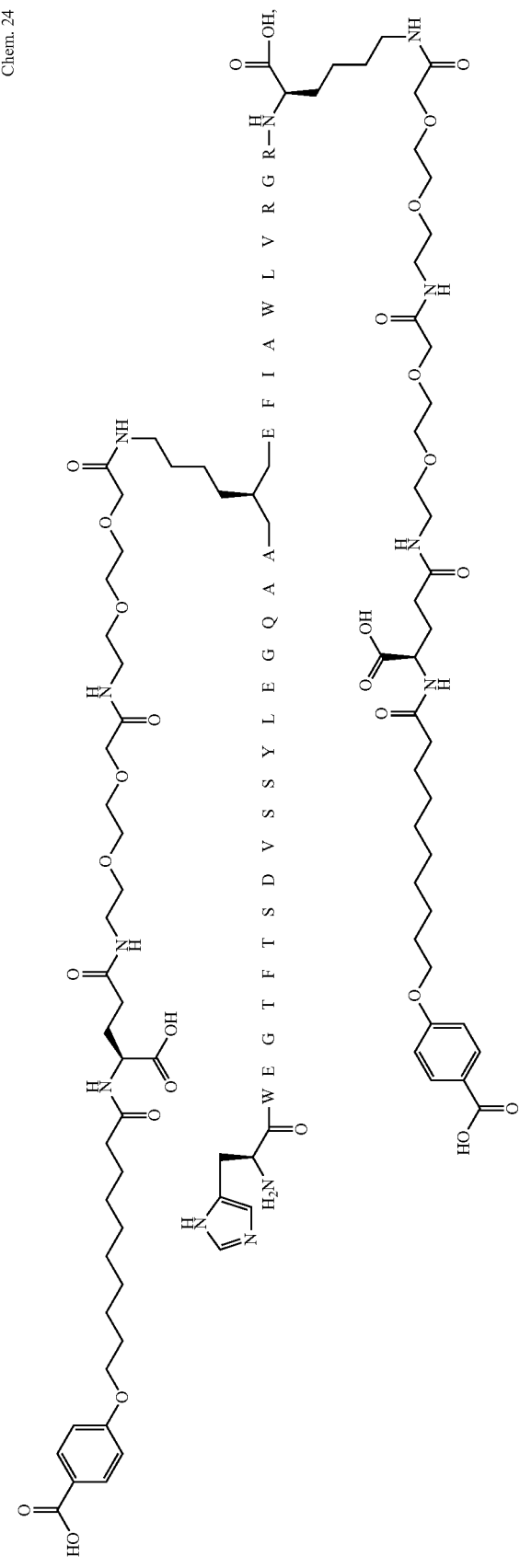

this compound is a derivative of the GLP-1 analogue of SEQ ID NO: 11, and

N{Epsilon-26}-[(4S)-4-carboxy-4-(hexadecanoy-lamino)butanoyl]-[Trp8,Arg34]-GLP-1-(7-37)-peptide Chem. 25

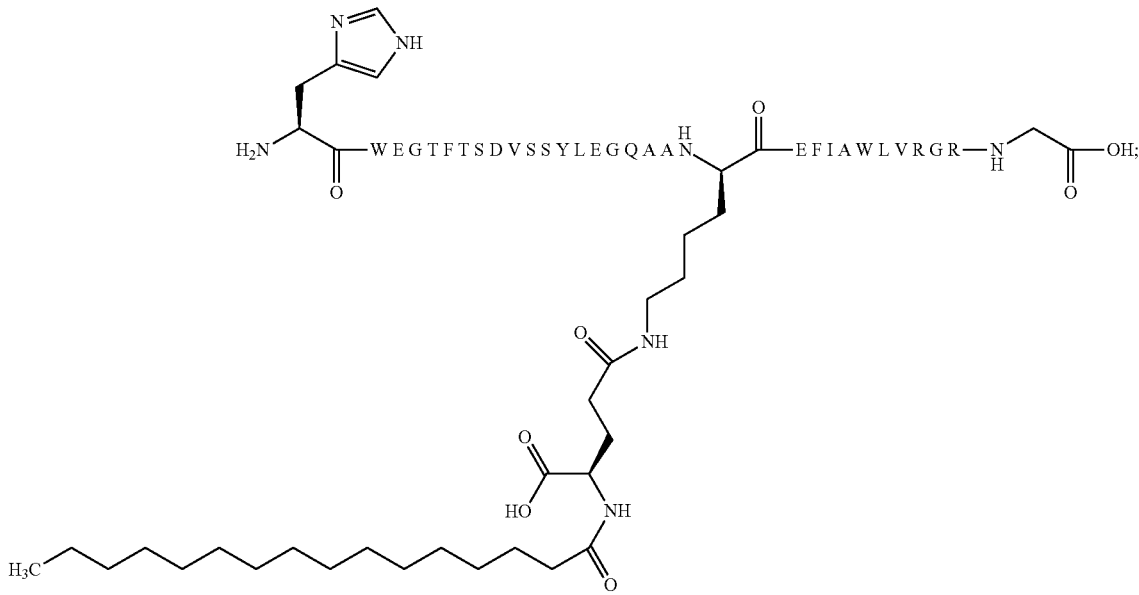

this compound is a derivative of the GLP-1 analogue of SEQ ID NO: 7, or a pharmaceutically acceptable salt, amide, or ester thereof.

xii). A GLP-1 analogue selected from SEQ ID NO: 5, SEQ ID NO: 7, SEQ ID NO: 9, and SEQ ID NO: 11; or a pharmaceutically acceptable salt, amide, or ester thereof.

xiii). A pharmaceutical composition comprising a derivative or an analogue according to any of embodiments i)-xii), and a pharmaceutically acceptable excipient.

xiv). A derivative or an analogue according to any of embodiments i)-xii), for use as a medicament.

xv). A derivative or an analogue according to any of embodiments i)-xii), for use in (I) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(II) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(III) improving β-cell function, such as decreasing β-cell apoptosis, increasing β-cell function and/or β-cell mass, and/or for restoring glucose sensitivity to β-cells;

(IV) prevention and/or treatment of cognitive disorders and/or neurodegenerative disorders, such as Alzheimer's disease, Parkinson's disease, and/or multiple sclerosis;

(V) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(VI) prevention and/or treatment of diabetic complications, such as angiopathy; neuropathy, including peripheral neuropathy; nephropathy; and/or retinopathy;

(VII) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(VIII) prevention and/or treatment of cardiovascular diseases, such as syndrome X, atherosclerosis, myocardial infarction, coronary heart disease, reperfusion injury, stroke, cerebral ischemia, an early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent claudication (atheroschlerosis oblitterens), diastolic dysfunction, and/or systolic dysfunction; and/or reduction of blood pressure, such as reduction of systolic blood pressure;

(IX) prevention and/or treatment of gastrointestinal diseases, such as inflammatory bowel disease, short bowel syndrome, or Crohn's disease or colitis; dyspepsia, and/or gastric ulcers; and/or inflammation, such as psoriasis, psoriactic arthritis, rheumatoid arthritis, and/or systemic lupus erythematosus;

(X) prevention and/or treatment of critical illness, such as treatment of a critically ill patient, a critical illness polynephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(XI) prevention and/or treatment of polycystic ovary syndrome (PCOS);

(XII) prevention and/or treatment of cerebral disease, such as cerebral ischemia, cerebral haemorrhage, and/or traumatic brain injury;

(XIII) prevention and/or treatment of sleep apnoea; and/or (XIV) prevention and/or treatment of abuse, such as alcohol abuse and/or drug abuse.

EXAMPLES

This experimental part starts with a list of abbreviations, and is followed by a section including general methods for synthesising and characterising analogues and derivatives of the invention. Then follows a number of examples which relate to the preparation of specific GLP-1 derivatives, and at the end a number of examples have been included relating to the activity and properties of these analogues and derivatives (section headed pharmacological methods).

The examples serve to illustrate the invention.

LIST OF ABBREVIATIONS

Aib: α-aminoisobutyric acid (2-Aminoisobutyric acid)
Ado: 8-amino-3,6-dioxaoctanoic acid
API: Active Pharmaceutical Ingredient
AUC: Area Under the Curve
BG: Blood Glucose
BHK Baby Hamster Kidney
BW: Body Weight
Boc: t-butyloxycarbonyl
Bom: benzyloxymethyl
BSA: Bovine serum albumin
Bzl: benzyl
C20 diacid: icosanedioic acid
CAS: Chemical Abstracts Service
Clt: 2-chlorotrityl
collidine: 2,4,6-trimethylpyridine
DCM: dichloromethane
Dde: 1-(4,4-dimethyl-2,6-dioxocyclohexylidene)ethyl
DIC: diisopropylcarbodiimide
DIPEA: diisopropylethylamine
DMAP: 4-dimethylaminopyridine
DMEM: Dulbecco's Modified Eagle's Medium (DMEM)
EDTA: ethylenediaminetetraacetic acid
EGTA: ethylene glycol tetraacetic acid
FCS: Fetal Calf Serum
Fmoc: 9-fluorenylmethyloxycarbonyl
HATU: (0-(7-azabenzotriazol-1-yl)-1,1,3,3-tetramethyluronium hexa fluorophosphate)
HBTU: (2-(1H-benzotriazol-1-yl-)-1,1,3,3 tetramethyluronium hexafluorophosphate)
HEPES: 4-(2-hydroxyethyl)-1-piperazineethanesulfonic acid
HFIP 1,1,1,3,3,3-hexafluoro-2-propanol or hexafluoroisopropanol
HOAt: 1-hydroxy-7-azabenzotriazole
HOBt: 1-hydroxybenzotriazole
HPLC: High Performance Liquid Chromatography
HSA: Human Serum Albumin
IBMX: 3-isobutyl-1-methylxanthine
Imp: Imidazopropionic acid (3-(Imidazol-5-yl)propanoic acid) (also called deamino-histidine, or deamino-His)
i.v. intravenously
ivDde: 1-(4,4-dimethyl-2,6-dioxocyclohexylidene)-3-methylbutyl
IVGTT: Intravenous Glucose Tolerance Test
LCMS: Liquid Chromatography Mass Spectroscopy
LYD: Landrace Yorkshire Duroc
MALDI-MS: See MALDI-TOF MS
MALDI-TOF MS: Matrix-Assisted Laser Desorption/Ionisation Time of Flight Mass Spectroscopy
MeOH: methanol
Mmt: 4-methoxytrityl
Mtt: 4-methyltrityl
NMP: N-methyl pyrrolidone
OtBu: tert butyl ester
Oxyma Pure®: Cyano-hydroxyimino-acetic acid ethyl ester
Pbf: 2,2,4,6,7-pentamethyldihydrobenzofuran-5-sulfonyl
PBS: Phosphate Buffered Saline
PD: Pharmacodynamic
Pen/Strep: Pencillin/Streptomycin
PK: Pharmacokinetic
RP: Reverse Phase
RP-HPLC: Reverse Phase High Performance Liquid Chromatography
RT: Room Temperature
Rt: Retention time
s.c.: Subcutaneously
SD: Standard Deviation
SEC-HPLC: Size Exclusion High Performance Liquic Chromatography
SEM: Standard Error of Mean
SPA: Scintillation Proximity Assay
SPPS: Solid Phase Peptide Synthesis
tBu: tert. butyl
TFA: trifluoroacetic acid
TIS: triisopropylsilane
TLC: Thin Layer Chromatography
Tos: tosylate (or pare-toluenesulfonyl)
Tris: tris(hydroxymethyl)aminomethane or 2-amino-2-hydroxymethyl-propane-1,3-diol
Trt: triphenylmethyl (trityl)
Trx: tranexamic acid (trans-4-(aminomethyl)cyclohexanecarboxylic acid)
UPLC: Ultra Performance Liquid Chromatography
v/v: Volume/volume
w/v: Weight/volume
Materials and Methods
Icosanedioic acid mono-tert-butyl ester
Fmoc-8-amino-3,6-dioxaoctanoic acid
17-(9-Fluorenylmethyloxycarbonyl-amino)-9-aza-3,6,12,15-tetraoxa-10-on-heptadecanoic acid
1-(9-Fluorenylmethyloxycarbonyl)amino-3,6,9,12,15,18-hexaoxahenicosan-21-oic acid
1-(9-Fluorenylmethyloxycarbonyl)amino-3,6,9,12,15,18,21,24,27,30,33,36-dodecaoxanonatriacontan-39-oic acid
alpha-Fmoc-amino-20(ethylene glycol)-omega-carboxylic acid
Fmoc-tranexamic acid
Boc-Lys(Fmoc)-OH
Fmoc-Lys(Fmoc)-OH
Fmoc-Glu-OtBu
Fmoc-Lys(Mtt)-Wangresin Chemical Methods This section is divided in two: Section A relating to general methods (of preparation (A1); and of detection and characterisation (A2)), and section B, in which the preparation and characterisation of a number of specific example compounds and comparative compounds is described.

A. General Methods

A1. Methods of Preparation

This section relates to methods for solid phase peptide synthesis (SPPS methods, including methods for de-protection of amino acids, methods for cleaving the peptide from the resin, and for its purification), as well as methods for detecting and characterising the resulting peptide (LCMS, MALDI, and UPLC methods). The solid phase synthesis of peptides may in some cases be improved by the use of di-peptides protected on the di-peptide amide bond with a group that can be cleaved under acidic conditions such as, but not limited to, 2-Fmoc-oxy-4-methoxybenzyl, or 2,4,6-trimethoxybenzyl. In cases where a serine or a threonine is present in the peptide, pseudoproline di-peptides may be used (available from, e.g., Novabiochem, see also W. R. Sampson (1999), J. Pep. Sci. 5, 403). The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g. Anaspec, Bachem, Iris Biotech, or Novabiochem. Where nothing else is specified the natural L-form of the amino acids are used. The N-terminal amino acid was Boc protected at the alpha amino group (e.g. Boc-His(Boc)-OH, or Boc-His(Trt)-OH for peptides with His at the N-terminus). In case of modular side chain attachment using SPPS the following suitably protected building blocks such as but not limited to Fmoc-8-amino-3,6-dioxaoctanoic acid, Fmoc-tranexamic acid, Fmoc-Glu-OtBu, octadecanedioic acid mono-tert-butyl ester, nonadecanedioic acid mono-tert-butyl ester, tetradecanedioic acid mono-tert-butyl ester, or 4-(9-carboxynonyloxy) benzoic acid tert-butyl ester were used. All operations stated below were performed at 250-µmol synthesis scale.

1. Synthesis of Resin Bound Protected Peptide Backbone

Method: SPPS_P

SPPS_P was performed on a Prelude Solid Phase Peptide Synthesiser from Protein Technologies (Tucson, Ariz. 85714 U.S.A.) at 250-µmol scale using six fold excess of Fmoc-amino acids (300 mM in NMP with 300 mM HOAt or Oxyma Pure®) relative to resin loading, e.g. low load Fmoc-Gly-Wang (0.35 mmol/g). Fmoc-deprotection was performed using 20% (v/v) piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min).

Method: SPPS_L

SPPS_L was performed on a microwave-based Liberty peptide synthesiser from CEM Corp. (Matthews, N.C. 28106, U.S.A.) at 250-µmol or 100-µmol scale using six fold excess of Fmoc-amino acids (300 mM in NMP with 300 mM HOAt or Oxyma Pure®) relative to resin loading, e.g. low load Fmoc-Lys(Mtt)-Wang (0.35 mmol/g). Fmoc-deprotection was performed using 5% (v/v) piperidine in NMP at up to 75° C. for 30 seconds where after the resin was drained and washed with NMP and the Fmoc-deprotection was repeated this time for 2 minutes at 75° C. Coupling was performed using 1:1:1 amino acid/(HOAt or Oxyma Pure®)/DIC in NMP. Coupling times and temperatures were generally 5 minutes at up to 75° C. Longer coupling times were used for larger scale reactions, for example 10 min. Histidine amino acids were double coupled at 50° C., or quadruple coupled if the previous amino acid was sterically hindered (e.g. Aib). Arginine amino acids were coupled at RT for 25 minutes and then heated to 75° C. for 5 min. Some amino acids such as but not limited to Aib, were "double coupled", meaning that after the first coupling (e.g. 5 min at 75° C.), the resin is drained and more reagents are added (amino acid, (HOAt or Oxyma Pure®) and DIC), and the mixture is heated again (e.g. 5 min at 75° C.). NMP washes (5×10 ml) were performed between deprotection and coupling steps.

Method: SPPS_S

SPPS_S was performed on a Symphony Solid Phase Peptide Synthesiser from Protein Technologies (Tucson, Ariz. 85714 U.S.A.) at 250-µmol scale using 9 fold excess of Fmoc-amino acids relative to resin loading. Resin loading was typically in the range 0.25 mmol/g-0.4 mmol/g. Fmoc-deprotection was performed using 20% (v/v) piperidine in NMP. Coupling was performed using 3:3:3:4 amino acid/(HOAt or Oxyma Pure®)/DIC/collidine in NMP. NMP and DCM top washes (7 ml, 0.5 min, 2×2 each) were performed between deprotection and coupling steps. Coupling times were generally 60 minutes. Some amino acids including, but not limited to Fmoc-Arg(Pbf)-OH, Fmoc-Aib-OH or Boc-His(Trt)-OH were "double coupled", meaning that after the first coupling (e.g. 60 min), the resin is drained and more reagents are added (amino acid, (HOAt or Oxyma Pure®), DIC, and collidine), and the mixture allowed to react again (e.g. 60 min).

2. Synthesis of Side Chains

Mono Esters of Diacids

Overnight reflux of the C8, C10, C12, C14, C16 and C18 diacids with Boc-anhydride DMAP t-butanol in toluene gives predominately the t-butyl mono ester. Obtained is after work-up a mixture of mono acid, diacid and diester. Purification is carried out by washing, short plug silica filtration and crystallisation. Icosanedioic acid mono-tert-butyl ester can be prepared as known in the art. For a method please refer to WO 2010102886 A1.

3. Attachment of Side Chains to Resin Bound Protected Peptide Backbone

When an acylation is present on a lysine side chain, the epsilon amino group of lysine to be acylated was protected with either Mtt, Mmt, Dde, ivDde, or Boc, depending on the route for attachment of the protracting moiety and linker. Dde- or ivDde-deprotection was performed with 2% (v/v) hydrazine in NMP (2×20 ml, each 10 min) followed by NMP washings (4×20 ml). Mtt- or Mmt-deprotection was performed with 2% TFA (v/v) and 2-3% TIS (v/v) in DCM (5×20 ml, each 10 min) followed by DCM (2×20 ml), 10% (v/v) MeOH and 5% (v/v) DIPEA in DCM (2×20 ml) and NMP (4×20 ml) washings, or by treatment with hexafluoroisopropanol/DCM (75:25, 5×20 ml, each 10 min) followed by washings as above. In some cases the Mtt group was removed by automated steps on the Liberty peptide synthesiser. Mtt deprotection was performed with hexafluoroisopropanol or hexafluoroisopropanol/DCM (75:25) at room temperature for 30 min followed by washing with DCM (7 ml×5), followed by NMP washings (7 ml×5). The side chain elements can be attached to the peptide either by acylation of the resin bound peptide or by acylation in solution of the unprotected peptide. In case of attachment of the side chain elements to the protected peptidyl resin the attachment can be modular using SPPS and suitably protected building blocks.

Method: SC_P

If N-ε-lysine protection group was Mtt, the Mtt group was removed with neat HFIP (3×15 min) followed by washings with DCM and the acylation performed on a Prelude peptide synthesiser (10 eq. Fmoc-AA, 10 eq. DIC and 10 eq. Oxyma Pure®, 10 eq. collidine 30 min and 25% (v/v) piperidine in NMP to remove the Fmoc-group). Fmoc-Glu-OtBu was double coupled for 4 hours. The terminal residue was attached using similar conditions.

Method: SC_L

The N-ε-lysine protection group was removed as described above and the chemical modification of the lysine was performed by one or more automated steps on the Liberty peptide synthesiser using suitably protected building blocks as described above. Double couplings were performed as described in SPPS_P.

Method: SC_S

The N-ε-lysine protection group was removed as described above and the chemical modification of the lysine was performed by one or more automated steps on the Symphony peptide synthesiser using suitably protected building blocks as described above. Double couplings were performed as described in SPPS_P.

Method: SC_M1

The N-ε-lysine protection group was removed as described above. The side chain element was dissolved in NMP/DCM (1:1.10 ml). The activating reagent such as HOBt or Oxyma Pure® (4 molar equivalents relative to resin) and DIC (4 molar equivalents relative to resin) was added and the solution was stirred for 15 min. The solution was added to the resin and DIPEA (4 molar equivalents relative to resin) was added. The resin was shaken 2 to 24 hours at room temperature. The resin was washed with NMP (2×20 ml), NMP/DCM (1:1.2×20 ml) 20 and DCM (2×20 ml).

Method: SC_M2

The N-ε-lysine protection group was removed as described above. The sidechain acylation was performed on a Prelude peptide synthesiser (10 eq. Fmoc-AA, 10 eq. DIC and 10 eq. Oxyma Pure®, 10 eq. collidine 30 min and 25% (v/v) piperidine in NMP to remove the Fmoc-group). Fmoc-Glu-OtBu was double coupled for 4 hours. The peptide backbone was transferred to a shaker. The side chain element was dissolved in NMP/DCM (1:1.10 ml). The activating reagent such as HOBt or Oxyma Pure® (4 molar equivalents relative to resin) and DIC (4 molar equivalents relative to resin) was added and the solution was stirred for 15 min. The solution was added to the resin and DIPEA (4 molar equivalents relative to resin) was added. The resin was shaken 2 to 24 hours at room temperature. The resin was washed with NMP (2×20 ml), NMP/DCM (1:1, 2×20 ml) 20 and DCM (2×20 ml).

4. Cleavage of Resin Bound Peptide with or without Attached Side Chains and Purification Method: CP_M1

After synthesis the resin was washed with DCM, and the peptide was cleaved from the resin by a 2-3 hour treatment with TFA/TIS/water (95/2.5/2.5 or 92.5/5/2.5) followed by precipitation with diethylether. The peptide was dissolved in a suitable solvent (such as, e.g., 30% (v/v) acetic acid) and purified by standard RP-HPLC on a C18, 5 µM column, using acetonitrile/water/TFA. The fractions were analysed by a combination of UPLC, MALDI and LCMS methods, and the appropriate fractions were pooled and lyophilised.

A2. General Methods for Detection and Characterisation

1. LC-MS Methods

Method: LCMS_4

LCMS_4 was performed on a setup consisting of Waters Acquity UPLC system and LCT Premier XE mass spectrometer from Micromass. Eluents: A: 0.1% (v/v) Formic acid in water B: 0.1% (v/v) Formic acid in acetonitrile The analysis was performed at RT by injecting an appropriate volume of the sample (preferably 2-10 µl) onto the column which was eluted with a gradient of A and B. The UPLC conditions, detector settings and mass spectrometer settings were: Column: Waters Acquity UPLC BEH, C-18, 1.7 µm, 2.1 mm×50 mm. Gradient: Linear 5%-95% acetonitrile during 4.0 min (alternatively 8.0 min) at 0.4 ml/min. Detection: 214 nm (analogue output from TUV (Tunable UV detector)) MS ionisation mode: API-ES Scan: 100-2000 amu (alternatively 500-2000 amu), step 0.1 amu.

2. UPLC Methods

Method: B4_1

The RP-analysis was performed using a Waters UPLC system fitted with a dual band detector. UV detections at 214 nm and 254 nm were collected using an ACQUITY UPLC BEH130. C18, 130 Å, 1.7 um, 2.1 mm×150 mm column, 40° C. The UPLC system was connected to two eluent reservoirs containing: A: 99.95% (v/v) $H_2O$, 0.05% (v/v) TFA; B: 99.95% $CH_3CN$, 0.05% TFA. The following linear gradient was used: 95% A, 5% B to 5% A, 95% B over 16 minutes at a flow-rate of 0.40 ml/min.

B. Synthesis of Compounds of the Invention

Example 1

N{Epsilon-36}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]eth oxy]acetyl],N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]eth oxy]acetyl]-[Trp8,Glu22,Arg26,Arg34,Lys36,Lys37]-GLP-1-(7-37)-peptide Chem. 21

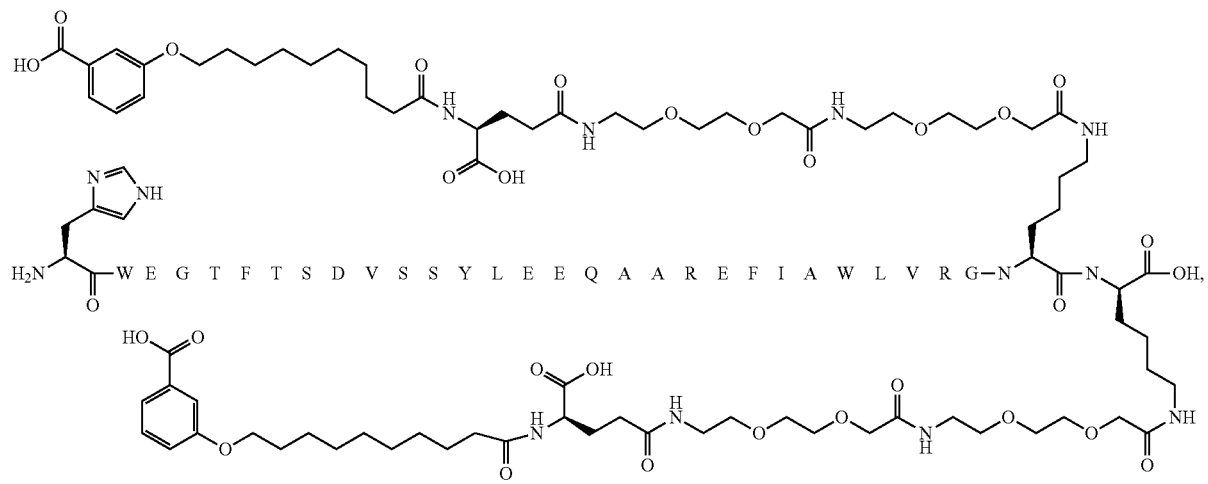

This compound is a derivative of the GLP-1 analogue of SEQ ID NO: 5.

Preparation Method: SPPS_P; SC_M2; CP_M1
LCMS_4: Rt=2.1 min m/z: m/5=1013, m/4=1266, m/3=1688
UPLC_B4_1: Rt=8.5 min

Example 2

N{Epsilon-26}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Trp8,Arg34]-GLP-1-(7-37)-peptide Chem. 22

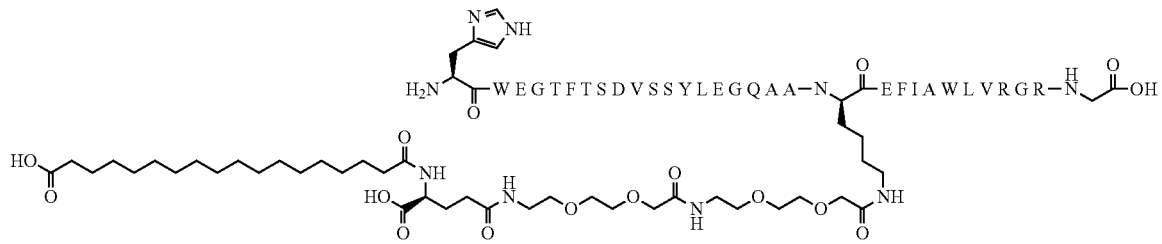

This compound is a derivative of the GLP-1 analogue of SEQ ID NO: 7.
Preparation Method: SPPS_P; SC_P; CP_M1
LCMS_4: Rt=2.2 min m/z: m/5=843, m/4=1054, m/3=1405
UPLC_B4_1: Rt=9.4 min

Example 3

N{Epsilon-27}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]eth oxy]acetyl],N{Epsilon-36}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]eth oxy]acetyl]-[Trp8,Glu22,Arg26,Lys27,Glu30,Arg34,Lys36]-GLP-1-(7-37)-peptidyl-Glu-Gly Chem. 23

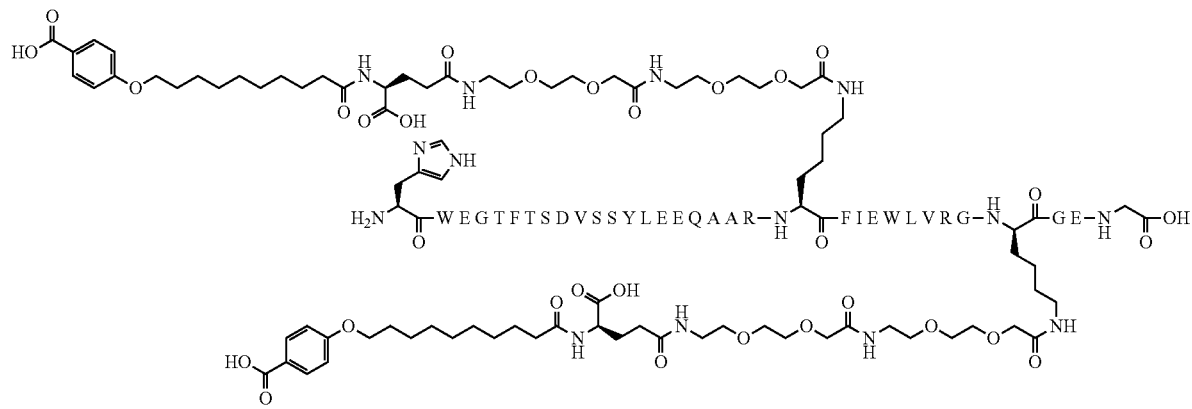

This compound is a derivative of the GLP-1 analogue of SEQ ID NO: 9.
Preparation Method: SPPS_L; SC_L; CP_M1
LCMS_4: Rt=2.1 min m/z: m/4=1310, m/3=1746
UPLC_B4_1: Rt=8.2 min

Example 4

N{Epsilon-26}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]eth oxy]acetyl],N{Epsilon-37}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]eth oxy]acetyl]-[Trp8,Arg34,Lys- 37]-GLP-1-(7-37)-peptide

[Chem. 24]
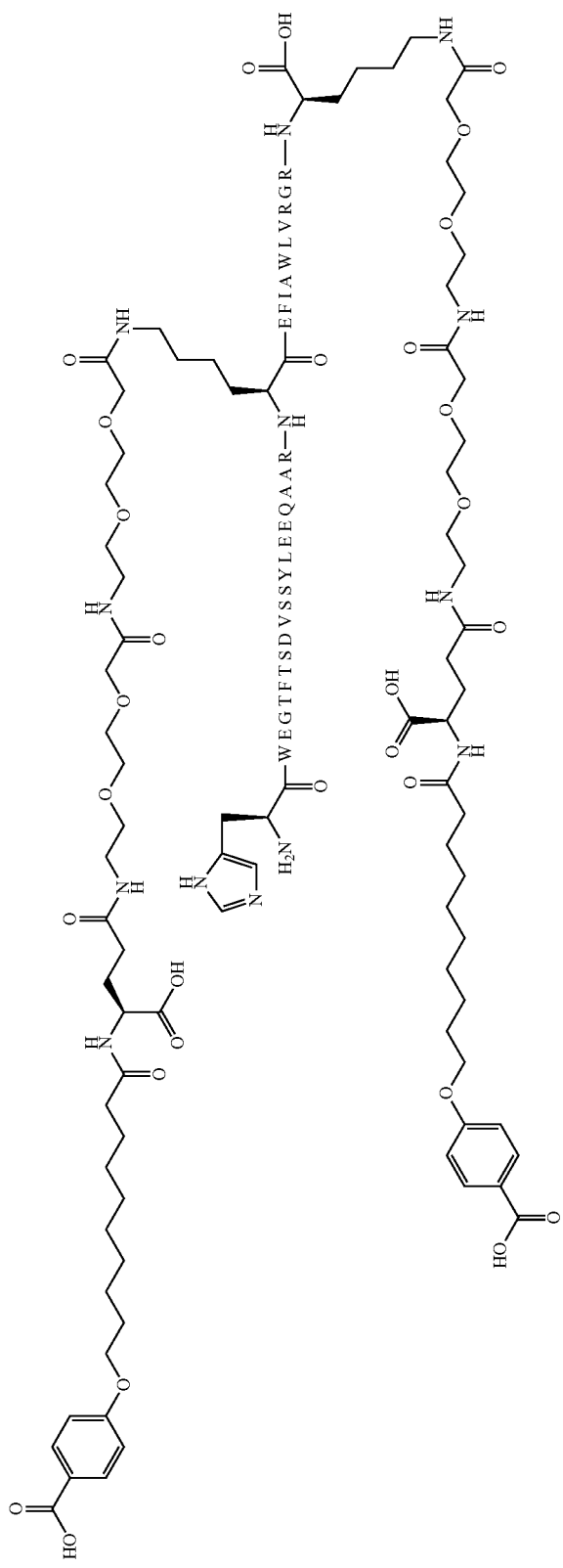

This compound is a derivative of the GLP-1 analogue of SEQ ID NO: 11.
Preparation Method: SPPS_S; SC_S; CP_M1
LCMS_4: Rt=2.2 min m/z: m/5=998, m/4=1248, m/3=1663
UPLC_B4_1: Rt=8.2 min

Example 5

N{Epsilon-26}-[(4S)-4-carboxy-4-(hexadecanoylamino)butanoyl]-[Trp8,Arg34]-GLP-1-(7-37)-peptide

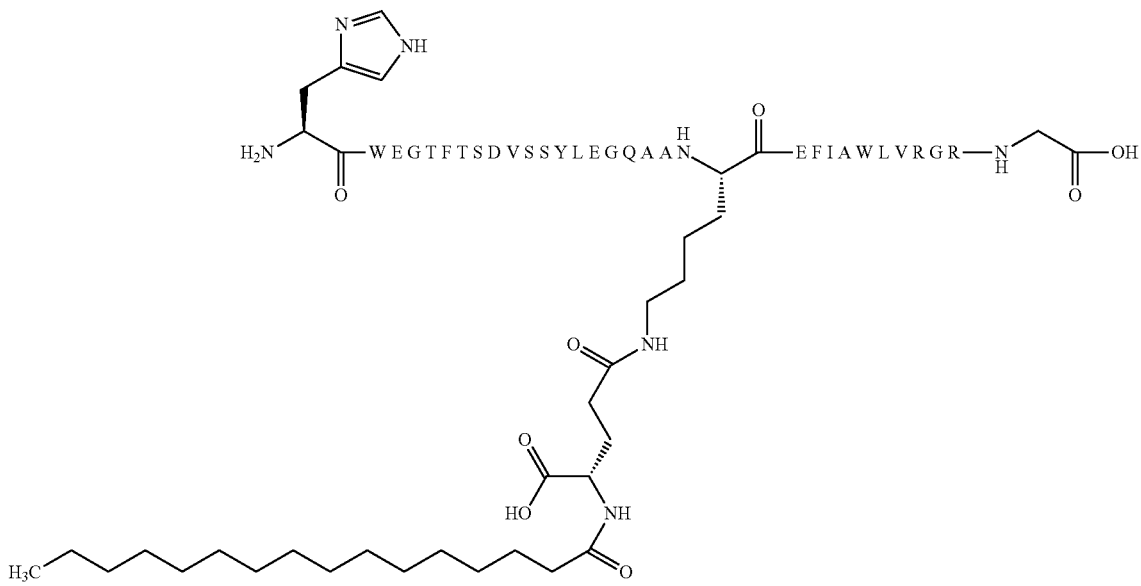

Chem. 25

This compound is a derivative of the GLP-1 analogue of SEQ ID NO: 7.
Preparation Method: SPPS_S; SC_S; CP_M1
LCMS_4: Rt=2.6 min m/z: m/5=774, m/4=967, m/3=1289
UPLC_B4_1: Rt=9.9 min

Example 6

8W dulaglutide was prepared as described in Example 6A below.

Example 7

N{Epsilon-36}-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl],N{Epsilon-37}-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]-[Trp8,Glu22,Arg26,Arg34,Lys36,Lys37]-GLP-1-(7-37)-peptide Chem. 26
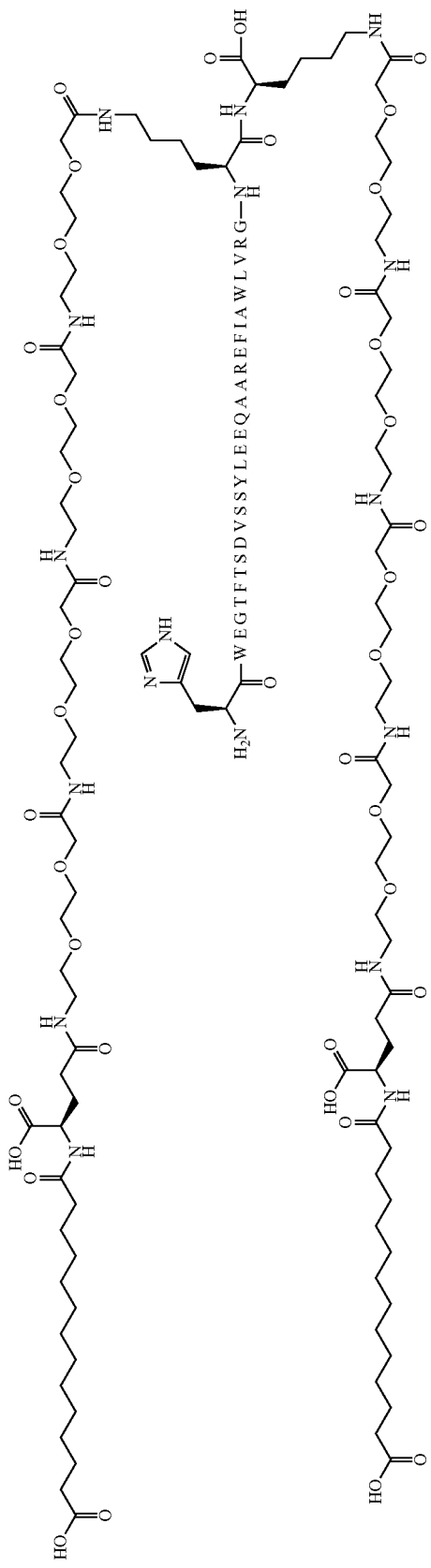

This compound is a derivative of the GLP-1 analogue of SEQ ID NO: 5.

Preparation Method: SPPS_P; SC_P; CP_M1

LCMS_4: Rt=2.1 min m/z: m/5=1109, m/4=1386, m/3=1848

UPLC_B4_1: Rt=9.0 min

Example 8

N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Trp8,Glu22,Arg26,Arg34,Lys36,Lys37]-GLP-1-(7-37)-peptide Chem. 27

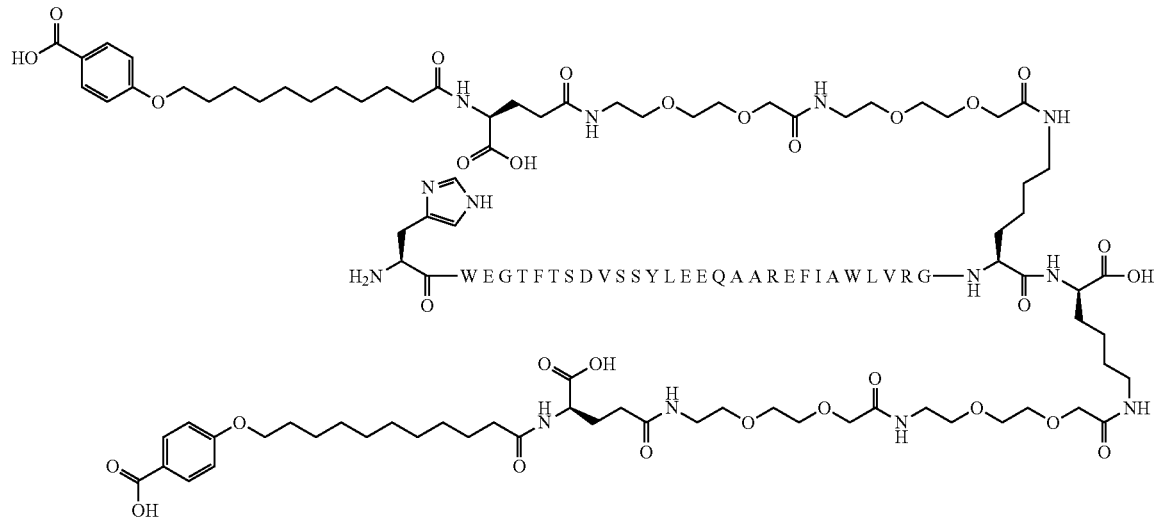

This compound is a derivative of the GLP-1 analogue of SEQ ID NO: 5.
Preparation Method: SPPS_P; SC_P; CP_M1
LCMS_4: Rt=2.2 min m/z: m/5=1019, m/4=1273
UPLC_B4_1: Rt=8.6 min

Example 9

N{Alpha}([Trp8,Glu22,Arg26,Arg34]-GLP-1-(7-37)-peptidyl)-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys-Gly-Gly-Ser-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys Chem. 28

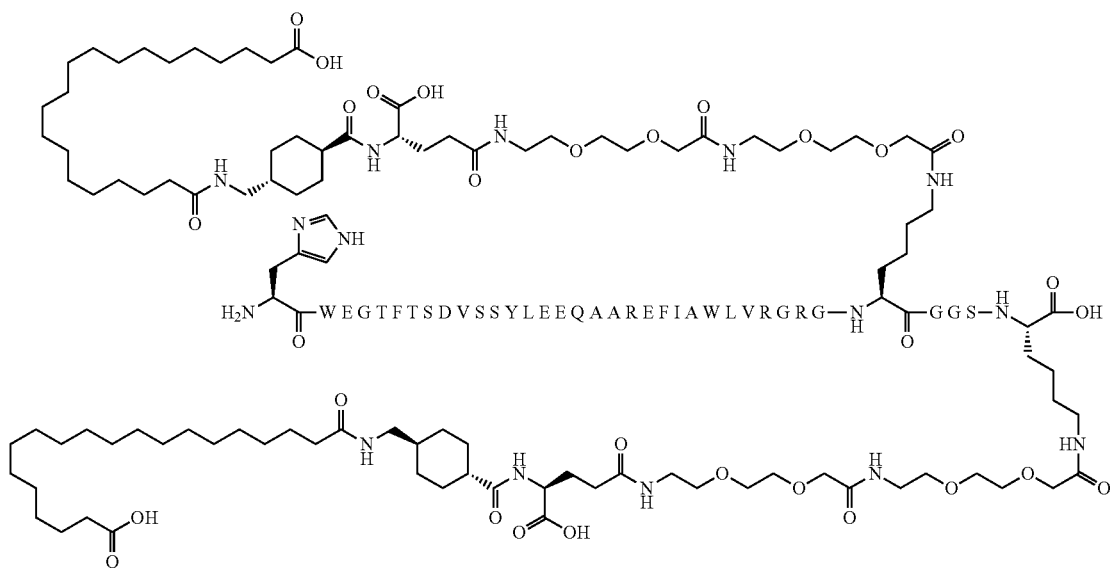

This compound is a derivative of the GLP-1 analogue of SEQ ID NO: 16.
Preparation Method: SPPS_P; SC_P; CP_M1
LCMS_4: Rt=2.9 min m/z: m/5=1165, m/4=1456, m/3=1940
UPLC_B4_1: Rt=11.3 min

Example 10

N{Epsilon-37}-[(2S)-2,6-bis[[2-[2-[2-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]eth oxy]acetyl]amino]hexanoyl]-[Trp8,Glu22,Arg26,Arg34,Lys37]-GLP-1-(7-37)-peptide

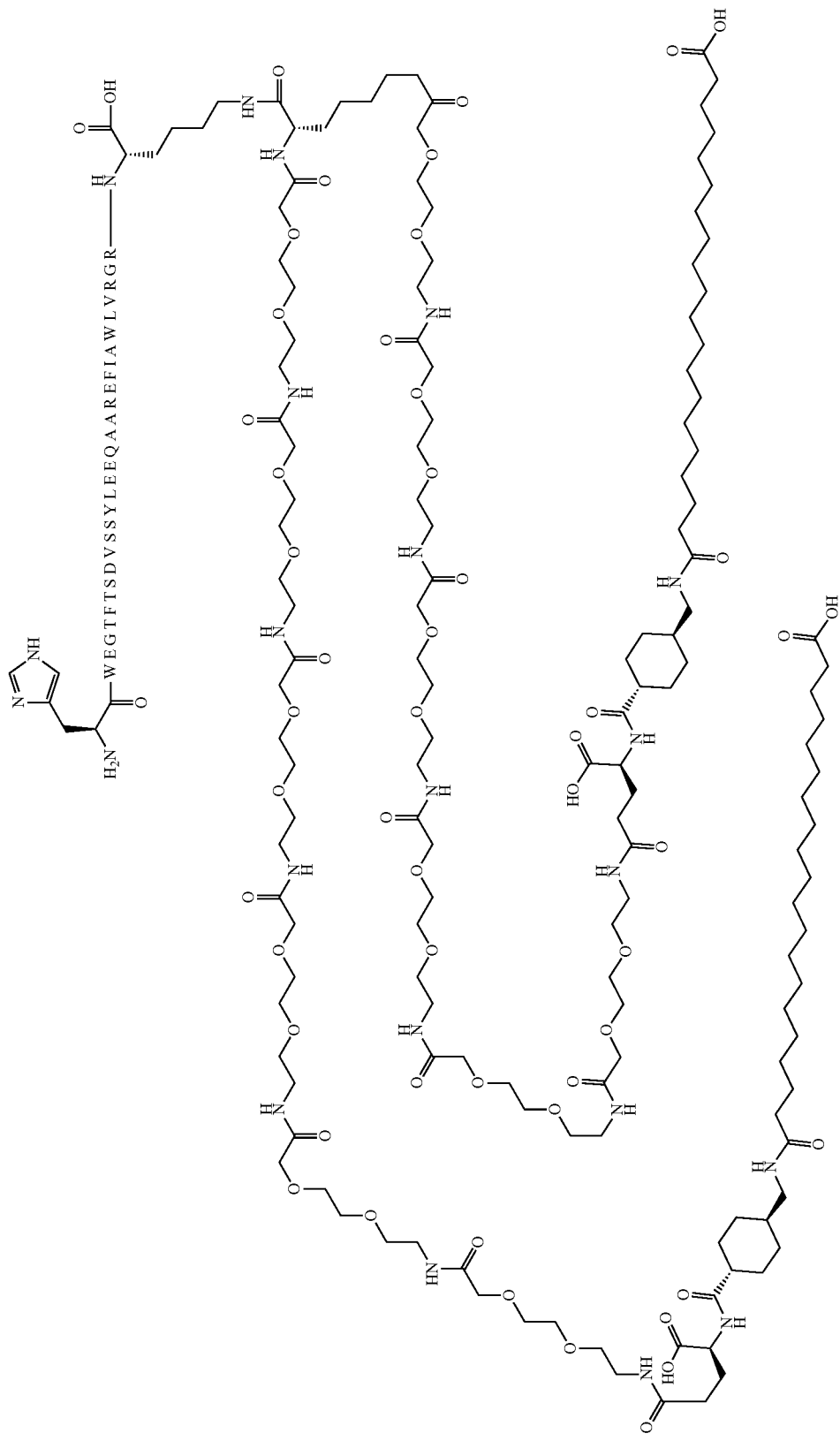

This compound is a derivative of the GLP-1 analogue of SEQ ID NO: 18.
Preparation Method: SPPS_P; SC_P; CP_M1
LCMS_4: Rt=2.9 min m/z: m/5S=1345, m/4=1681, m/3=2241
UPLC_B4_1:Rt=11.0 min

Example 11

N{Alpha}([Trp8,Glu22,Arg26,Arg34,Pro37]-GLP-1-(7-37)-peptidyl)-N{Epsilon}[2-[bis[3-[[2-[2-[2-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]Lys Chem. 30

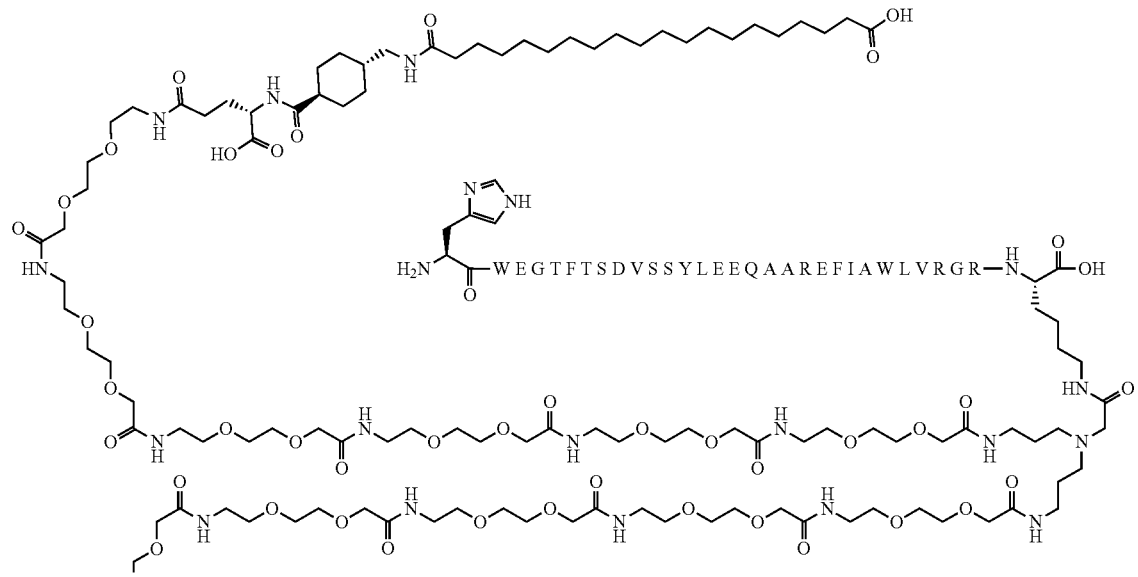

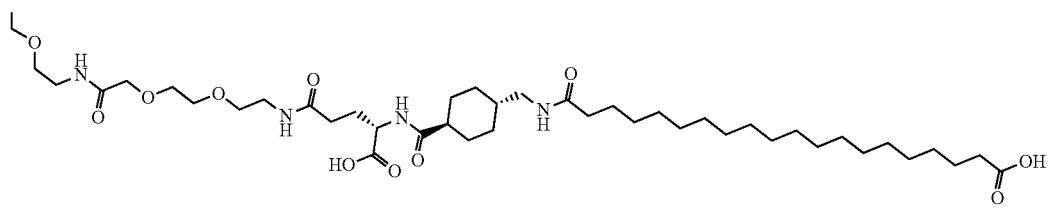

This compound is a derivative of the GLP-1 analogue of SEQ ID NO: 20.

Preparation Method: SPPS_P; SC_P; CP_M1

LCMS_4: Rt=2.8 min m/z: m/5=1373, m/4=1716, m/3=2288

UPLC_B4_1: Rt=10.7 min

Example 12

N{Epsilon-37}-[2-[2-[2-[[2-[2-[2-[[(2S)-2,6-bis[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]amino]ethoxy]ethoxy]acetyl]amino]ethoxy]ethoxy]acetyl]-[Trp8,Glu22,Arg26,Arg34,Lys37]-GLP-1-(7-37)-peptide

[Chem. 31]
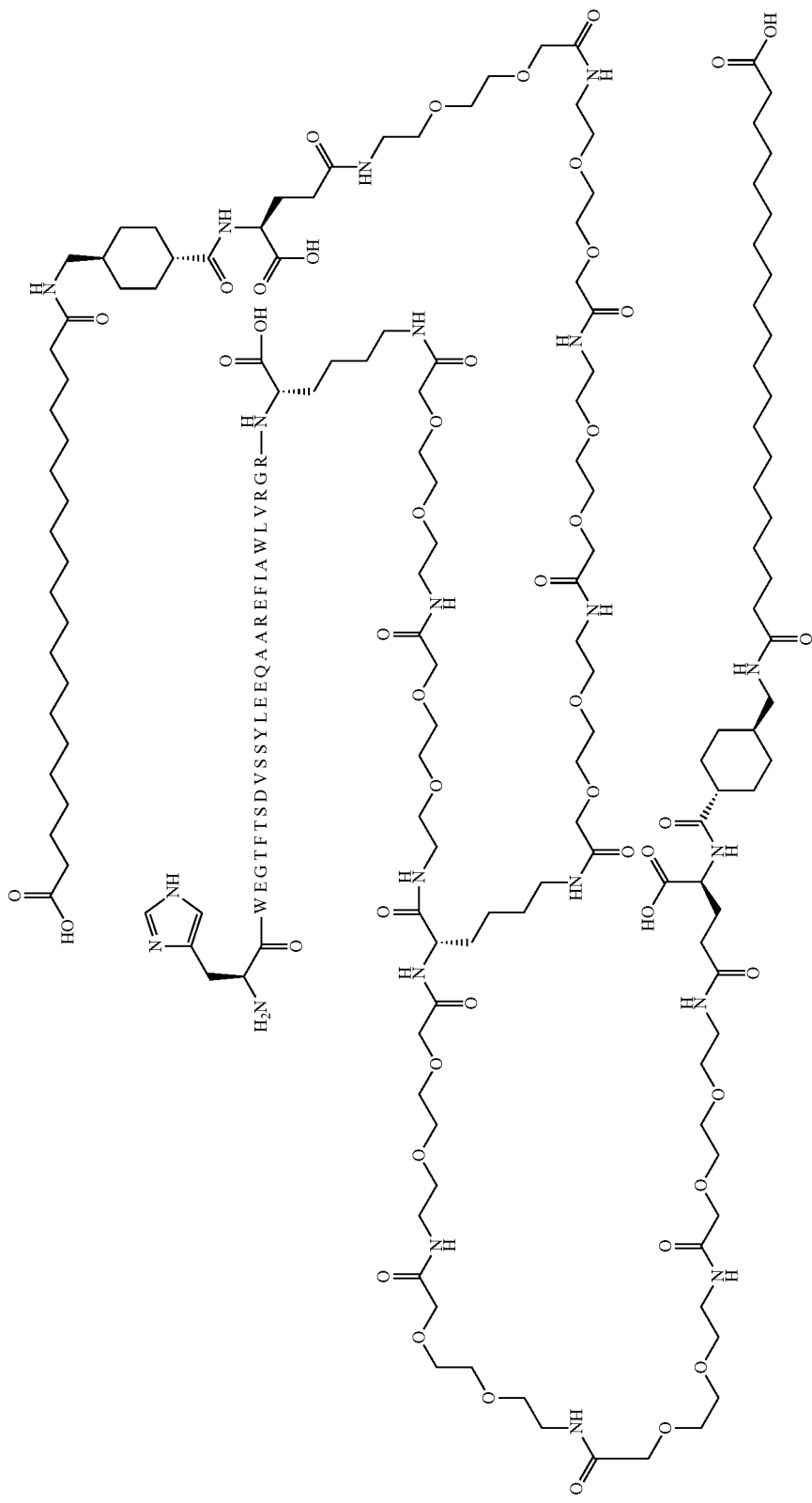

This compound is a derivative of the GLP-1 analogue of SEQ ID NO: 18.
Preparation Method: SPPS_P; SC_P; CP_M1
LCMS_4: Rt=3.3 min m/z: m/5=1287, m/4=1609, m/3=2145
UPLC_B41: Rt=11.0 min

Example 13

N{Epsilon-37}-[2-[2-[2-[[2-[2-[2-[[2-[bis[3-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]amino]ethoxy]ethoxy]acetyl]amino]ethoxy]ethoxy]acetyl]-[Trp8,Glu22,Arg26,Arg34,Lys37]-GLP-1-(7-37)-peptide

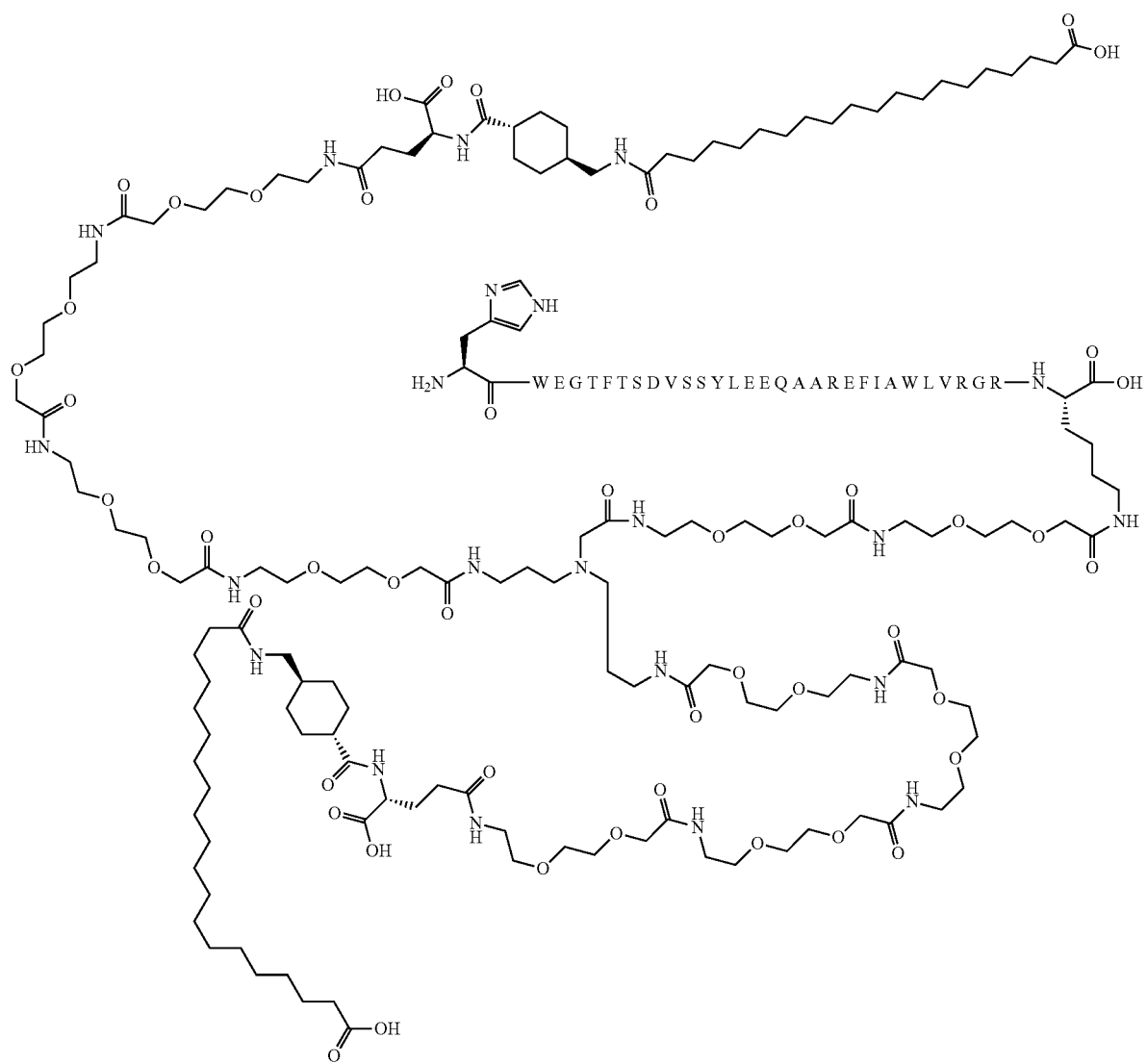

Chem. 32

This compound is a derivative of the GLP-1 analogue of SEQ ID NO: 18.
Preparation Method: SPPS_P; SC_P; CP_M1
LCMS_4: Rt=2.9 min m/z: m/5=1296, m/4=1619, m/3=2159
UPLC_B4_1: Rt=11.0 min

Comparative Example A

This compound is native GLP-1 (GLP-1(7-37)-peptide), of SEQ ID NO: 1. The compound may be prepared as is known in the art.

Comparative Example B

[Pro8,Glu22,Arg26]-GLP-1-(7-37)-peptide

This compound is the GLP-1 analogue of SEQ ID NO: 2.
Preparation Method: SPPS_P; CP_M1
LCMS_4: Rt=1.8 min m/z: m/4=871, m/3=1161, m/2=1742

Comparative Example C

[Gly8]-GLP-1-(7-37)-Peptide

This compound is the GLP-1 analogue of SEQ ID NO: 3.
Preparation Method: SPPS_S; CP_M1
LCMS_4: Rt=1.7 min m/z: m/4=836, m/3=1115

Comparative Example D

[Trp8]-GLP-1-(7-37)-Peptide

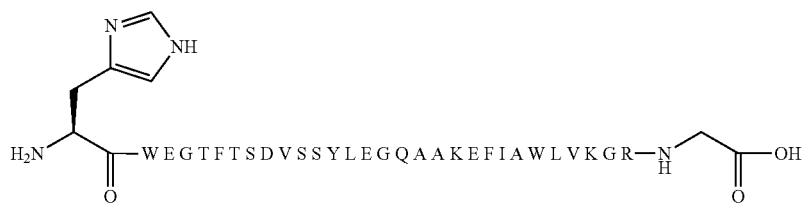

This compound is the GLP-1 analogue of SEQ ID NO: 4.
Preparation Method: SPPS_P; CP_M1
LCMS_4: m/z: m/4=869, m/3=1158, m/2=1737

Comparative Example 1A

This compound is Example 15 of WO 2015/155151.
It differs from the compound of Example 1 only in having Aib8 instead of Trp8.

Comparative Example 2A

This compound is Example 4 of WO 2006/097537, viz. N{Epsilon-26}-[2-(2-[2-(2-[2-(2-[4-(17-Carboxyheptadecanoylamino)-4(S)-carboxybutyrylamino]ethoxy)ethoxy]acetylamino)ethoxy]ethoxy)acetyl][Aib8,Arg34]GLP-1-(7-37)peptide. It differs from the compound of Example 2 only in having Aib8 instead of Trp8.

Comparative Example 3A

This compound is Example 31 of WO 2012/140117.
It differs from the compound of Example 3 only in having Aib8 instead of Trp8.

Comparative Example 4A

This compound is Example 2 of WO 2011/080103.
It differs from the compound of Example 4 only in having Aib8 instead of Trp8.

Comparative Example 5A

This compound is Example 37 of WO 98/08871.
It differs from the compound of Example 5 only in having Aib8 instead of Trp8.

Comparative Example 6A—Dulaglutide and 8W dulaglutide

Dulaglutide is an Fc fusion protein of a GLP-1 analogue. Its preparation and characterisation is described in Diabetes/Metabolism Research and Reviews, 2010, vol. 26, p. 287-296 by Glaesner et al (incorporated herein by reference). The GLP-1-Fc fusion protein of Glaesner which acquired the INN name dulaglutide is called LY2189265. The amino acid sequence of the GLP-1 analogue peptide part including the linker (4×G-S-4×G-S-4×G-S-A) is HGEGTFTSDVSSYLEEQAAKEFIAWLVKGGGGGGSGGGGSGGGG-SA, see legend to FIG. 1 on p. 291 of Glaesner et al. This corresponds to the sequence of amino acids 17-63 and 308-354 of SEQ ID NO: 14 of the present sequence listing. The IgG-Fc fusion partner is described on p. 290 of Glaesner et al, in the right-hand column, 1st paragraph of the section headed "The GLP-1-Fc fusion protein LY2189265 has preserved in vitro activity and an extended in vivo half-life". This corresponds to the remaining non-signal-peptide-parts of SEQ ID NO: 14 of the present sequence listing (i.e., amino acids 64-291 and 355-582). According to Glaesner et al the following substitutions were made in the IgG-Fc part: S228P, F234A, L234A (using the Kabat numbering which is standard for antibodies, which corresponds to amino acids 73, 79, and 80, respectively, in SEQ ID NO: 14).

The expression "8W dulaglutide" refers to an analogue of dulaglutide in which the Gly residue at the position corresponding to position 8 in native GLP-1 (SEQ ID NO: 1) is substituted by a Trp (see below sequence, part of SEQ ID NO: 15, emphasis added).

The mature peptide parts of the amino acid sequences of the dulaglutide monomer and the 8W dulaglutide monomer are as follows:

HGEGTFTSDVSSYLEEQAAKEFIAWLVKGGGGG-GGSGGGGSGGGGSAESKYGPPCPPCPAPEAAGGPS-VFLFPPKPKDTLMISRTPEVTCVVVDVSQEDPEVQF-NWYVDGVEVHNAKTKPREEQFNSTYRVVSVLTVL-H QDWLNGKEYKCKVSNKGLPSSIEKTISKAKGQPR-EPQVYTLPPSQEEMTKNQVSLTCLVKGFYPSDIAVE-W ESNGQPENNYKTTPPVLDSDGSFFLYSRLTV- DKS-RWQEGNVFSCSVMHE ALHNHYTQKSLSLSLG (mature monomeric part of SEQ ID NO: 14, i.e. amino acids 17-291 or 308-582 of SEQ ID NO: 14), and HWEGTFTSDVSSYLEEQAAKEFIAWLVKGGGGG-GGSGGGGSGGGGSAESKYGPPCPPC PAPEAAGGPS-VFLFPPKPKDTLMISRTPEVTCVVVDVSQEDPEVQF-NWYVDGVEVHNAKTKPREEQFNSTYRVVSVLTVL-H QDWLNGKEYKCKVSNKGLPSSIEKTISKAKGQPR-EPQVYTLPPSQEEMTKNQV SLTCLVKGFYPSDIAVE-WESNGQPENNYKTTPPVLDSDGSFFLYSRLTVDKS-RWQEGNVFSCSVMH EALHNHYTQKSLSLSLG (monomeric part of SEQ ID NO: 15, i.e. amino acids 1-275 or 276-550 thereof), respectively.

In solution two such molecules form a dimer with intra chain Cys-Cys bonds between the Cys residues at position 55 and 58 (i.e. between Cys71 and Cys362, and Cys74 and Cys365 of SEQ ID NO: 14, which includes twice the 16 amino acids signal peptide part).

Cloning of Dulaglutide and 8W Dulaglutide Constructs in a pSV5 Based Vector

A vector construct was made containing a chemically synthesised DNA fragment encoding CD33-dulaglutide (where CD33 is the signal peptide from the human CD33 antigen, Gp67). The mature part of the amino acid sequence (of dulaglutide) encoded by the DNA fragment is given in SEQ ID NO: 14 (amino acids 17-291 and 308-582). Mutagenesis was performed on the construct in order to introduce the 8W mutation in the CD33-dulaglutide gene. The mature part of the amino acid sequence encoded by the resulting DNA fragment is given in SEQ ID NO: 15 (amino acids 1-275 and 276-550 of SEQ ID NO: 15, viz. also a dimer). In SEQ ID NO: 15 each of the fragments amino acids 1-47 and 276-322 constitutes the GLP-1 peptide with linker, whereas amino acids 48-275 and 323-550 of SEQ ID NO: 15 is the IgG-Fc part, in which there are Cys-Cys bonds between Cys55 and Cys330 as well as between Cys58 and Cys333.

The DNA fragments encoding CD33-dulaglutide and CD33-8W dulaglutide were amplified by PCR, and cloned in an expression vector for transient expression. The expression of the CD33-dulaglutide and CD33-8W dulaglutide genes were under the control of a CMV promoter in the resulting transient expression vectors. A rabbit beta-globin polyadenylation signal acted as transcriptional terminator in the transient expression vectors. All the molecular biology steps described above were performed using standard molecular biology techniques.

Expression of Dulaglutide and 8W Dulaglutide in EXPI293F Cells

The two plasmids resulting from the cloning of the dulaglutide and the 8W dulaglutide constructs in the transient expression vector were expressed at 200 mL scale in the Expi293™ Expression System (Thermo Fisher Scientific, Cat no. A14635). The transfections were performed using 1 mg DNA construct/L transfected cells. The transfections were performed following the protocol provided by the supplier of the expression system. The transfected cells were cultured at 36.5° C. in an orbital shaker for five days. The supernatant was harvested by centrifugation. The supernatant was subsequently sterile filtered using a 0.22 μm Pore, PES filter and delivered for purification.

Purification

The cell free supernatants containing dulaglutide or 8W dulaglutide were applied on Protein A columns. The columns were washed with PBS (Phospate buffered saline solution) and the bound protein was eluted with 0.1M Acetic Acid. The eluted fractions were immediately mixed with 0.3 volume 1M Tris-Cl (pH 9.0). The proteins were either purified further on a size exclusion column running in PBS or desalted by running through a desalting column in PBS. The fractions containing dulaglutide or 8W dulaglutide were characterized by SDS-PAGE and mass spectrometry, sterile-filtered (0.22 μm), assessed for concentration (absorption at 280 nm) and stored at −20° C. Experimentally determined masses obtained using mass spectrometry verified the identity of dulaglutide and 8W dulaglutide, respectively.

Comparative Example 7A

This compound is Example 20 of WO 2015/155151.
It differs from the compound of Example 7 only in having Aib8 instead of Trp8.

Comparative Example 8A

This compound is Example 1 of WO 2015/155151.
It differs from the compound of Example 8 only in having Aib8 instead of Trp8.

Comparative Example 9A

This compound is Example 3 of WO 2015/000942.
It differs from the compound of Example 9 only in having Aib8 instead of Trp8.

Comparative Example 10A

This compound is Example 32 of WO 2014/202727.
It differs from the compound of Example 10 only in having Aib8 instead of Trp8.

Comparative Example 11A

This compound is Example 10 of WO 2016/083499.
It differs from the compound of Example 11 only in having Aib8 instead of Trp8.

Comparative Example 12A

This compound is Example 14 of WO 2016/097108.
It differs from the compound of Example 12 only in having Aib8 instead of Trp8.

Comparative Example 13A

This compound is Example 11 of WO 2016/083499.
It differs from the compound of Example 13 only in having Aib8 instead of Trp8.

Pharmacological Methods

Example 14: In Vitro DPP-IV Stability

The purpose of this example is to test the stability of GLP-1 analogues against degradation by dipeptidyl peptidase-4 (DPP-IV), in comparison with native GLP-1. The GLP-1 analogues of Examples A, B, C, and D were tested as described below.

Principle

The peptides are incubated in vitro in buffer with DPP-IV, samples are taken at regular intervals, the DPP-IV enzyme is inactivated to stop further degradation, and the amount of non-degraded peptide in the samples is determined using LC-MS.

Materials and Methods

Buffer A

Buffer A is a HEPES buffer (Gibco by Life Science, NY, USA) to which 0.005% (v/v) Tween20® Sigma-Aldrich, USA) and 0.001% (w/v) BSA (Sigma-Aldrich, USA) has been added and pH was adjusted to 7.4.

LC-MS Method

LC-MS was performed on a setup consisting of Waters Acquity UPLC system and Maxis 4G from Bruker Daltonics. The mobile phases consisted of: A: 0.1% (v/v) Formic acid in water B: 0.1% (v/v) Formic acid in acetonitrile. The HPLC analysis was performed at 60° C. by injecting 10 μl of sample onto the column, which was eluted with a gradient of A and B. The UPLC conditions, detector settings and mass spectrometer settings were: Column: Waters Acquity UPLC BEH, C-4, 1.7 μm, 2.1 mm×50 mm). Gradient: Linear 5%-70% mobile phase B during 8 min at 0.3 ml/min. MS was conducted in positive ionisation mode by electrospray ionisation from m/z ionisation mode and scan from m/z 300-1800.

Internal Standard

Liraglutide (compound of Example 5A) was used as internal standard.

Procedure

10 μM of the respective peptide was incubated with DPP-IV (Recombinant Dipeptidyl Peptidase, R & D systems, 2 μg/ml) at 37° C. in Buffer A. Sample aliqouts were taken at 3, 8, 15, 30, 60, 120 and 180 min. The reactions were terminated by addition of 6 volumes of ethanol containing 1% (v/v) TFA (Biosolve BV, The Netherlands) and internal standard. The samples were analysed by LC-MS for the respective non-degraded peptide. Data was plotted according to $1^{st}$ order kinetics (by GraphPad Prism) and the half-lives ($T_{1/2}$) were calculated by the software and reported in minutes.

Results

The resulting half-lives are shown in Table 1 below, relative to the half-live of the Example A compound (native GLP-1).

TABLE 1

| DPP-IV stability in vitro-half-life | |
|---|---|
| Example no. | Half-life (min) |
| A | 1 |
| B | 1 |
| C | 5 |
| D | >20 |

The in vitro DPP-IV stability of the Example B GLP-1 analogue (i.e., with substitutions 8P, 22E, 26R) is similar to that of native GLP-1 (A). As expected, the stability of the Example C analogue (8G) is better than that of native GLP-1. However, quite unexpectedly, the stability of the Example D analogue (8W) proved much better, in fact no degradation at all was observed.

Example 15: In Vitro Potency

The purpose of this example is to test the activity, or potency, of the GLP-1 compounds of the invention along with selected comparative compounds. The in vitro potency is the measure of human GLP-1 receptor activation in a functional whole cell assay.

The potencies of the GLP-1 derivatives of Examples 1-5 and 7-13, and the compounds of Comparative Examples 1A-13A and A-D were determined as described below.

Principle

In vitro potency was determined by measuring the response of the human GLP-1 receptor in a reporter gene assay. The assay was performed in a stably transfected BHK cell line that expresses the human GLP-1 receptor and contains the DNA for the cAMP response element (CRE) coupled to a promoter and the gene for firefly luciferase (CRE luciferase). When the human GLP-1 receptor is activated it results in the production of cAMP, which in turn results in the luciferase protein being expressed. When assay incubation is completed the luciferase substrate (luciferin) is added and the enzyme converts luciferin to oxyluciferin to produce bioluminescence. The luminescence is measured as the readout for the assay.

Cell Culture and Preparation

The cells used in this assay (clone FCW467-12A/KZ10-1) were BHK cells with BHKTS13 as a parent cell line. The cells were derived from a clone (FCW467-12A) that expresses the human GLP-1 receptor and were established by further transfection with CRE luciferase to obtain the current clone.

The cells were cultured at 5% $CO_2$ in cell culture medium. They were aliquoted and stored in liquid nitrogen. Before each assay an aliquot was taken up and washed twice in PBS before being suspended at the desired concentration in the assay specific buffer. For 96-well plates the suspension was made to give a final concentration of $5\times10^3$ cells/well.

Materials

The following chemicals were used in the assay: Pluronic F-68 (10%) (Gibco 2404), ovalbumin (Sigma A5503), DMEM w/o phenol red (Gibco 11880-028), 1 M Hepes (Gibco 15630), Glutamax 100x (Gibco 35050) and steady-lite plus (PerkinElmer 6016757).

Buffers

Cell culture medium consisted of DMEM medium with 10% w/v FBS (Fetal Bovine Serum; Invitrogen 16140-071), 1 mg/ml G418 (Invitrogen 15140-122), 240 nM MTX (methotrexate; Sigma M9929) and 1% w/v pen/strep (penicillin/streptomycin; Invitrogen 15140-122).

Assay medium consisted of DMEM w/o phenol red, 10 mM Hepes and 1× Glutamax. The assay buffer consisted of 2% w/v ovalbumin and 0.2% v/v Pluronic F-68 in assay medium.

Procedure

1) Cell stocks were thawed in a 37° C. water bath.
2) Cells were washed three times in PBS.
3) Cells were counted and adjusted to $5\times10^3$ cells/50 µl ($1\times10^5$ cells/ml) in assay medium. A 50 µl aliquot of cells was transferred to each well in the assay plate.
4) Stocks of the test compounds and reference compounds were diluted to a concentration of 0.2 µM in assay buffer. Compounds were diluted 10-fold to give the following concentrations: $2\times10^{-7}$ M, $2\times10^{-8}$ M; $2\times10^{-9}$ M, $2\times10^{-10}$ M, $2\times10^{-11}$ M, $2\times10^{-12}$ M, $2\times10^{-13}$ M, and $2\times10^{-14}$ M.
5) A 50 µl aliquot of compound or blank was transferred from the dilution plate to the assay plate. Compounds were tested at the following final concentrations: $1\times10^{-7}$ M, $1\times10^{-8}$ M; $1\times10^{-9}$ M, $1\times10^{-10}$ M, $1\times10^{-11}$ M, $1\times10^{-12}$ M, $1\times10^{-13}$ M, and $1\times10^{-14}$ M.
6) The assay plate was incubated for 3 h in a 5% $CO_2$ incubator at 37° C.
7) The assay plate was removed from the incubator and allowed to stand at room temperature for 15 min.
8) A 100 µl aliquot of steadylite plus reagent was added to each well of the assay plate.
9) Each assay plate was covered with aluminum foil to protect it from light and shaken for 30 min at room temperature.
10) Each assay plate was read in a BioTek Synergy 2 Multi-Mode Reader.

Calculations and Results

The data from the BioTek Synergy 2 Multi-Mode Reader were transferred to GraphPad Prism software. The software performs a non-linear regression (log(agonist) vs. response (three parameters)). $EC_{50}$ values, which were calculated by the software and reported in pM, are shown in Table 2 below.

A minimum of three replicates were measured for each sample. The reported $EC_{50}$ values are averages of the measured values for each compound.

TABLE 2

| In vitro potency | |
|---|---|
| Example no. | $EC_{50}$ (pM) |
| 1 | 17 |
| Comparative 1A | 8.1 |
| 2 | 19 |
| Comparative 2A | 3.7 |
| 3 | 2.7 |
| Comparative 3A | 0.53 |
| 4 | 30 |
| Comparative 4A | 6.9 |
| 5 | 21 |
| Comparative 5A | 6.8 |
| Comparative 6A, dulaglutide | 26 |
| Comparative 6A, 8W dulaglutide | 11 |
| 7 | 5.6 |
| Comparative 7A | 2.6 |
| 8 | 4.4 |
| Comparative 8A | 1.2 |
| 9 | 70.5 |
| Comparative 9A | 41.3 |
| 10 | 31.2 |
| Comparative 10A | 16.8 |
| 11 | 34.1 |
| Comparative 11A | 12.5 |
| 12 | 62.9 |
| Comparative 12A | 13.7 |
| 13 | 32.1 |
| Comparative 13A | 14.7 |
| A | 9.4 |
| B | 0.57 |
| C | 32 |
| D | 12 |

All compounds have potency data that confirms that they are GLP-1 receptor agonists. Thus as regards in vitro potency they could all progress into further development.

Example 16: GLP-1 Receptor Binding

The purpose of this example is to test the receptor binding of GLP-1 compounds of the invention in vitro, along with selected comparative compounds. The receptor binding is a measure of affinity of a derivative for the human GLP-1 receptor.

The potencies of the GLP-1 derivatives of Examples 1-5 and 7-13 and the compounds of Comparative Examples 1A-5A, 7A-13A, and A-D were determined as described below.

Principle

The receptor binding to the human GLP-1 receptor was measured in a competitive binding assay. In this type of assay a labelled ligand (in this case $^{125}$I-GLP-1) is bound to the receptor. Each compound is added in a series of concentrations to isolated membranes containing the human GLP-1 receptor and displacement of the labelled ligand is monitored. The receptor binding is reported as the concentration at which half of the labelled ligand is displaced from the receptor, the IC$_{50}$ value. In order to test the binding of the derivatives to albumin, the assay is performed in a low concentration of human serum albumin (HSA) (max. 0.001% (w/v) final assay concentration as well as in the presence of a considerably higher concentration of HSA (2.0% (w/v) final assay concentration). An increase of the IC$_{50}$ value in the presence of HSA indicates an affinity to serum albumin and represents a method to predict a protracted pharmacokinetic profile of the test substance in animal models.

Materials

The following chemicals were used in the assay: Human serum albumin (HSA) (Sigma A1653), DMEM w/o phenol red (Gibco 11880-028), Pen/strep (Invitrogen 15140-122), G418 (Invitrogen 10131-027), 1 M Hepes (Gibco 15630), EDTA (Invitrogen 15575-038), PBS (Invitrogen 14190-094), fetal calf serum (Invitrogen 16140-071), EGTA, MgCl$_2$ (Merck 1.05832.1000), Tween 20 (Amresco 0850C335), SPA particles (wheat germ agglutinin (WGA) SPA beads, Perkin Elmer RPNQ0001), [$^{125}$I]-GLP-1]-(7-36)NH$_2$ (produced in-house), OptiPlate™-96 (Packard 6005290).

Buffer 1 consisted of 20 mM Na-HEPES plus 10 mM EDTA and pH was adjusted to 7.4. Buffer 2 consisted of 20 mM Na-HEPES plus 0.1 mM EDTA and pH was adjusted to 7.4. Assay buffer consisted of 50 mM HEPES supplemented with 5 mM EGTA, 5 mM MgCl$_2$, 0.005% w/v Tween 20 and pH was adjusted to 7.4. An 8% albumin stock consisted of HSA dissolved at 8% (w/v) in assay buffer. An 0.02% albumin stock consisted of HSA dissolved at 0.02% (w/v) in assay buffer.

Cell Culture and Membrane Preparation

The cells used in this assay (clone FCW467-12A) were BHK cells with BHKTS13 as a parent cell line. The cells express the human GLP-1 receptor.

The cells were grown at 5% CO$_2$ in DMEM, 10% w/v fetal calf serum, 1% w/v Pen/Strep (Penicillin/Streptomycin) and 1.0 mg/ml of the selection marker G418.

To make a membrane preparation the cells were grown to approximately 80% confluence. The cells were washed twice in phosphate-buffered saline and harvested. The cells were pelleted using a brief centrifugation and the cell pellet was kept on ice. The cell pellet was homogenised with ULTRA-THURRAX™ dispersing instrument for 20-30 seconds in a suitable amount of buffer 1 (e.g., 10 ml). The homogenate was centrifuged for 15 minutes. The pellet was re-suspended (homogenised) in 10 ml buffer 2 and centrifuged. This step was repeated once more. The resulting pellet was re-suspended in buffer 2 and the protein concentration was determined. The membranes were aliquoted and stored at minus 80° C.

Procedure

1. For the receptor binding assay in the presence of low HSA (0.005% (w/v)) 50 µl of the assay buffer was added to each well of an assay plate. Assay continued with step 3.
2. For the receptor binding assay in the presence of high HSA (2% (w/v)) 50 µl of the 8% (w/v) albumin stock was added to each well of an assay plate. Assay continued with step 3.
3. Test compounds were serially diluted to give the following concentrations: $8\times10^{-7}$ M, $8\times10^{-8}$ M, $8\times10^{-9}$ M, $8\times10^{-10}$ M, $8\times10^{-11}$ M, $8\times10^{-12}$ M and $8\times10^{-13}$ M. Twenty-five µl were added to appropriate wells in the assay plate.
4. Cell membrane aliquots were thawed and diluted to their working concentration. Fifty µl were added to each well in the assay plate.
5. WGA SPA beads were suspended in assay buffer at 20 mg/ml. The suspension was diluted to 10 mg/ml in assay buffer just prior to addition to the assay plate. Fifty µl were added to each well in the assay plate.
6. The incubation was started by adding 25 µl of 480 µM solution of [$^{125}$I]-GLP-1]-(7-36)NH$_2$ to each well of the assay plate. A 25 µl aliquot was reserved for measuring total counts/well.
7. The assay plate was incubated for 2 h at 30° C.
8. The assay plate was centrifuged for 10 min.
9. The assay plate was read in a Packard TopCount NXT instrument.

Calculations

Individual replicates were analysed using non-linear regression in GraphPad Prism. IC$_{50}$ values were calculated by the software and reported in nM. A minimum of two replicates was measured for each sample. The reported values are averages of all of the measured values for each compound.

Results

The following results were obtained:

TABLE 3

| GLP-1 receptor binding | | |
|---|---|---|
| Example no. | Low HSA IC$_{50}$ (nM) | High HSA IC$_{50}$ (nM) |
| 1 | 0.405 | 410 |
| Comparative 1A | 0.318 | 116 |
| 2 | 1.60 | 120 |
| Comparative 2A | 0.588 | 415 |
| 3 | 1.03 | 84.9 |
| Comparative 3A | 0.260 | 134 |
| 4 | 6.23 | 771 |
| Comparative 4A | 2.10 | 479 |
| 5 | 1.42 | 4.95 |
| Comparative 5A | 0.347 | 9.06 |
| 7 | 0.550 | 71.0 |
| Comparative 7A | 0.744 | 31.5 |
| 8 | 0.535 | 170 |
| Comparative 8A | 0.245 | 110 |
| 9 | 1.60 | 305 |
| Comparative 9A | 1.04 | 235 |
| 10 | 0.865 | 123 |
| Comparative 10A | 0.591 | 108 |
| 11 | 0.618 | 34.0 |
| Comparative 11A | 0.401 | 34.4 |
| 12 | 3.16 | 51.8 |
| Comparative 12A | 0.536 | 42.3 |
| 13 | 0.818 | 71.6 |
| Comparative 13A | 0.383 | 35.4 |
| A | 0.435 | 0.164 |
| B | 0.075 | 0.035 |
| C | 2.64 | 0.620 |
| D | 0.670 | 0.208 |

All compounds have IC$_{50}$ values that are fully acceptable, thus as regards in vitro receptor binding they could all progress into further development.

Example 17: Pharmacodynamic Study in Db/Db Mice

The purpose of the study was to verify the acute effect of a GLP-1 derivative of the invention on blood glucose (BG) and body weight (BW) in a diabetic setting.

The GLP-1 derivative of Example 2 was tested in a single dose study in an obese, diabetic mouse model (db/db mice) as described in the following. The derivative was tested at different doses, namely 0.3, 1.0, 3.0, 10, 30 or 100 nmol/kg.

The mice (from Taconic, Denmark), fed from birth with the diet NIH31 (NIH 31M Rodent Diet, commercially available from Taconic Farms, Inc., US, see www.taconic.com), were enrolled for the study at the age of approximately 10 weeks. Upon arrival at the animal unit at Måløv, Denmark, the mice were given free access to standard chow (e.g. Altromin 1324, Brogaarden, Gentofte, Denmark) and tap water and kept at 24° C. After 1-2 weeks of acclimatisation, the basal blood glucose was assessed twice on one day. The mice were allocated to treatment groups based on matching blood glucose levels and body weights. The mice were used in this experiment with a duration of 96 hours, and were re-used for an unrelated experiment once. After this last experiment the mice were euthanised.

The animals were grouped to receive treatment as follows: Vehicle, subcutaneously or GLP-1 derivative, 0.3, 1.0, 3.0, 10, 30 or 100 nmol/kg, subcutaneously, where vehicle was 50 mM sodium phosphate, 70 mM sodium chloride, 0.05% polysorbate 80, pH 7.4.

The GLP-1 derivative was dissolved in the vehicle, to dosing concentration of 0.05, 0.17, 0.5, 1.7, 5.0 or 17 nmol/ml. Animals were dosed once, at the start of the experiment, s.c. with a dose-volume of 6 ml/kg (i.e. 300 µl per 50 g mouse).

On the day of dosing, blood glucose was assessed at time −½h (9.00 am), the mice were weighed after this. The GLP-1 derivative was dosed at approximately 9:30 am (time 0). On the day of dosing, blood glucose was assessed at times 1, 2, 4 and 8 h (10:30 am, 11:30 am, 1:30 pm and 5:30 pm) after dosing.

On the following days, the blood glucose was assessed at time 24 h, 48 h, 72 h, and 96 h. On each day, the mice were weighed following blood glucose sampling.

The mice were weighed individually on a digital weighing scale.

Samples for the measurement of blood glucose were obtained from the tail tip capillary of conscious mice. Blood, 5 µl, was collected into heparinised capillaries and transferred to 250 µl glucose buffer (EKF system solution, Eppendorf, Germany). The glucose concentration was measured using the glucose oxidase method (glucose analyser Biosen 5040, EKF Diagnostic, GmbH, Barleben, Germany). The samples were kept at room temperature for up to 1 h until analysis. If analysis had to be postponed, samples were kept at 4° C. for a maximum of 24 h.

Dose response curves for delta blood glucose and delta body weight versus time were drawn up for each of the single doses of the GLP-1 derivative. The delta refers to the actual blood glucose/body weight at a given time, minus baseline, where baseline is the level of blood glucose and body weight at time 0. Thus in these curves y=0 represents baseline.

To get an indication of the effect of the GLP-1 derivative on blood glucose and body weight, the area under the curve for delta blood glucose from 0 until 24 hours (AUC ΔBG$_{24h}$) and delta body weight gain at 24 hours post dosing (ΔBW$_{24h}$) were calculated, for each of the individual dose response curves, and the Effective Doses 50% (ED50, dose of GLP-1 derivative that gives a response halfway between baseline and maximal effect) were calculated for AUC ΔBG$_{24h}$ and ΔBW$_{24h}$.

The resulting ED50 values are shown in Table 4 below (averages of 4-6 determinations).

TABLE 4

| ED50 values for the effects on blood glucose and body weight in db/db mice | | |
|---|---|---|
| Derivative of Example no. | ED50 AUC ΔBG$_{24h}$ (nmol/kg) | ED50 ΔBW$_{24h}$ (nmol/kg) |
| 2 | 2.44 | 4.57 |

The GLP-1 derivative of Example 2 showed an effect in vivo by dose dependently decreasing blood glucose as well as body weight.

Example 18: Fully Recombinant Vs Semi-Recombinant Process, Expression Yields

Background

The purpose of this example is to describe a fully recombinant process for expression of the DPP-iv stable (8W) peptide parts of the GLP-1 derivatives of the invention.

A known process for preparing GLP-1 peptides that have been DPP-iv stabilised by incorporation of one or more non-coded amino acids in the N-terminus (e.g., substitution of native Ala at position 8 with Aib) is the socalled semi-recombinant process. According to this process, a precursor peptide is first prepared recombinantly (e.g, a precursor GLP-1(9-37) peptide in which the two N-terminal amino acids have been deleted). And in a next step the lacking two N-terminal amino acids which include the non-coded amino acid(s) (e.g., the dipeptide His-Aib) is added to the N-terminus of the precursor peptide by a process called ligation. Overall this two-step preparation process is referred to as the semi-recombinant process. The semi-recombinant process is described in, e.g., WO 2009/083549 (recombinant expression of precursor peptide) and WO 2013/098191 (ligation). The present example also compares expression yield for the fully recombinant expression with expression yield for the expression step of the semi-recombinant process.

More in particular, the yields of the fully recombinant expression of two GLP-1 peptides incorporated in derivatives of the invention (SEQ ID NO: 7 and SEQ ID NO: 9) are compared with the yields of the expression of the corresponding precursor peptides in which the two N-terminal amino acids are lacking (SEQ ID NO: 22 and SEQ ID NO: 23, respectively).

In the experimental procedure described below an N-terminal extension of DVKPGQPMYDDDDK (SEQ ID NO: 24) has been added to each of these four GLP-1 peptides. This N-terminal extension is used for optimisation purposes that are unrelated and not relevant for the present application.

Experimental

Plasmids were constructed containing the TDH3 promoter, the gene encoding the MFalpha pre-pro-peptide, the respective GLP-1 peptide extended N-terminally with the peptide DVKPGQPMYDDDDK (SEQ ID NO: 24), a minimal 2 micron region for maintenance in yeast, and a selectable marker, namely the TPI gene from *S. pombe* (see FIG. 1). In FIG. 1 AMP-R stands for the ampicillin resistance gene (beta-lactamase), and STB refers to a series of small repeats (sometimes referred to as REP3) serving the purpose of distributing the plasmids between daughter cells.

These plasmids were introduced into a *Saccharomyces cerevisiae* strain lacking the TPI1 gene, allowing for selection of transformants harbouring the plasmid on media containing glucose as sole carbon source. Transformants were thereafter cultivated in continuous culture and the culture supernatants were analyzed by UPLC for concentration of secreted GLP-1 peptide.

Table 5 below shows mean expression yield of the fully recombinant expression process, normalised relative to the mean expression yield obtained in the first step of the semi-recombinant process in which the corresponding precursor peptide is prepared.

TABLE 5

| GLP-1 peptide* | Yield Fully recombinant | Yield Semi-recombinant |
|---|---|---|
| SEQ ID NO: 7 | 108 | |
| SEQ ID NO: 22 | | 100 |
| SEQ ID NO: 8 | 94 | |
| SEQ ID NO: 23 | | 100 |

*All with N-terminal extension of DVKPGQPMYDDDDK (SEQ ID NO: 24)

The results show that the yield of the fully recombinant expression process is on par with the yield of the first step of the semi-recombinant expression process. Considering the fact that when the fully recombinant process is used step two of the semi-recombinant process becomes redundant this translates into an improvement in production economy for the fully recombinant process as compared to the semi-recombinant process.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A derivative of formula I:

(P-L)$_U$-B-GLP1, wherein GLP1 is a GLP-1 analogue having a Trp at a position corresponding to position 8 of GLP-1(7-37) (SEQ ID NO: 1), (P-L) is a substituent attached to a Lys residue of the GLP-1 analogue via an optional Branching group (B) and comprising a Protracting moiety (P) and a Linker (L), U represents the number of substituents (P-L) in the derivative and is 1 or 2, wherein each substituent (P-L) comprises (i) a Protracting moiety (P) selected from Chem. 10, Chem. 11, Chem. 12, Chem. 13, and Chem. 14:

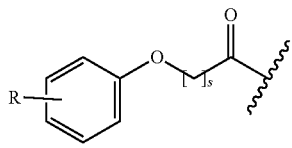

Chem. 10

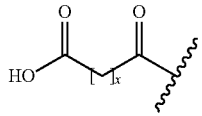

Chem. 11

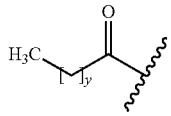

Chem. 12

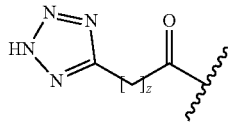

Chem. 13

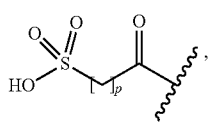

Chem. 14 and (ii) a Linker (L) comprising at least one linker element selected from Chem. 15, Chem. 16, Chem. 17, and Chem. 18:

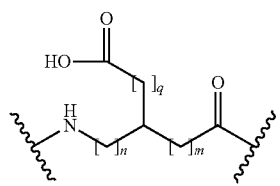

Chem. 15

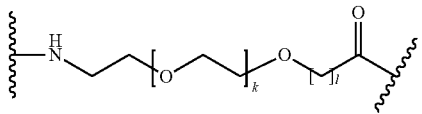

Chem. 16

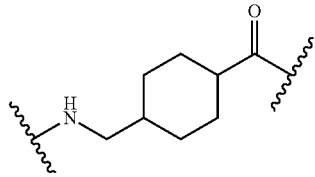

Chem. 17

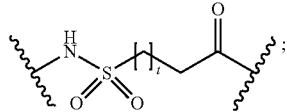

Chem. 18 wherein
R is —COOH;
each of s, x, y, z, and p independently represents an integer in the range of 8-20;
each of n, m, and q independently represents an integer in the range of 0-4; and
each of k, l, and t independently represents an integer in the range of 1-5; and (iii) wherein the Branching group (B) if present comprises a Branched linker (BL) selected from Chem. 19 and Chem. 20:

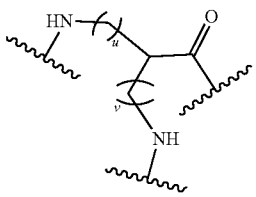

Chem. 19

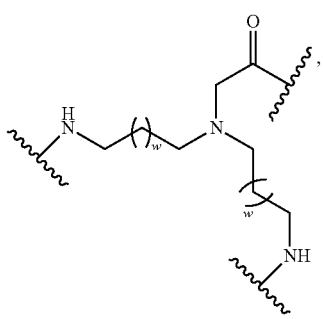

Chem. 20 wherein u and v independently represents an integer in the range of 0-5 and each w represents an integer in the range of 0-2, with the provisos that when u is 0 v is an integer in the range of 1-5, and when v is 0 u is an integer in the range of 1-5;

or a pharmaceutically acceptable salt, amide, or ester thereof.

2. The derivative of claim 1, wherein the GLP-1 analogue comprises a peptide of formula II (SEQ ID NO: 25):

$Xaa_7$-Trp-Glu-Gly-Thr-$Xaa_{12}$-Thr-Ser-Asp-$Xaa_{16}$-Ser-$Xaa_{18}$-$Xaa_{19}$-$Xaa_{20}$-Glu-$Xaa_{22}$-$Xaa_{23}$-Ala-$Xaa_{25}$-$Xaa_{26}$-$Xaa_{27}$-Phe-Ile-$Xaa_{30}$-$Xaa_{31}$-Leu-$Xaa_{33}$-$Xaa_{34}$-$Xaa_{35}$-$Xaa_{36}$-$Xaa_{37}$-$Xaa_{38}$-$Xaa_{39}$-$Xaa_{40}$-$Xaa_{41}$-$Xaa_{42}$, wherein $Xaa_7$ is L-histidine, (S)-2-Hydroxy-3-(1H-imidazol-4-yl)-propionic acid, D-histidine, deamino-histidine, homo-histidine, $N^\alpha$-acetyl-histidine, $N^\alpha$-formyl-histidine, $N^\alpha$-methyl-histidine, 3-pyridylalanine, 2-pyridylalanine, or 4-pyridylalanine;

$Xaa_{12}$ is Phe or Leu;

$Xaa_{16}$ is Val or Leu;

$Xaa_{18}$ is Ser, Arg, Val, or Leu;

$Xaa_{19}$ is Tyr or Gln;

$Xaa_{20}$ is Leu or Met;

$Xaa_{22}$ is Gly or Glu;

$Xaa_{23}$ is Gln, Glu, or Arg;

$Xaa_{25}$ is Ala or Val;

$Xaa_{26}$ is Arg or Lys;

$Xaa_{27}$ is Glu, Lys, or Leu;

$Xaa_{30}$ is Ala, Glu, or Arg;

$Xaa_{31}$ is Trp or His;

$Xaa_{33}$ is Val;

$Xaa_{34}$ is Arg, His, Asn, or Gln;

$Xaa_{35}$ is Gly or Ala;

$Xaa_{36}$ is Arg, Lys, or Gly;

$Xaa_{37}$ is Gly, Lys, Pro, or absent;

$Xaa_{38}$ is Ser, Gly, Ala, Glu, Pro, Lys, or absent;

$Xaa_{39}$ is Ser, Gly, Ala, Glu, Pro, or absent;

$Xaa_{40}$ is Ser, Gly, Ala, Glu, Pro, or absent;

$Xaa_{41}$ is Ser, Gly, Ala, Glu, Pro, or absent; and $Xaa_{42}$ is Lys or absent;

with the proviso that if one of $Xaa_{37}$, $Xaa_{38}$, $Xaa_{39}$, $Xaa_{40}$, $Xaa_{41}$, or $Xaa_{42}$ is absent then each subsequent amino acid residue is also absent; and with the proviso that at least one of $Xaa_{26}$, $Xaa_{27}$, $Xaa_{36}$, $Xaa_{37}$, $Xaa_{38}$, or $Xaa_{42}$ is Lys;

or a pharmaceutically acceptable salt, amide, or ester thereof.

3. The derivative of claim 1, which has formula Ia:

(P-L)-GLP1;   Formula Ia:

or a pharmaceutically acceptable salt, amide, or ester thereof.

4. The derivative of claim 1, which has formula Ib:

(P-L)$_2$-GLP1;   Formula Ib:

or a pharmaceutically acceptable salt, amide, or ester thereof.

5. The derivative of claim 1, which has formula Ic:

(P-L)$_2$>BL-PL-GLP1,   Formula Ic:

wherein (i) >BL is a Branched linker as defined in claim 1, and (ii) PL is a Pre linker which comprises Chem. 16:

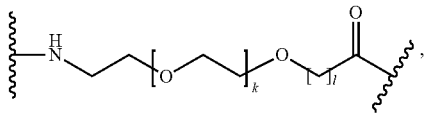

wherein each of k and l independently represents an integer in the range of 1-5;

or a pharmaceutically acceptable salt, amide, or ester thereof.

6. The derivative of claim 1, which has formula Id:

(P-L)$_2$>BL-GLP1,   Formula Id:

wherein >BL is a Branched linker as defined in claim 1;

or a pharmaceutically acceptable salt, amide, or ester thereof.

7. A derivative selected from the following:

N{Epsilon-36}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl],N{Epsilon-37}-[2-[2-[2-[[2-[2-[2-[[(4S)-4-carboxy-4-[10-(3-carboxyphenoxy)decanoylamino]butanoyl]amino]ethoxy]ethoxy]acetyl]amino]ethoxy]ethoxy]acetyl]-[Trp8,Glu22,Arg26,Arg34,Lys36,Lys37]-GLP-1-(7-37)-peptide, Chem. 21, derivative of SEQ ID NO: 5:
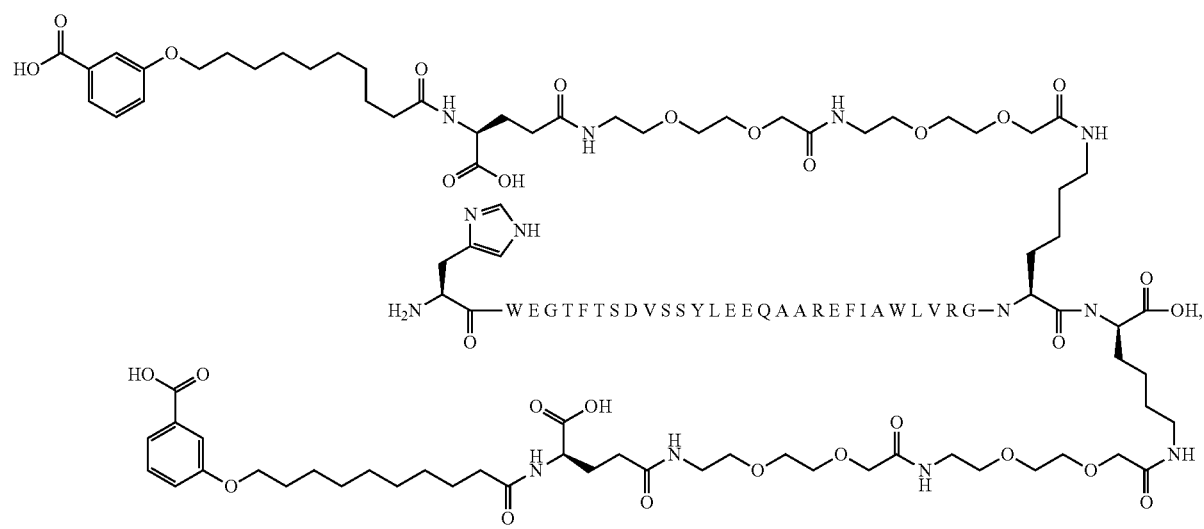
N{Epsilon-26}-[2-[2-[2-[[2-[2-[2-[[(4S)-4-carboxy-4-(17-carboxyheptadecanoylamino)butanoyl]amino]ethoxy]ethoxy]acetyl]amino]ethoxy]ethoxy]acetyl]-[Trp8,Arg34]-GLP-1-(7-37)-peptide,
Chem. 22, derivative of SEQ ID NO: 7:

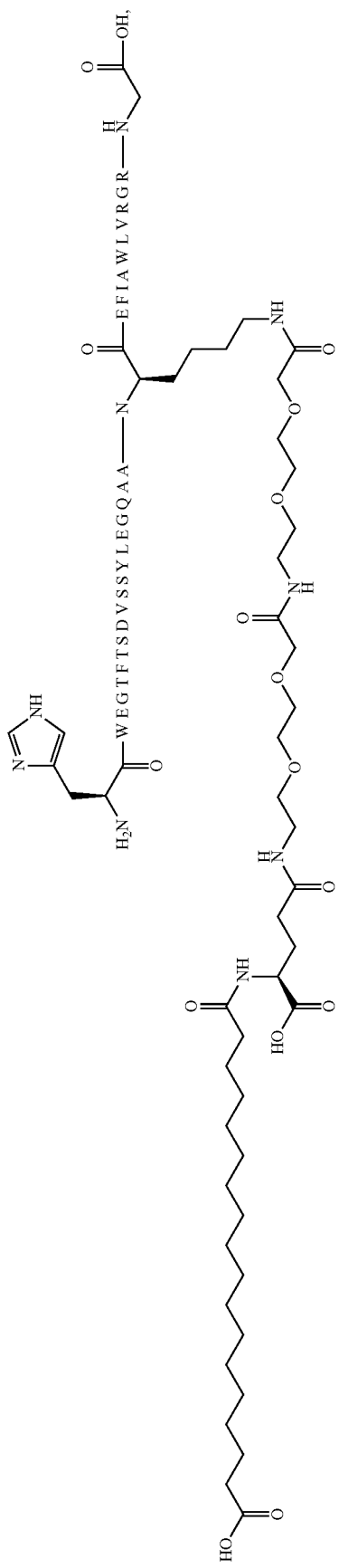

N{Epsilon-27}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl],N{Epsilon-36}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Trp8,Glu22,Arg26,Lys27,Glu30,Arg34,Lys36]-GLP-1-(7-37)-peptidyl-Glu-Gly,
Chem. 23, derivative of SEQ ID NO: 9:

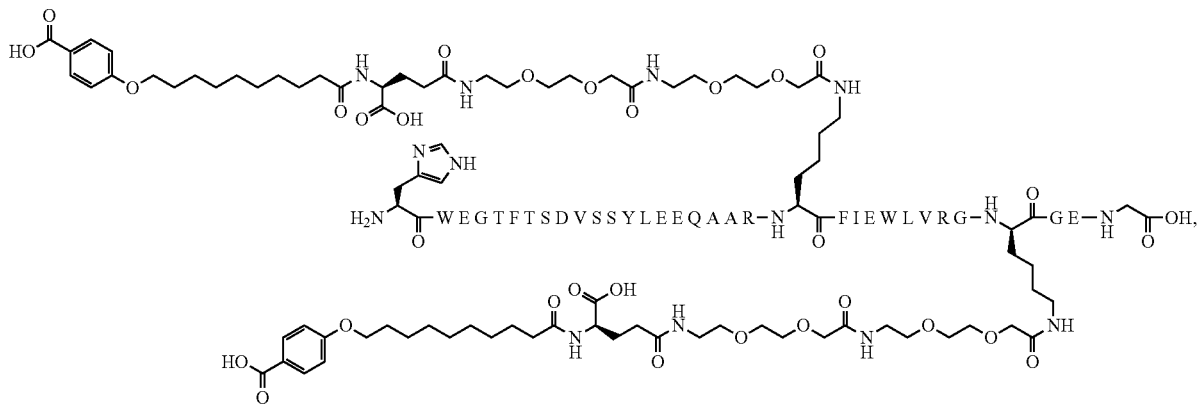

N{Epsilon-26}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl],N{Epsilon-37}-[2-[2-[2-[[2-[2-[2-[[(4S)-4-carboxy-4-[10-(4-carboxyphenoxy)decanoylamino]butanoyl]amino]ethoxy]ethoxy]acetyl]amino]ethoxy]ethoxy]acetyl]-[Trp8,Arg34,Lys37]-GLP-1-(7-37)-peptide,
Chem. 24, derivative of SEQ ID NO: 11:

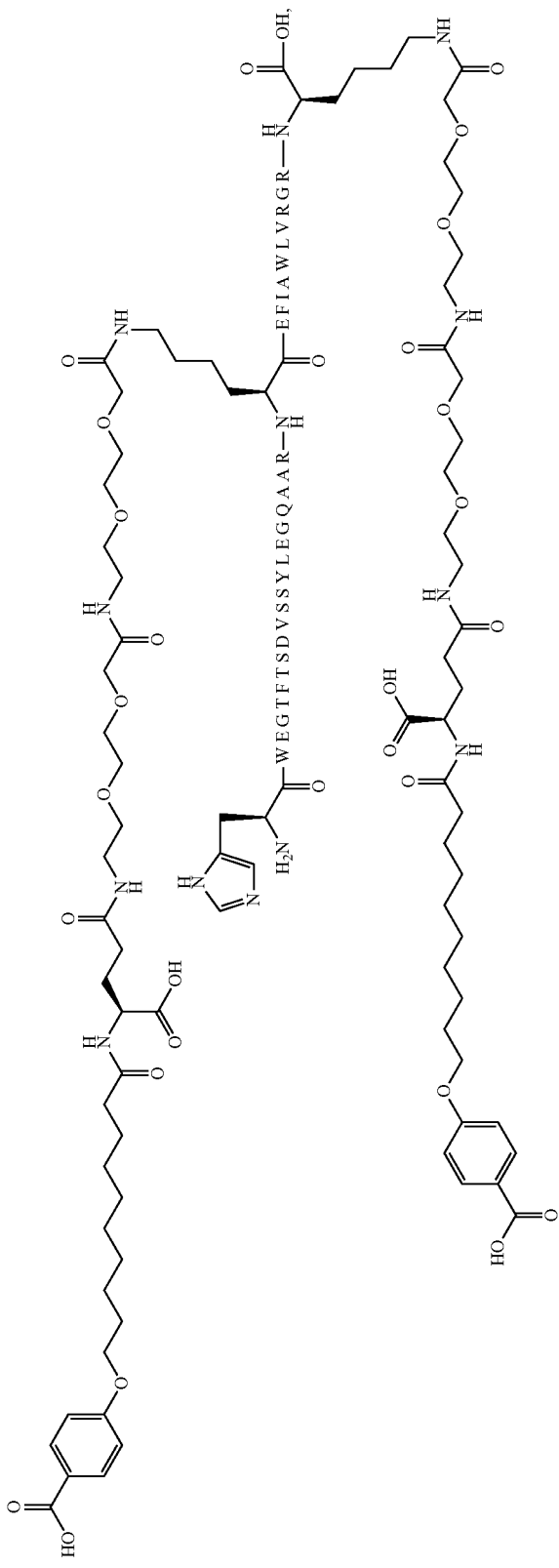

N{Epsilon-26}-[(4S)-4-carboxy-4-(hexadecanoylamino)butanoyl]-[Trp8,Arg34]-GLP-1-(7-37)-peptide,
Chem. 25, derivative of SEQ ID NO: 7:

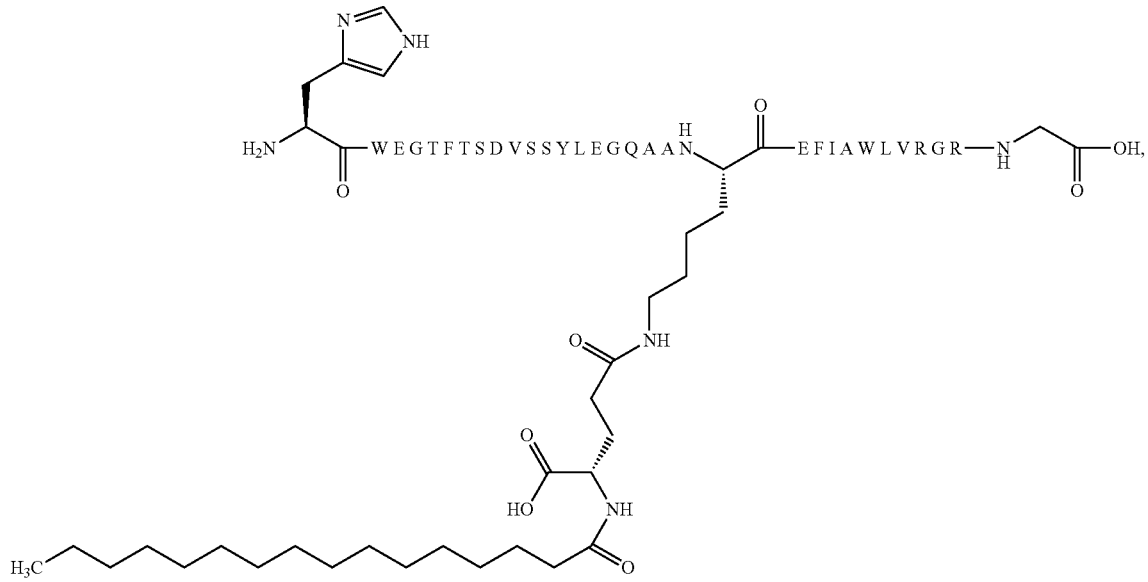

N{Epsilon-36}-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl],N{Epsilon-37}-[2-[2-[2-[[2-[2-[2-[[2-[2-[2-[[2-[2-[2-[[(4S)-4-carboxy-4-(13-carboxytridecanoylamino)butanoyl]amino]ethoxy]ethoxy]acetyl]amino]ethoxy]ethoxy]acetyl]amino]ethoxy]ethoxy]acetyl]amino]ethoxy]ethoxy]acetyl]-[Trp8,Glu22,Arg26,Arg34,Lys36,Lys37]-GLP-1-(7-37)-peptide,
Chem. 26, derivative of SEQ ID NO: 5:

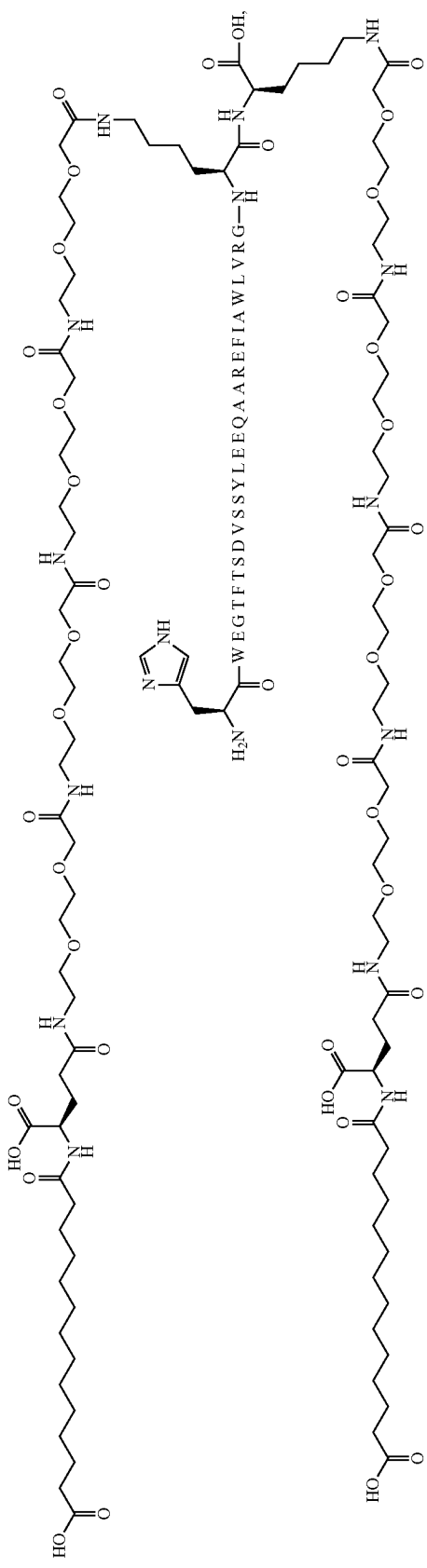

N{Epsilon-36}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl],N{Epsilon-37}-[2-[2-[2-[[2-[2-[2-[[(4S)-4-carboxy-4-[11-(4-carboxyphenoxy)undecanoylamino]butanoyl]amino]ethoxy]ethoxy]acetyl]amino]ethoxy]ethoxy]acetyl]-[Trp8,Glu22,Arg26,Arg34,Lys36,Lys37]-GLP-1-(7-37)-peptide, Chem. 27, derivative of SEQ ID NO: 5:

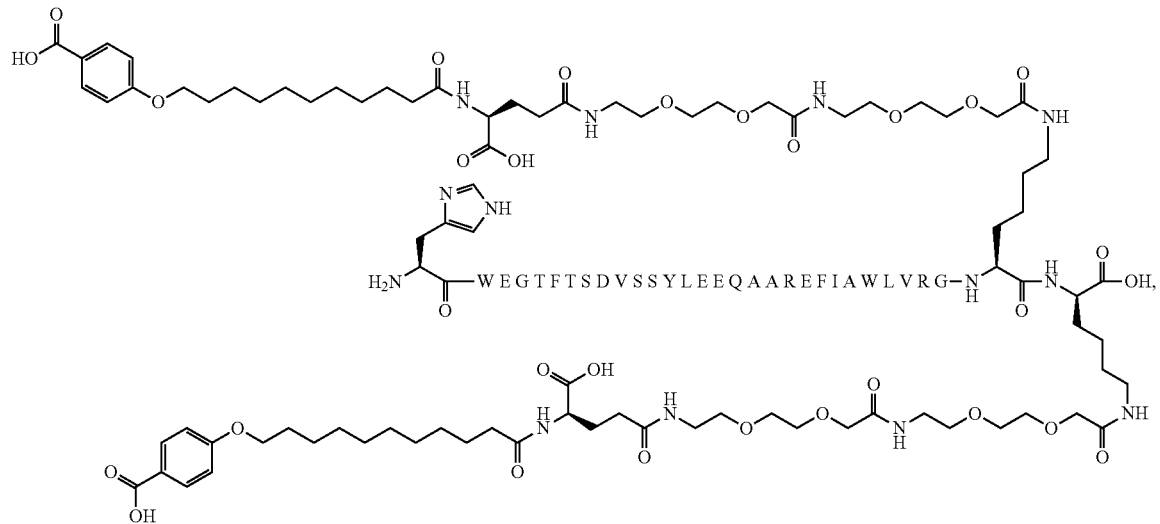

N{Alpha}([Trp8,Glu22,Arg26,Arg34]-GLP-1-(7-37)-peptidyl)-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys-Gly-Gly-Ser-N{Epsilon}[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]Lys, Chem. 28, derivative of SEQ ID NO: 16:

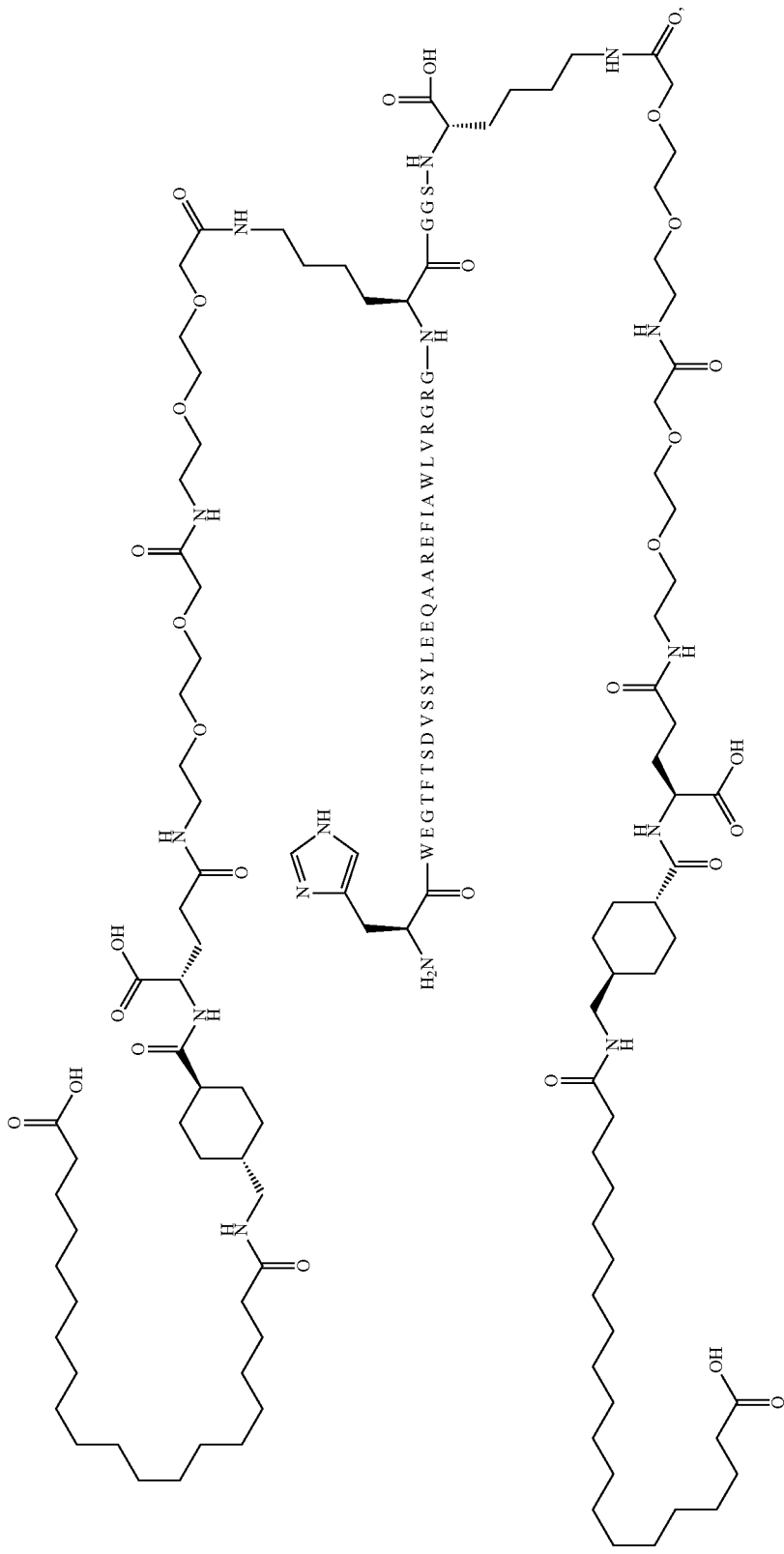

N{Epsilon-37}-[(2S)-2,6-bis[[2-[2-[2-[[2-[2-[2-[[2-[2-[2-[[2-[2-[2-[[2-[2-[2-[[(4S)-4-carboxy-4-[[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]hexanoyl]-[Trp8,Glu22,Arg26,Arg34,Lys37]-GLP-1-(7-37)-peptide, Chem. 29, derivative of SEQ ID NO: 18:

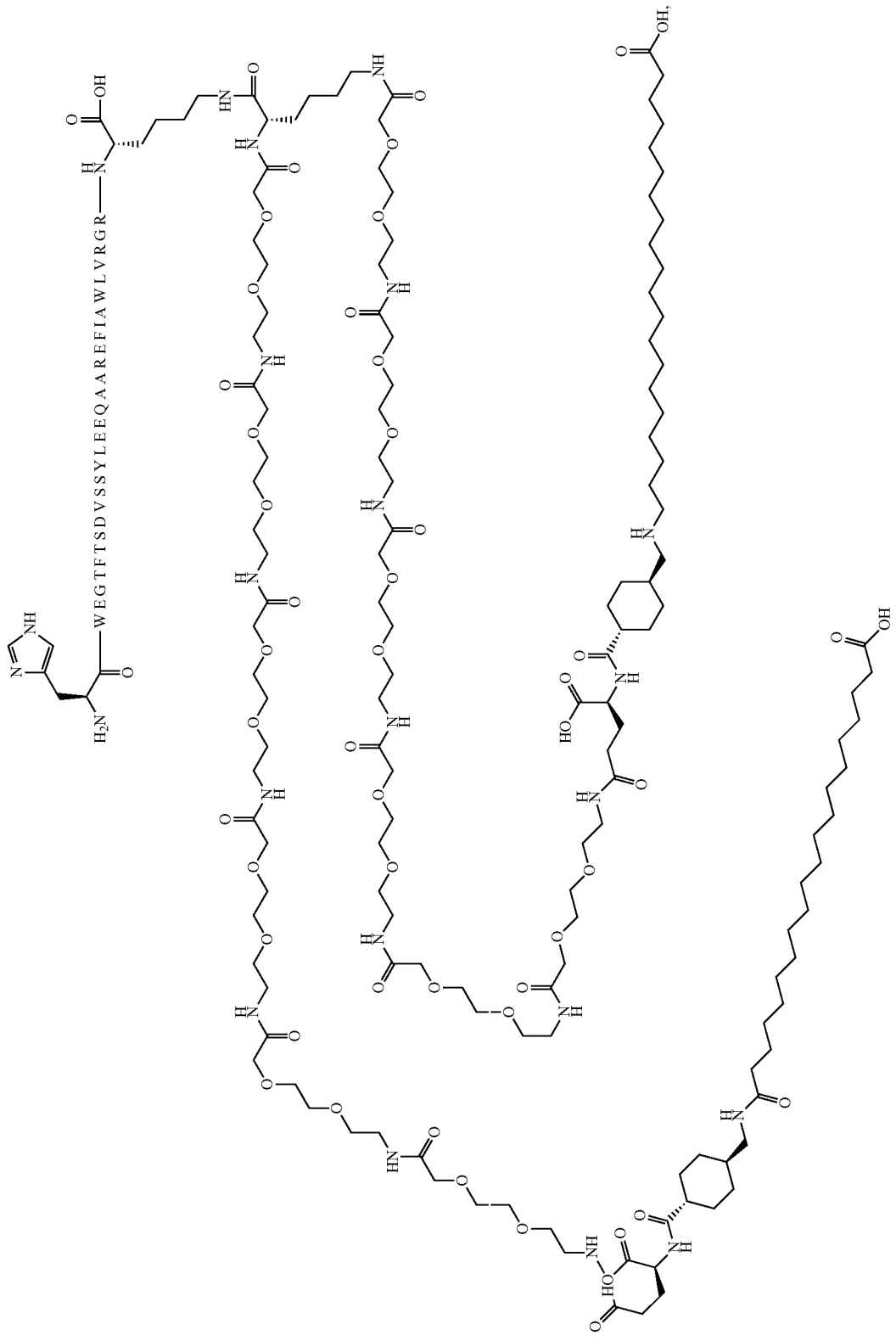

N{Alpha}([Trp8,Glu22,Arg26,Arg34,Pro37]-GLP-1-(7-37)-peptidyl)-N{Epsilon}[2-[bis[3-[[2-[2-[2-[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]Lys,
Chem. 30, derivative of SEQ ID NO: 20:

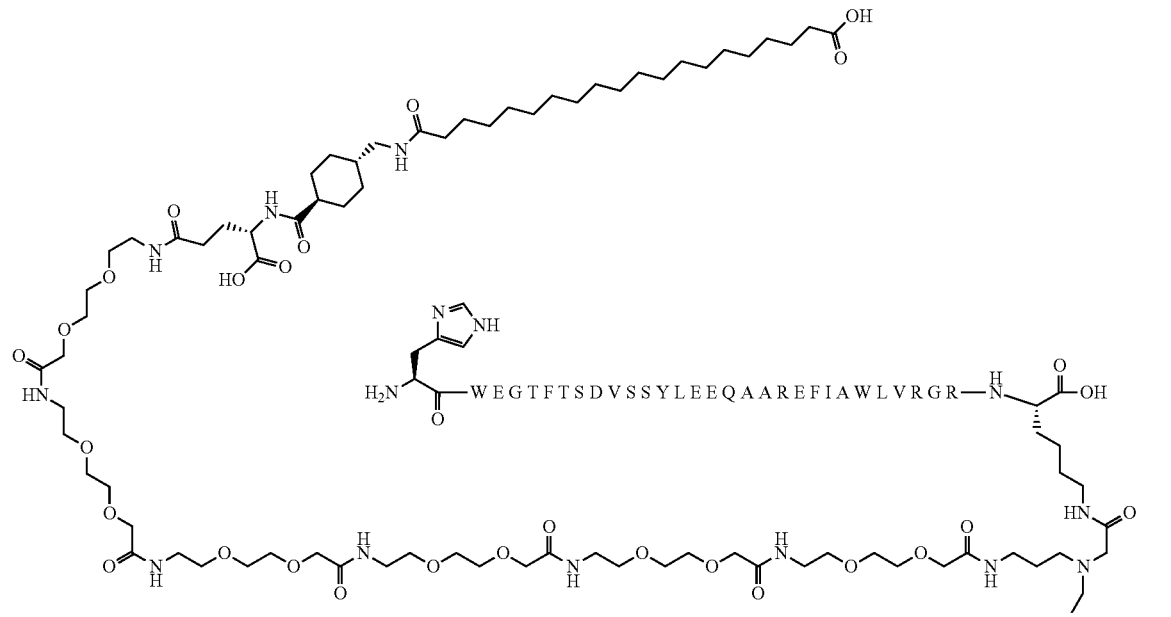

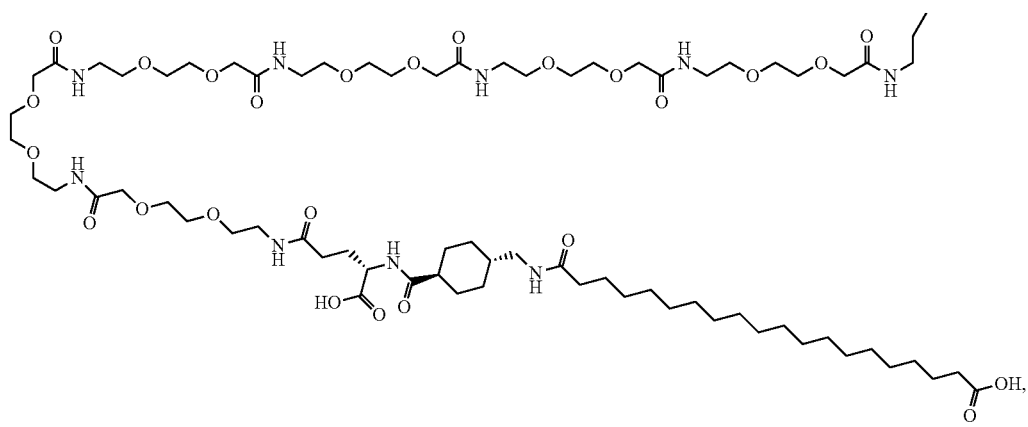

N{Epsilon-37}-[2-[2-[2-[[2-[2-[2-[[(2S)-2,6-bis[[2-[2-[2-[[2-[2-[2-[[2-[2-[2-[[2-[2-[2-[[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]hexanoyl]amino]ethoxy]ethoxy]acetyl]amino]ethoxy]ethoxy]acetyl]-[Trp8,Glu22,Arg26,Arg34,Lys37]-GLP-1-(7-37)-peptide,
Chem. 31, derivative of SEQ ID NO: 18:

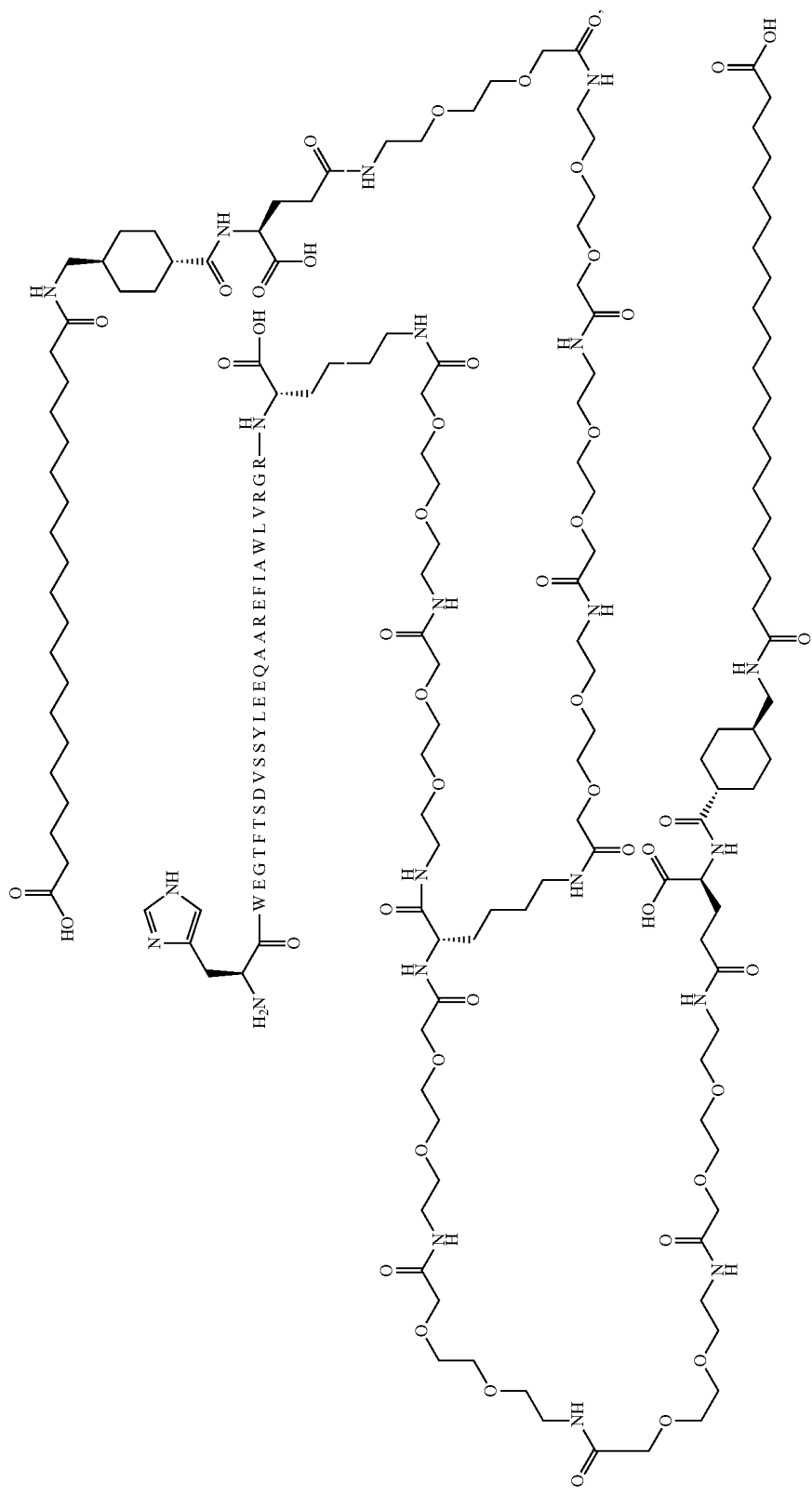

N{Epsilon-37}-[2-[2-[2-[[2-[2-[2-[[2-[bis[3-[[2-[2-[2-[[2-[2-[2-[[2-[2-[2-[[2-[2-[(4S)-4-carboxy-4-[[4-[(19-carboxynonadecanoylamino)methyl]cyclohexanecarbonyl]amino]butanoyl]amino]ethoxy]ethoxy]acetyl]amino]ethoxy]ethoxy]acetyl]amino]ethoxy]ethoxy]acetyl]amino]ethoxy]ethoxy]acetyl]amino]propyl]amino]acetyl]amino]ethoxy]ethoxy]acetyl]amino]ethoxy]ethoxy]acetyl]-[Trp8,Glu22,Arg26,Arg34,Lys37]-GLP-1-(7-37)-peptide, and Chem. 32, derivative of SEQ ID NO: 18:

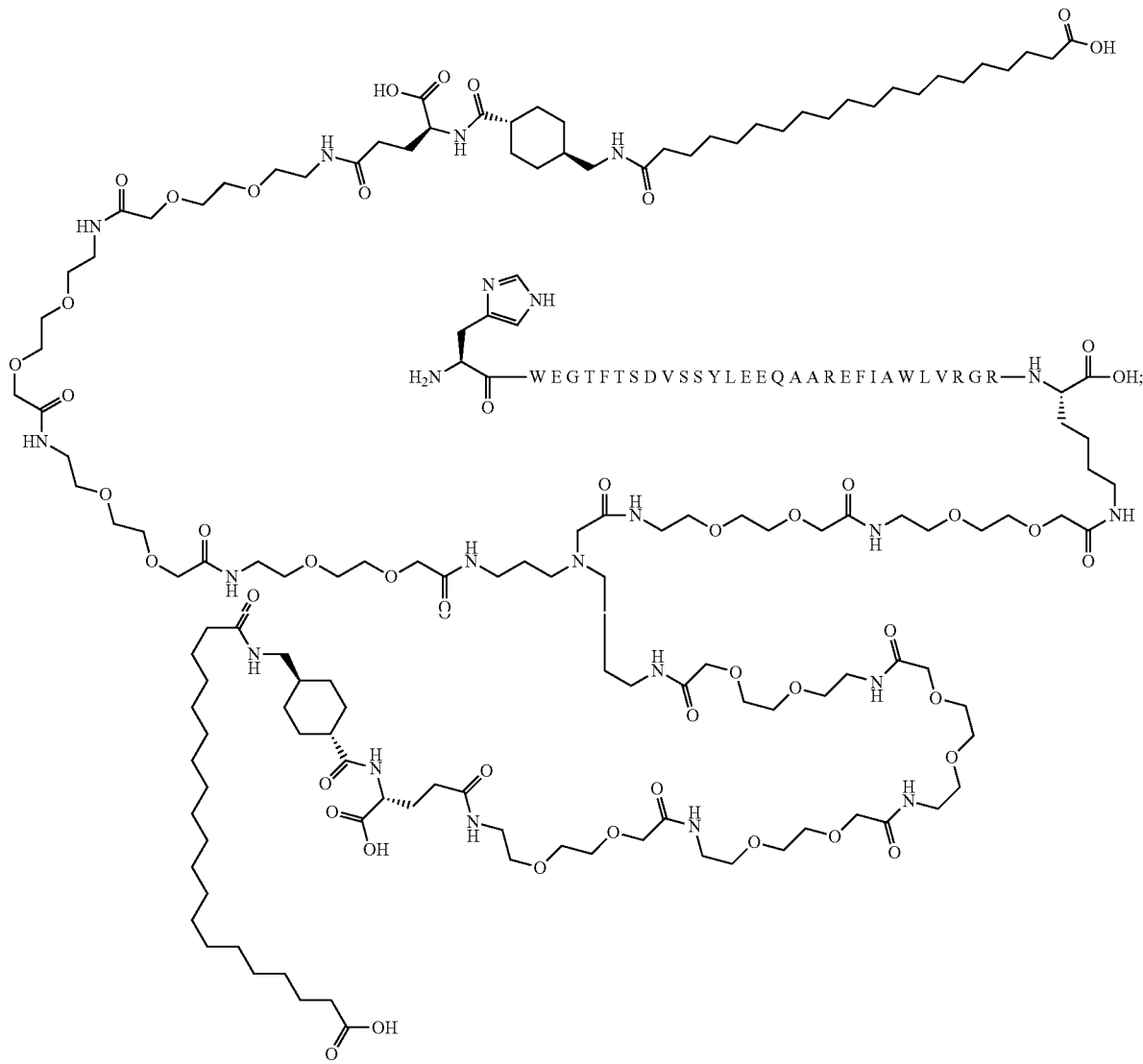

or a pharmaceutically acceptable salt, amide, or ester thereof.

8. A GLP-1 analogue selected from SEQ ID NO:4, SEQ ID NO:5, SEQ ID NO: 7, SEQ ID NO: 9, SEQ ID NO: 11, SEQ ID NO:15, amino acids 1-275 of SEQ ID NO: 15, SEQ ID NO: 16, SEQ ID NO: 18, and SEQ ID NO:20; or a pharmaceutically acceptable salt, amide, or ester thereof.

9. A method of preparing a derivative of claim 1, which comprises the step of recombinantly producing a GLP-1 analogue having Trp at a position corresponding to position 8 of GLP-1(7-37) (SEQ ID NO: 1).

10. The method of claim 9, wherein the GLP-1 analogue has GLP-1 activity and is DPP-IV stabilised.

11. The method of claim 9, which further comprises the step of purifying the recombinantly produced GLP-1 analogue.

12. The method of claim 9, which further comprises the step of attaching a substituent to a Lys residue of the GLP-1 analogue and purifying the resulting GLP-1 derivative.

13. A pharmaceutical composition comprising a derivative according to claim 1, and a pharmaceutically acceptable excipient.

14. A method comprising:
    (i) prevention and/or treatment of all forms of diabetes, and/or for reduction of HbA1C;
    (ii) delaying or preventing diabetic disease progression;
    (iii) improving β-cell function;
    (iv) prevention and/or treatment of cognitive disorders and/or neurodegenerative disorders;
    (v) prevention and/or treatment of eating disorders by decreasing food intake, reducing body weight, suppressing appetite, and/or inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity;

(vi) prevention and/or treatment of diabetic complications;

(vii) improving lipid parameters; increasing HDL; lowering small, dense LDL; lowering VLDL; lowering triglycerides; lowering cholesterol; lowering plasma levels of lipoprotein a (Lp(a)) in a human; and/or inhibiting generation of apolipoprotein a (apo(a)) in vitro and/or in vivo;

(viii) prevention and/or treatment of cardiovascular diseases; and/or reduction of blood pressure;

(ix) prevention and/or treatment of gastrointestinal diseases dyspepsia, and/or gastric ulcers; and/or inflammation, psoriasis, psoriatic arthritis, rheumatoid arthritis, and/or systemic lupus erythematosus;

(x) prevention and/or treatment of critical illness, a critical illness poly-nephropathy (CIPNP) patient, and/or a potential CIPNP patient; prevention of development of critical illness or CIPNP; prevention, treatment and/or cure of systemic inflammatory response syndrome (SIRS) in a patient; prevention or reduction of the likelihood of a patient suffering from bacteraemia, septicaemia, and/or septic shock during hospitalisation; and/or stabilising blood glucose, insulin balance and optionally metabolism in intensive care unit patients with acute illness;

(xi) prevention and/or treatment of polycystic ovary syndrome (PCOS);

(xii) prevention and/or treatment of cerebral disease, cerebral ischemia, cerebral haemorrhage, and/or traumatic brain injury;

(xiii) prevention and/or treatment of sleep apnoea; and/or (xiv) prevention and/or treatment of alcohol abuse and/or drug abuse, wherein a subject in need of such method is administered a pharmaceutically effective amount of pharmaceutical composition comprising a derivative according to claim 1.

15. A method comprising: the treatment or prevention of hyperglycemia, type 2 diabetes, impaired glucose tolerance, type 1 diabetes, non-insulin dependent diabetes, MODY (maturity onset diabetes of the young), gestational diabetes, Alzheimer's disease, Parkinson's disease, multiple sclerosis, osteoarthritis, urine incontinence, angiopathy, neuropathy, peripheral neuropathy, nephropathy, retinopathy, dyslipidemia, syndrome X, atherosclerosis, myocardial infarction, coronary heart disease, reperfusion injury, stroke, cerebral ischemia, early cardiac or early cardiovascular disease, left ventricular hypertrophy, coronary artery disease, hypertension, essential hypertension, acute hypertensive emergency, cardiomyopathy, heart insufficiency, exercise intolerance, acute and/or chronic heart failure, arrhythmia, cardiac dysrhythmia, syncopy, angina pectoris, cardiac bypass and/or stent reocclusion, intermittent A claudication, atherosclerosis obliterans, diastolic dysfunction/and/or systolic dysfunction, reduction of systolic blood pressure, inflammatory bowel disease, short bowel syndrome, Crohn's disease, or colitis;

wherein a subject in need of such method is administered a pharmaceutically effective amount of pharmaceutical composition comprising a derivative according to claim 1.

* * * * *

UNITED STATES PATENT AND TRADEMARK OFFICE
CERTIFICATE OF CORRECTION

PATENT NO. : 10,946,074 B2  
APPLICATION NO. : 16/077759  
DATED : March 16, 2021  
INVENTOR(S) : Jacob Kofoed et al.

Page 1 of 2

It is certified that error appears in the above-identified patent and that said Letters Patent is hereby corrected as shown below:

In the Claims

At Column 169, Claim number 7, entire page, amend as follows:

"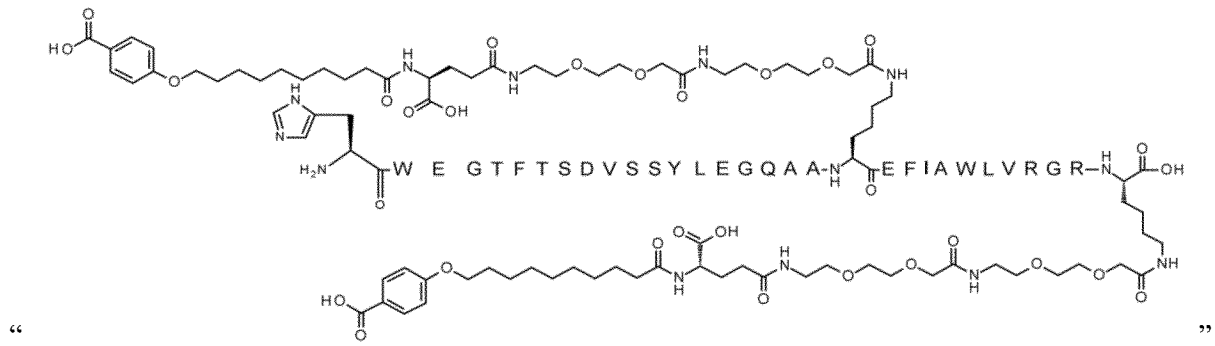"

Signed and Sealed this  
Fifteenth Day of June, 2021

Drew Hirshfeld  
*Performing the Functions and Duties of the*  
*Under Secretary of Commerce for Intellectual Property and*  
*Director of the United States Patent and Trademark Office*

CERTIFICATE OF CORRECTION (continued)
U.S. Pat. No. 10,946,074 B2

At Column 184, Claim number 7, Line 11-57, amend as follows:

"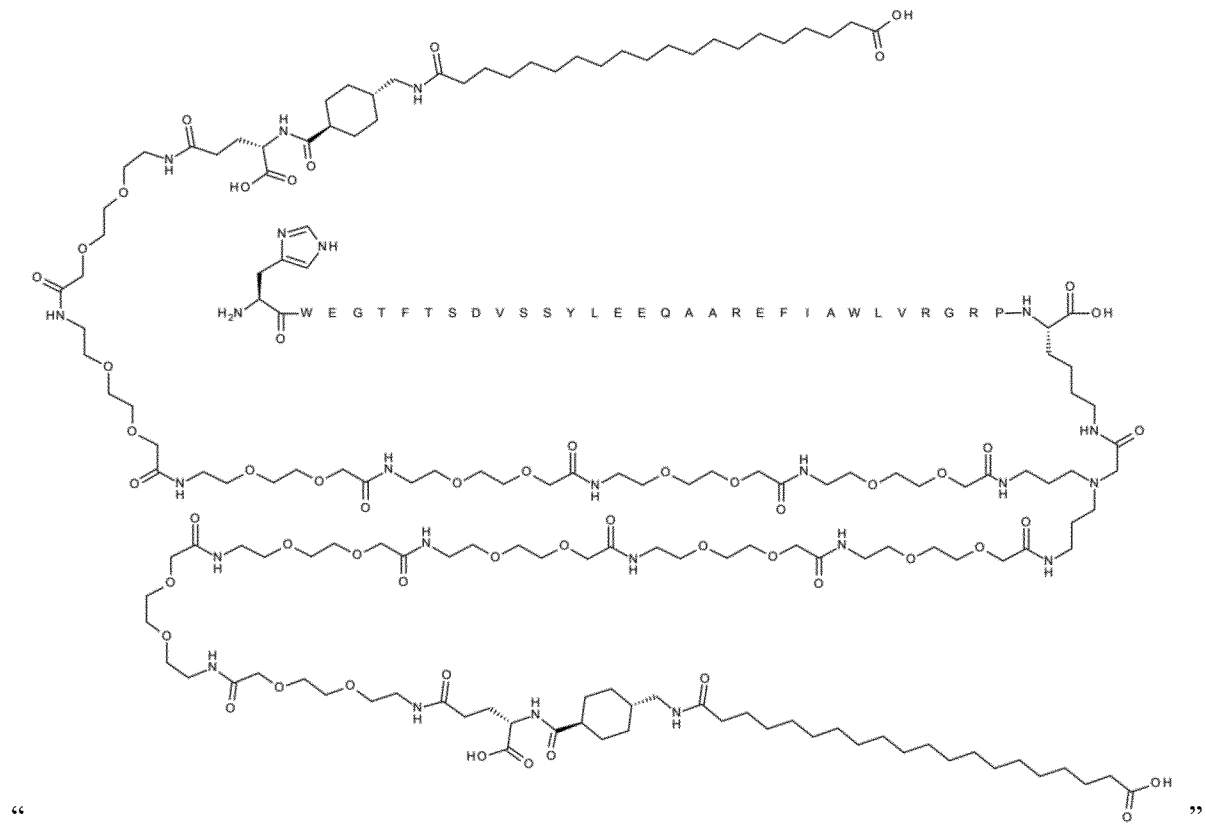"

At Column 190, Claim number 15, Line 24, amend as follows:
"...or stent reocclusion, intermittent claudication, atherosclerosis..."

SEQUENCE LISTING

```
<160> NUMBER OF SEQ ID NOS: 29

<210> SEQ ID NO 1
<211> LENGTH: 31
<212> TYPE: PRT
<213> ORGANISM: Homo sapiens
<220> FEATURE:
<221> NAME/KEY: mat_peptide
<222> LOCATION: (1)..(31)

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 2
<211> LENGTH: 31
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(31)

<400> SEQUENCE: 2

His Pro Glu Gly Thr Phe Thr Ser Asp Val Ser Ser Tyr Leu Glu Glu
1               5                   10                  15

Gln Ala Ala Arg Glu Phe Ile Ala Trp Leu Val Lys Gly Arg Gly
            20                  25                  30

<210> SEQ ID NO 3
<211> LENGTH: 31
<212> TYPE: PRT
<213> ORGANISM: Artificial sequence
<220> FEATURE:
```

```
<223> OTHER INFORMATION: GLP-1 analogue

<400> SEQUENCE: 3

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 4
<211> LENGTH: 31
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(31)

<400> SEQUENCE: 4

His Trp Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 5
<211> LENGTH: 31
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(31)

<400> SEQUENCE: 5

His Trp Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Lys
            20                  25                  30

<210> SEQ ID NO 6
<211> LENGTH: 31
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(31)
<220> FEATURE:
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 6

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Lys Lys
            20                  25                  30

<210> SEQ ID NO 7
<211> LENGTH: 31
<212> TYPE: PRT
<213> ORGANISM: Artificial sequence
<220> FEATURE:
<223> OTHER INFORMATION: GLP-1 analogue
```

```
<220> FEATURE:
<221> NAME/KEY: mat_peptide
<222> LOCATION: (1)..(31)

<400> SEQUENCE: 7

His Trp Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 8
<211> LENGTH: 31
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(31)
<220> FEATURE:
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 8

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 9
<211> LENGTH: 33
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(33)

<400> SEQUENCE: 9

His Trp Glu Gly Thr Phe Thr Ser Asp Val Ser Ser Tyr Leu Glu Glu
1               5                   10                  15

Gln Ala Ala Arg Lys Phe Ile Glu Trp Leu Val Arg Gly Lys Gly Glu
            20                  25                  30

Gly

<210> SEQ ID NO 10
<211> LENGTH: 33
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(33)
<220> FEATURE:
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 10

His Xaa Glu Gly Thr Phe Thr Ser Asp Val Ser Ser Tyr Leu Glu Glu
1               5                   10                  15

Gln Ala Ala Arg Lys Phe Ile Glu Trp Leu Val Arg Gly Lys Gly Glu
```

20                  25                  30

Gly

<210> SEQ ID NO 11
<211> LENGTH: 31
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(31)

<400> SEQUENCE: 11

His Trp Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Lys
            20                  25                  30

<210> SEQ ID NO 12
<211> LENGTH: 31
<212> TYPE: PRT
<213> ORGANISM: Artificial sequence
<220> FEATURE:
<223> OTHER INFORMATION: GLP-1 analogue
<220> FEATURE:
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 12

His Xaa Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Lys
            20                  25                  30

<210> SEQ ID NO 13
<211> LENGTH: 31
<212> TYPE: PRT
<213> ORGANISM: Artificial sequence
<220> FEATURE:
<223> OTHER INFORMATION: GLP-1 analogue

<400> SEQUENCE: 13

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 14
<211> LENGTH: 582
<212> TYPE: PRT
<213> ORGANISM: Artificial sequence
<220> FEATURE:
<223> OTHER INFORMATION: dulaglutide
<220> FEATURE:
<221> NAME/KEY: SIGNAL
<222> LOCATION: (1)..(16)
<220> FEATURE:
<221> NAME/KEY: CHAIN
<222> LOCATION: (17)..(291)
<220> FEATURE:
<221> NAME/KEY: MISC_FEATURE
<222> LOCATION: (17)..(63)
<223> OTHER INFORMATION: GLP-1 analogue peptide including C-terminal
      linker 4xG-S-4xG-S-4xG-S-A
<220> FEATURE:

```
<221> NAME/KEY: MISC_FEATURE
<222> LOCATION: (64)..(291)
<223> OTHER INFORMATION: IgG-Fc part
<220> FEATURE:
<221> NAME/KEY: DISULFID
<222> LOCATION: (71)..(362)
<220> FEATURE:
<221> NAME/KEY: DISULFID
<222> LOCATION: (74)..(365)
<220> FEATURE:
<221> NAME/KEY: SIGNAL
<222> LOCATION: (292)..(307)
<220> FEATURE:
<221> NAME/KEY: MISC_FEATURE
<222> LOCATION: (308)..(354)
<223> OTHER INFORMATION: GLP-1 analogue peptide including C-terminal
      linker 4xG-S-4xG-S-4xG-S-A
<220> FEATURE:
<221> NAME/KEY: CHAIN
<222> LOCATION: (308)..(582)
<220> FEATURE:
<221> NAME/KEY: MISC_FEATURE
<222> LOCATION: (355)..(582)
<223> OTHER INFORMATION: IgG-Fc part

<400> SEQUENCE: 14
```

Met Pro Leu Leu Leu Leu Pro Leu Leu Trp Ala Gly Ala Leu Ala
1               5                   10                  15

His Gly Glu Gly Thr Phe Thr Ser Asp Val Ser Ser Tyr Leu Glu Glu
            20                  25                  30

Gln Ala Ala Lys Glu Phe Ile Ala Trp Leu Val Lys Gly Gly Gly
            35                  40                  45

Gly Gly Gly Ser Gly Gly Gly Ser Gly Gly Gly Ser Ala Glu
    50                  55                  60

Ser Lys Tyr Gly Pro Pro Cys Pro Pro Cys Pro Ala Pro Glu Ala Ala
65                  70                  75                  80

Gly Gly Pro Ser Val Phe Leu Phe Pro Pro Lys Pro Lys Asp Thr Leu
                85                  90                  95

Met Ile Ser Arg Thr Pro Glu Val Thr Cys Val Val Val Asp Val Ser
            100                 105                 110

Gln Glu Asp Pro Glu Val Gln Phe Asn Trp Tyr Val Asp Gly Val Glu
        115                 120                 125

Val His Asn Ala Lys Thr Lys Pro Arg Glu Glu Gln Phe Asn Ser Thr
    130                 135                 140

Tyr Arg Val Val Ser Val Leu Thr Val Leu His Gln Asp Trp Leu Asn
145                 150                 155                 160

Gly Lys Glu Tyr Lys Cys Lys Val Ser Asn Lys Gly Leu Pro Ser Ser
                165                 170                 175

Ile Glu Lys Thr Ile Ser Lys Ala Lys Gly Gln Pro Arg Glu Pro Gln
            180                 185                 190

Val Tyr Thr Leu Pro Pro Ser Gln Glu Glu Met Thr Lys Asn Gln Val
        195                 200                 205

Ser Leu Thr Cys Leu Val Lys Gly Phe Tyr Pro Ser Asp Ile Ala Val
    210                 215                 220

Glu Trp Glu Ser Asn Gly Gln Pro Glu Asn Asn Tyr Lys Thr Thr Pro
225                 230                 235                 240

Pro Val Leu Asp Ser Asp Gly Ser Phe Phe Leu Tyr Ser Arg Leu Thr
                245                 250                 255

Val Asp Lys Ser Arg Trp Gln Glu Gly Asn Val Phe Ser Cys Ser Val
            260                 265                 270

Met His Glu Ala Leu His Asn His Tyr Thr Gln Lys Ser Leu Ser Leu

-continued

```
            275                 280                 285
Ser Leu Gly Met Pro Leu Leu Leu Leu Pro Leu Leu Trp Ala Gly
    290                 295                 300

Ala Leu Ala His Gly Glu Gly Thr Phe Thr Ser Asp Val Ser Tyr
305                 310                 315                 320

Leu Glu Glu Gln Ala Ala Lys Glu Phe Ile Ala Trp Leu Val Lys Gly
                325                 330                 335

Gly Gly Gly Gly Gly Ser Gly Gly Gly Ser Gly Gly Gly Gly
            340                 345                 350

Ser Ala Glu Ser Lys Tyr Gly Pro Pro Cys Pro Pro Cys Pro Ala Pro
        355                 360                 365

Glu Ala Ala Gly Gly Pro Ser Val Phe Leu Phe Pro Pro Lys Pro Lys
    370                 375                 380

Asp Thr Leu Met Ile Ser Arg Thr Pro Glu Val Thr Cys Val Val Val
385                 390                 395                 400

Asp Val Ser Gln Glu Asp Pro Glu Val Gln Phe Asn Trp Tyr Val Asp
                405                 410                 415

Gly Val Glu Val His Asn Ala Lys Thr Lys Pro Arg Glu Glu Gln Phe
            420                 425                 430

Asn Ser Thr Tyr Arg Val Val Ser Val Leu Thr Val Leu His Gln Asp
        435                 440                 445

Trp Leu Asn Gly Lys Glu Tyr Lys Cys Lys Val Ser Asn Lys Gly Leu
    450                 455                 460

Pro Ser Ser Ile Glu Lys Thr Ile Ser Lys Ala Lys Gly Gln Pro Arg
465                 470                 475                 480

Glu Pro Gln Val Tyr Thr Leu Pro Pro Ser Gln Glu Met Thr Lys
                485                 490                 495

Asn Gln Val Ser Leu Thr Cys Leu Val Lys Gly Phe Tyr Pro Ser Asp
            500                 505                 510

Ile Ala Val Glu Trp Glu Ser Asn Gly Gln Pro Glu Asn Asn Tyr Lys
        515                 520                 525

Thr Thr Pro Pro Val Leu Asp Ser Asp Gly Ser Phe Phe Leu Tyr Ser
    530                 535                 540

Arg Leu Thr Val Asp Lys Ser Arg Trp Gln Glu Gly Asn Val Phe Ser
545                 550                 555                 560

Cys Ser Val Met His Glu Ala Leu His Asn His Tyr Thr Gln Lys Ser
                565                 570                 575

Leu Ser Leu Ser Leu Gly
            580

<210> SEQ ID NO 15
<211> LENGTH: 550
<212> TYPE: PRT
<213> ORGANISM: Artificial sequence
<220> FEATURE:
<223> OTHER INFORMATION: 8W dulaglutide
<220> FEATURE:
<221> NAME/KEY: CHAIN
<222> LOCATION: (1)..(275)
<220> FEATURE:
<221> NAME/KEY: MISC_FEATURE
<222> LOCATION: (1)..(47)
<223> OTHER INFORMATION: GLP-1 analogue including C-terminal linker
      4xG-S-4xG-S-4xG-S-A
<220> FEATURE:
<221> NAME/KEY: MISC_FEATURE
<222> LOCATION: (48)..(275)
<223> OTHER INFORMATION: IgG-Fc part
<220> FEATURE:
```

```
<221> NAME/KEY: DISULFID
<222> LOCATION: (55)..(330)
<220> FEATURE:
<221> NAME/KEY: DISULFID
<222> LOCATION: (58)..(333)
<220> FEATURE:
<221> NAME/KEY: MISC_FEATURE
<222> LOCATION: (276)..(322)
<223> OTHER INFORMATION: GLP-1 analogue including C-terminal linker
      4xG-S-4xG-S-4xG-S-A
<220> FEATURE:
<221> NAME/KEY: CHAIN
<222> LOCATION: (276)..(550)
<220> FEATURE:
<221> NAME/KEY: MISC_FEATURE
<222> LOCATION: (323)..(550)
<223> OTHER INFORMATION: IgG-Fc part

<400> SEQUENCE: 15

His Trp Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45

Ser Lys Tyr Gly Pro Pro Cys Pro Pro Cys Pro Ala Pro Glu Ala Ala
    50                  55                  60

Gly Gly Pro Ser Val Phe Leu Phe Pro Pro Lys Pro Lys Asp Thr Leu
65                  70                  75                  80

Met Ile Ser Arg Thr Pro Glu Val Thr Cys Val Val Val Asp Val Ser
            85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
    130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
            165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
    210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
            245                 250                 255

Met His Glu Ala Leu His Asn His Tyr Thr Gln Lys Ser Leu Ser Leu
            260                 265                 270

Ser Leu Gly His Trp Glu Gly Thr Phe Thr Ser Asp Val Ser Ser Tyr
        275                 280                 285

Leu Glu Glu Gln Ala Ala Lys Glu Phe Ile Ala Trp Leu Val Lys Gly
    290                 295                 300

Gly Gly Gly Gly Gly Ser Gly Gly Gly Ser Gly Gly Gly Gly
305                 310                 315                 320
```

-continued

```
Ser Ala Glu Ser Lys Tyr Gly Pro Cys Pro Cys Pro Ala Pro
            325                 330                 335

Glu Ala Ala Gly Gly Pro Ser Val Phe Leu Phe Pro Pro Lys Pro Lys
            340                 345                 350

Asp Thr Leu Met Ile Ser Arg Thr Pro Glu Val Thr Cys Val Val Val
            355                 360                 365

Asp Val Ser Gln Glu Asp Pro Glu Val Gln Phe Asn Trp Tyr Val Asp
        370                 375                 380

Gly Val Glu Val His Asn Ala Lys Thr Lys Pro Arg Glu Glu Gln Phe
385                 390                 395                 400

Asn Ser Thr Tyr Arg Val Val Ser Val Leu Thr Val Leu His Gln Asp
                405                 410                 415

Trp Leu Asn Gly Lys Glu Tyr Lys Cys Lys Val Ser Asn Lys Gly Leu
            420                 425                 430

Pro Ser Ser Ile Glu Lys Thr Ile Ser Lys Ala Lys Gly Gln Pro Arg
            435                 440                 445

Glu Pro Gln Val Tyr Thr Leu Pro Pro Ser Gln Glu Glu Met Thr Lys
    450                 455                 460

Asn Gln Val Ser Leu Thr Cys Leu Val Lys Gly Phe Tyr Pro Ser Asp
465                 470                 475                 480

Ile Ala Val Glu Trp Glu Ser Asn Gly Gln Pro Glu Asn Asn Tyr Lys
                485                 490                 495

Thr Thr Pro Pro Val Leu Asp Ser Asp Gly Ser Phe Phe Leu Tyr Ser
            500                 505                 510

Arg Leu Thr Val Asp Lys Ser Arg Trp Gln Gln Gly Asn Val Phe Ser
        515                 520                 525

Cys Ser Val Met His Glu Ala Leu His Asn His Tyr Thr Gln Lys Ser
530                 535                 540

Leu Ser Leu Ser Leu Gly
545                 550

<210> SEQ ID NO 16
<211> LENGTH: 36
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(35)

<400> SEQUENCE: 16

His Trp Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Gly Lys
            20                  25                  30

Gly Gly Ser Lys
        35

<210> SEQ ID NO 17
<211> LENGTH: 36
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(35)
<220> FEATURE:
```

```
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 17

His Xaa Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Arg Gly Lys
            20                  25                  30

Gly Gly Ser Lys
            35

<210> SEQ ID NO 18
<211> LENGTH: 31
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(31)

<400> SEQUENCE: 18

His Trp Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Arg Lys
            20                  25                  30

<210> SEQ ID NO 19
<211> LENGTH: 31
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(31)
<220> FEATURE:
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 19

His Xaa Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Arg Lys
            20                  25                  30

<210> SEQ ID NO 20
<211> LENGTH: 32
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(32)

<400> SEQUENCE: 20

His Trp Glu Gly Thr Phe Thr Ser Asp Val Ser Ser Tyr Leu Glu Glu
 1               5                  10                  15

Gln Ala Ala Arg Glu Phe Ile Ala Trp Leu Val Arg Gly Arg Pro Lys
            20                  25                  30
```

-continued

```
<210> SEQ ID NO 21
<211> LENGTH: 32
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(32)
<220> FEATURE:
<221> NAME/KEY: MOD_RES
<222> LOCATION: (2)..(2)
<223> OTHER INFORMATION: Xaa at position 2 is Aib (2-Aminoisobutyric
      acid)

<400> SEQUENCE: 21

His Xaa Glu Gly Thr Phe Thr Ser Asp Val Ser Ser Tyr Leu Glu Glu
1               5                   10                  15

Gln Ala Ala Arg Glu Phe Ile Ala Trp Leu Val Arg Gly Arg Pro Lys
            20                  25                  30

<210> SEQ ID NO 22
<211> LENGTH: 29
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(29)

<400> SEQUENCE: 22

Glu Gly Thr Phe Thr Ser Asp Val Ser Ser Tyr Leu Glu Gly Gln Ala
1               5                   10                  15

Ala Lys Glu Phe Ile Ala Trp Leu Val Arg Gly Arg Gly
            20                  25

<210> SEQ ID NO 23
<211> LENGTH: 31
<212> TYPE: PRT
<213> ORGANISM: Artificial sequence
<220> FEATURE:
<223> OTHER INFORMATION: GLP-1 analogue
<220> FEATURE:
<221> NAME/KEY: mat_peptide
<222> LOCATION: (1)..(31)

<400> SEQUENCE: 23

Glu Gly Thr Phe Thr Ser Asp Val Ser Ser Tyr Leu Glu Glu Gln Ala
1               5                   10                  15

Ala Arg Lys Phe Ile Glu Trp Leu Val Arg Gly Lys Gly Glu Gly
            20                  25                  30

<210> SEQ ID NO 24
<211> LENGTH: 14
<212> TYPE: PRT
<213> ORGANISM: Artificial sequence
<220> FEATURE:
<223> OTHER INFORMATION: Peptide (N-terminal extension)
<220> FEATURE:
<221> NAME/KEY: PROPEP
<222> LOCATION: (1)..(14)

<400> SEQUENCE: 24

Asp Val Lys Pro Gly Gln Pro Met Tyr Asp Asp Asp Asp Lys
1               5                   10

<210> SEQ ID NO 25
```

```
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is L-histidine
<220> FEATURE:
<221> NAME/KEY: MISC_FEATURE
<222> LOCATION: (6)..(6)
<223> OTHER INFORMATION: Xaa is Phe or Leu
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (12)..(12)
<223> OTHER INFORMATION: Xaa is Ser, Arg, Val, or Leu
<220> FEATURE:
<221> NAME/KEY: MISC_FEATURE
<222> LOCATION: (13)..(13)
<223> OTHER INFORMATION: Xaa is Tyr or Gln
<220> FEATURE:
<221> NAME/KEY: MISC_FEATURE
<222> LOCATION: (14)..(14)
<223> OTHER INFORMATION: Xaa is Leu or Met
<220> FEATURE:
<221> NAME/KEY: MISC_FEATURE
<222> LOCATION: (16)..(16)
<223> OTHER INFORMATION: Xaa is Gly or Glu
<220> FEATURE:
<221> NAME/KEY: MISC_FEATURE
<222> LOCATION: (17)..(17)
<223> OTHER INFORMATION: Xaa is Gln, Glu, or Arg
<220> FEATURE:
<221> NAME/KEY: MISC_FEATURE
<222> LOCATION: (19)..(19)
<223> OTHER INFORMATION: Xaa is Ala or Val
<220> FEATURE:
<221> NAME/KEY: MISC_FEATURE
<222> LOCATION: (20)..(20)
<223> OTHER INFORMATION: Xaa is Arg or Lys
<220> FEATURE:
<221> NAME/KEY: MISC_FEATURE
<222> LOCATION: (21)..(21)
<223> OTHER INFORMATION: Xaa is Glu, Lys, or Leu
<220> FEATURE:
<221> NAME/KEY: MISC_FEATURE
<222> LOCATION: (24)..(24)
<223> OTHER INFORMATION: Xaa is Ala, Glu, or Arg
<220> FEATURE:
<221> NAME/KEY: MISC_FEATURE
<222> LOCATION: (25)..(25)
<223> OTHER INFORMATION: Xaa is Trp or His
<220> FEATURE:
<221> NAME/KEY: MISC_FEATURE
<222> LOCATION: (27)..(27)
<223> OTHER INFORMATION: Xaa is Val
<220> FEATURE:
<221> NAME/KEY: MISC_FEATURE
<222> LOCATION: (28)..(28)
<223> OTHER INFORMATION: Xaa is Arg, His, Asn, or Gln
<220> FEATURE:
<221> NAME/KEY: MISC_FEATURE
<222> LOCATION: (29)..(29)
<223> OTHER INFORMATION: Xaa is Gly or Ala
<220> FEATURE:
<221> NAME/KEY: MISC_FEATURE
<222> LOCATION: (30)..(30)
<223> OTHER INFORMATION: Xaa is Arg, Lys, or Gly
<220> FEATURE:
<221> NAME/KEY: MISC_FEATURE
<222> LOCATION: (31)..(31)
<223> OTHER INFORMATION: Xaa is Gly, Lys, Pro, or absent
<220> FEATURE:
<221> NAME/KEY: MISC_FEATURE
```

```
<222> LOCATION: (32)..(32)
<223> OTHER INFORMATION: Xaa is Ser, Gly, Ala, Glu, Pro, Lys, or absent
<220> FEATURE:
<221> NAME/KEY: MISC_FEATURE
<222> LOCATION: (33)..(33)
<223> OTHER INFORMATION: Xaa is Ser, Gly, Ala, Glu, Pro, or absent
<220> FEATURE:
<221> NAME/KEY: MISC_FEATURE
<222> LOCATION: (34)..(34)
<223> OTHER INFORMATION: Xaa is Ser, Gly, Ala, Glu, Pro, or absent
<220> FEATURE:
<221> NAME/KEY: MISC_FEATURE
<222> LOCATION: (35)..(35)
<223> OTHER INFORMATION: Xaa is Ser, Gly, Ala, Glu, Pro, or absent
<220> FEATURE:
<221> NAME/KEY: MISC_FEATURE
<222> LOCATION: (36)..(36)
<223> OTHER INFORMATION: Xaa is Lys or absent

<400> SEQUENCE: 25

Xaa Trp Glu Gly Thr Xaa Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Xaa Xaa Xaa
            20                  25                  30

Xaa Xaa Xaa Xaa
        35

<210> SEQ ID NO 26
<211> LENGTH: 31
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is L-histidine
<220> FEATURE:
<221> NAME/KEY: MISC_FEATURE
<222> LOCATION: (6)..(6)
<223> OTHER INFORMATION: Xaa is Phe or Leu
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (12)..(12)
<223> OTHER INFORMATION: Xaa is Ser, Arg, Val, or Leu
<220> FEATURE:
<221> NAME/KEY: MISC_FEATURE
<222> LOCATION: (13)..(13)
<223> OTHER INFORMATION: Xaa is Tyr or Gln
<220> FEATURE:
<221> NAME/KEY: MISC_FEATURE
<222> LOCATION: (14)..(14)
<223> OTHER INFORMATION: Xaa is Leu or Met
<220> FEATURE:
<221> NAME/KEY: MISC_FEATURE
<222> LOCATION: (16)..(16)
<223> OTHER INFORMATION: Xaa is Gly or Glu
<220> FEATURE:
<221> NAME/KEY: MISC_FEATURE
<222> LOCATION: (17)..(17)
<223> OTHER INFORMATION: Xaa is Gln, Glu, or Arg
<220> FEATURE:
<221> NAME/KEY: MISC_FEATURE
<222> LOCATION: (19)..(19)
<223> OTHER INFORMATION: Xaa is Ala or Val
<220> FEATURE:
<221> NAME/KEY: MISC_FEATURE
<222> LOCATION: (20)..(20)
<223> OTHER INFORMATION: Xaa is Arg or Lys
<220> FEATURE:
<221> NAME/KEY: MISC_FEATURE
```

-continued

```
<222> LOCATION: (21)..(21)
<223> OTHER INFORMATION: Xaa is Glu, Lys, or Leu
<220> FEATURE:
<221> NAME/KEY: MISC_FEATURE
<222> LOCATION: (24)..(24)
<223> OTHER INFORMATION: Xaa is Ala, Glu, or Arg
<220> FEATURE:
<221> NAME/KEY: MISC_FEATURE
<222> LOCATION: (25)..(25)
<223> OTHER INFORMATION: Xaa is Trp or His
<220> FEATURE:
<221> NAME/KEY: MISC_FEATURE
<222> LOCATION: (27)..(27)
<223> OTHER INFORMATION: Xaa is Val
<220> FEATURE:
<221> NAME/KEY: MISC_FEATURE
<222> LOCATION: (28)..(28)
<223> OTHER INFORMATION: Xaa is Arg, His, Asn, or Gln
<220> FEATURE:
<221> NAME/KEY: MISC_FEATURE
<222> LOCATION: (29)..(29)
<223> OTHER INFORMATION: Xaa is Gly or Ala
<220> FEATURE:
<221> NAME/KEY: MISC_FEATURE
<222> LOCATION: (30)..(30)
<223> OTHER INFORMATION: Xaa is Arg, Lys, or Gly
<220> FEATURE:
<221> NAME/KEY: MISC_FEATURE
<222> LOCATION: (31)..(31)
<223> OTHER INFORMATION: Xaa is Gly, Lys, Pro, or absent

<400> SEQUENCE: 26

Xaa Trp Glu Gly Thr Xaa Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Xaa Xaa
            20                  25                  30

<210> SEQ ID NO 27
<211> LENGTH: 33
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is L-histidine
<220> FEATURE:
<221> NAME/KEY: MISC_FEATURE
<222> LOCATION: (6)..(6)
<223> OTHER INFORMATION: Xaa is Phe or Leu
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (12)..(12)
<223> OTHER INFORMATION: Xaa is Ser, Arg, Val, or Leu
<220> FEATURE:
<221> NAME/KEY: MISC_FEATURE
<222> LOCATION: (13)..(13)
<223> OTHER INFORMATION: Xaa is Tyr or Gln
<220> FEATURE:
<221> NAME/KEY: MISC_FEATURE
<222> LOCATION: (14)..(14)
<223> OTHER INFORMATION: Xaa is Leu or Met
<220> FEATURE:
<221> NAME/KEY: MISC_FEATURE
<222> LOCATION: (16)..(16)
<223> OTHER INFORMATION: Xaa is Gly or Glu
<220> FEATURE:
<221> NAME/KEY: MISC_FEATURE
<222> LOCATION: (17)..(17)
<223> OTHER INFORMATION: Xaa is Gln, Glu, or Arg
<220> FEATURE:
```

```
<221> NAME/KEY: MISC_FEATURE
<222> LOCATION: (19)..(19)
<223> OTHER INFORMATION: Xaa is Ala or Val
<220> FEATURE:
<221> NAME/KEY: MISC_FEATURE
<222> LOCATION: (20)..(20)
<223> OTHER INFORMATION: Xaa is Arg or Lys
<220> FEATURE:
<221> NAME/KEY: MISC_FEATURE
<222> LOCATION: (21)..(21)
<223> OTHER INFORMATION: Xaa is Glu, Lys, or Leu
<220> FEATURE:
<221> NAME/KEY: MISC_FEATURE
<222> LOCATION: (24)..(24)
<223> OTHER INFORMATION: Xaa is Ala, Glu, or Arg
<220> FEATURE:
<221> NAME/KEY: MISC_FEATURE
<222> LOCATION: (25)..(25)
<223> OTHER INFORMATION: Xaa is Trp or His
<220> FEATURE:
<221> NAME/KEY: MISC_FEATURE
<222> LOCATION: (27)..(27)
<223> OTHER INFORMATION: Xaa is Val
<220> FEATURE:
<221> NAME/KEY: MISC_FEATURE
<222> LOCATION: (28)..(28)
<223> OTHER INFORMATION: Xaa is Arg, His, Asn, or Gln
<220> FEATURE:
<221> NAME/KEY: MISC_FEATURE
<222> LOCATION: (29)..(29)
<223> OTHER INFORMATION: Xaa is Gly or Ala
<220> FEATURE:
<221> NAME/KEY: MISC_FEATURE
<222> LOCATION: (30)..(30)
<223> OTHER INFORMATION: Xaa is Arg, Lys, or Gly
<220> FEATURE:
<221> NAME/KEY: MISC_FEATURE
<222> LOCATION: (31)..(31)
<223> OTHER INFORMATION: Xaa is Gly, Lys, Pro, or absent
<220> FEATURE:
<221> NAME/KEY: MISC_FEATURE
<222> LOCATION: (32)..(32)
<223> OTHER INFORMATION: Xaa is Ser, Gly, Ala, Glu, Pro, Lys, or absent
<220> FEATURE:
<221> NAME/KEY: MISC_FEATURE
<222> LOCATION: (33)..(33)
<223> OTHER INFORMATION: Xaa is Ser, Gly, Ala, Glu, Pro, or absent

<400> SEQUENCE: 27

Xaa Trp Glu Gly Thr Xaa Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Xaa Xaa Xaa
            20                  25                  30

Xaa

<210> SEQ ID NO 28
<211> LENGTH: 36
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is L-histidine
<220> FEATURE:
<221> NAME/KEY: MISC_FEATURE
<222> LOCATION: (6)..(6)
<223> OTHER INFORMATION: Xaa is Phe or Leu
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
```

```
<222> LOCATION: (12)..(12)
<223> OTHER INFORMATION: Xaa is Ser, Arg, Val, or Leu
<220> FEATURE:
<221> NAME/KEY: MISC_FEATURE
<222> LOCATION: (13)..(13)
<223> OTHER INFORMATION: Xaa is Tyr or Gln
<220> FEATURE:
<221> NAME/KEY: MISC_FEATURE
<222> LOCATION: (14)..(14)
<223> OTHER INFORMATION: Xaa is Leu or Met
<220> FEATURE:
<221> NAME/KEY: MISC_FEATURE
<222> LOCATION: (16)..(16)
<223> OTHER INFORMATION: Xaa is Gly or Glu
<220> FEATURE:
<221> NAME/KEY: MISC_FEATURE
<222> LOCATION: (17)..(17)
<223> OTHER INFORMATION: Xaa is Gln, Glu, or Arg
<220> FEATURE:
<221> NAME/KEY: MISC_FEATURE
<222> LOCATION: (19)..(19)
<223> OTHER INFORMATION: Xaa is Ala or Val
<220> FEATURE:
<221> NAME/KEY: MISC_FEATURE
<222> LOCATION: (20)..(20)
<223> OTHER INFORMATION: Xaa is Arg or Lys
<220> FEATURE:
<221> NAME/KEY: MISC_FEATURE
<222> LOCATION: (21)..(21)
<223> OTHER INFORMATION: Xaa is Glu, Lys, or Leu
<220> FEATURE:
<221> NAME/KEY: MISC_FEATURE
<222> LOCATION: (24)..(24)
<223> OTHER INFORMATION: Xaa is Ala, Glu, or Arg
<220> FEATURE:
<221> NAME/KEY: MISC_FEATURE
<222> LOCATION: (25)..(25)
<223> OTHER INFORMATION: Xaa is Trp or His
<220> FEATURE:
<221> NAME/KEY: MISC_FEATURE
<222> LOCATION: (27)..(27)
<223> OTHER INFORMATION: Xaa is Val
<220> FEATURE:
<221> NAME/KEY: MISC_FEATURE
<222> LOCATION: (28)..(28)
<223> OTHER INFORMATION: Xaa is Arg, His, Asn, or Gln
<220> FEATURE:
<221> NAME/KEY: MISC_FEATURE
<222> LOCATION: (29)..(29)
<223> OTHER INFORMATION: Xaa is Gly or Ala
<220> FEATURE:
<221> NAME/KEY: MISC_FEATURE
<222> LOCATION: (30)..(30)
<223> OTHER INFORMATION: Xaa is Arg, Lys, or Gly
<220> FEATURE:
<221> NAME/KEY: MISC_FEATURE
<222> LOCATION: (31)..(31)
<223> OTHER INFORMATION: Xaa is Gly, Lys, Pro, or absent
<220> FEATURE:
<221> NAME/KEY: MISC_FEATURE
<222> LOCATION: (32)..(32)
<223> OTHER INFORMATION: Xaa is Ser, Gly, Ala, Glu, Pro, or Lys
<220> FEATURE:
<221> NAME/KEY: MISC_FEATURE
<222> LOCATION: (33)..(33)
<223> OTHER INFORMATION: Xaa is Ser, Gly, Ala, Glu, or Pro
<220> FEATURE:
<221> NAME/KEY: MISC_FEATURE
<222> LOCATION: (34)..(34)
<223> OTHER INFORMATION: Xaa is Ser, Gly, Ala, Glu, or Pro
<220> FEATURE:
<221> NAME/KEY: MISC_FEATURE
<222> LOCATION: (35)..(35)
<223> OTHER INFORMATION: Xaa is Ser, Gly, Ala, Glu, or Pro
<220> FEATURE:
<221> NAME/KEY: MISC_FEATURE
<222> LOCATION: (36)..(36)
<223> OTHER INFORMATION: Xaa is Lys
```

-continued

```
<400> SEQUENCE: 28

Xaa Trp Glu Gly Thr Xaa Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Xaa Xaa Xaa
            20                  25                  30

Xaa Xaa Xaa Xaa
        35

<210> SEQ ID NO 29
<211> LENGTH: 32
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is L-histidine
<220> FEATURE:
<221> NAME/KEY: MISC_FEATURE
<222> LOCATION: (6)..(6)
<223> OTHER INFORMATION: Xaa is Phe or Leu
<220> FEATURE:
<221> NAME/KEY: MISC_FEATURE
<222> LOCATION: (10)..(10)
<223> OTHER INFORMATION: Xaa is Val or Leu
<220> FEATURE:
<221> NAME/KEY: MISC_FEATURE
<222> LOCATION: (12)..(12)
<223> OTHER INFORMATION: Xaa is Ser, Arg, Val, or Leu
<220> FEATURE:
<221> NAME/KEY: MISC_FEATURE
<222> LOCATION: (13)..(13)
<223> OTHER INFORMATION: Xaa is Tyr or Gln
<220> FEATURE:
<221> NAME/KEY: MISC_FEATURE
<222> LOCATION: (14)..(14)
<223> OTHER INFORMATION: Xaa is Leu or Met
<220> FEATURE:
<221> NAME/KEY: MISC_FEATURE
<222> LOCATION: (16)..(16)
<223> OTHER INFORMATION: Xaa is Gly or Glu
<220> FEATURE:
<221> NAME/KEY: MISC_FEATURE
<222> LOCATION: (17)..(17)
<223> OTHER INFORMATION: Xaa is Gln, Glu, or Arg
<220> FEATURE:
<221> NAME/KEY: MISC_FEATURE
<222> LOCATION: (19)..(19)
<223> OTHER INFORMATION: Xaa is Ala or Val
<220> FEATURE:
<221> NAME/KEY: MISC_FEATURE
<222> LOCATION: (20)..(20)
<223> OTHER INFORMATION: Xaa is Arg or Lys
<220> FEATURE:
<221> NAME/KEY: MISC_FEATURE
<222> LOCATION: (21)..(21)
<223> OTHER INFORMATION: Xaa is Glu, Lys, or Leu
<220> FEATURE:
<221> NAME/KEY: MISC_FEATURE
<222> LOCATION: (24)..(24)
<223> OTHER INFORMATION: Xaa is Ala, Glu, or Arg
<220> FEATURE:
<221> NAME/KEY: MISC_FEATURE
<222> LOCATION: (25)..(25)
<223> OTHER INFORMATION: Xaa is Trp or His
<220> FEATURE:
<221> NAME/KEY: MISC_FEATURE
<222> LOCATION: (27)..(27)
<223> OTHER INFORMATION: Xaa is Val
<220> FEATURE:
<221> NAME/KEY: MISC_FEATURE
<222> LOCATION: (28)..(28)
<223> OTHER INFORMATION: Xaa is Arg, His, Asn, or Gln
<220> FEATURE:
```

```
<221> NAME/KEY: MISC_FEATURE
<222> LOCATION: (29)..(29)
<223> OTHER INFORMATION: Xaa is Gly or Ala
<220> FEATURE:
<221> NAME/KEY: MISC_FEATURE
<222> LOCATION: (30)..(30)
<223> OTHER INFORMATION: Xaa is Arg, Lys, or Gly
<220> FEATURE:
<221> NAME/KEY: MISC_FEATURE
<222> LOCATION: (31)..(31)
<223> OTHER INFORMATION: Xaa is Gly, Lys, Pro, or absent
<220> FEATURE:
<221> NAME/KEY: MISC_FEATURE
<222> LOCATION: (32)..(32)
<223> OTHER INFORMATION: Xaa is Ser, Gly, Ala, Glu, Pro, Lys, or absent

<400> SEQUENCE: 29

Xaa Trp Glu Gly Thr Xaa Thr Ser Asp Xaa Ser Xaa Xaa Xaa Glu Xaa
1               5                   10                  15

Xaa Ala Xaa Xaa Xaa Phe Ile Xaa Xaa Leu Xaa Xaa Xaa Xaa Xaa Xaa
            20                  25                  30
```